United States Patent
Swinnen et al.

(10) Patent No.: US 8,263,595 B2
(45) Date of Patent: Sep. 11, 2012

(54) TRIAZOLOPYRIDINE COMPOUNDS AND THEIR USE AS ASK INHIBITORS

(75) Inventors: Dominique Swinnen, Beaumont (FR); Catherine Jorand-Lebrun, Contamine-Sarzin (FR); Tania Grippi-Vallotton, Puplinge (CH); Mathilde Muzerelle, Gaillard (FR); Amanda Royle, Saffron Walden (GB); Jacqueline MacRitchie, Saffron Walden (GB); Richard Hill, Cambs (GB); Jeffrey P. Shaw, Vessy (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/666,445

(22) PCT Filed: Aug. 20, 2008

(86) PCT No.: PCT/EP2008/060884
§ 371 (c)(1), (2), (4) Date: Dec. 23, 2009

(87) PCT Pub. No.: WO2009/027283
PCT Pub. Date: Mar. 5, 2009

(65) Prior Publication Data
US 2010/0197681 A1    Aug. 5, 2010

Related U.S. Application Data

(60) Provisional application No. 60/966,989, filed on Aug. 31, 2007.

(30) Foreign Application Priority Data

Aug. 31, 2007  (EP) .................................... 07115408

(51) Int. Cl.
*A61K 31/5377* (2006.01)
*C07D 471/04* (2006.01)
(52) U.S. Cl. ..................................... 514/233.2; 546/119
(58) Field of Classification Search .................. None
See application file for complete search history.

(56) References Cited

U.S. PATENT DOCUMENTS 7,041,675 B2    5/2006 Lubisch et al.

FOREIGN PATENT DOCUMENTS

| EP | 1 894 931 | 3/2008 |
| WO | WO 01/57038 | 8/2001 |
| WO | WO 02/072579 | 9/2002 |
| WO | WO 2004/072072 | 8/2004 |
| WO | WO 2006/018727 | 2/2006 |
| WO | WO 2007/095588 | 8/2007 |
| WO | WO 2008/025821 | 3/2008 |
| WO | WO 2008025821 A1 * | 3/2008 |

OTHER PUBLICATIONS

Chong, H. et al. "Synthesis and Potent Antitumor Activities of Novel 1,3,5-*cis,cis*-Triaminocyclohexane *N*-Pyridyl Derivatives" *J. Med. Chem.*, 2004, pp. 5230-5234, vol. 47.
Miyaura, N. et al. "Palladium-Catalyzed Cross-Coupling Reactions of Organoboron Compounds" *Chem. Rev.*, 1995, pp. 2457-2483, vol. 95.
Nagai, H. et al. "Pathophysiological Roles of ASK1-MAP Kinase Signaling Pathways" *Journal of Biochemistry and Molecular Biology*, Jan. 2007, pp. 1-6, vol. 40, No. 1.
Nettekoven, M. et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes" *Synthesis*, 2003, pp. 1649-1652, No. 11, XP-002469830.
Itoh, T. et al. "Direct synthesis of hetero-biaryl compounds containing an unprotected $NH_2$ group via Suzuki-Miyaura reaction" *Tetrahedron Letters*, 2005, pp. 3573-3577, vol. 46.
Written Opinion in International Application No. PCT/EP2008/060884, Nov. 26, 2008, pp. 1-8.

* cited by examiner

*Primary Examiner* — Yong Chu
(74) *Attorney, Agent, or Firm* — Saliwanchik, Lloyd & Eisenschenk

(57) ABSTRACT

The present invention relates to triazolopyridine compounds according to Formula (I), their use as medicament, for treating autoimmune disorders, inflammatory diseases, cardiovascular diseases and/or neurodegenerative diseases and a process for their preparation.

5 Claims, No Drawings

TRIAZOLOPYRIDINE COMPOUNDS AND THEIR USE AS ASK INHIBITORS

CROSS-REFERENCE TO RELATED APPLICATION

This application is the U.S. national stage application of International Patent Application No. PCT/EP2008/060884, filed Aug. 20, 2008, which claims the benefit of U.S. Provisional Patent Application No. 60/966,989, filed Aug. 31, 2007, the disclosures of which are hereby incorporated by reference in their entirety, including all figures, tables and amino acid or nucleic acid sequences.

FIELD OF THE INVENTION

The present invention relates to triazolopyridine compounds according to Formula (I), their use as medicament, for treating autoimmune disorders, inflammatory diseases, cardiovascular diseases and/or neurodegenerative diseases and a process for their preparation.

BACKGROUND OF THE INVENTION

ASK (apoptosis signal-regulating kinase) has been described as a mitogen-activated protein kinase. ASK-1 and ASK-2 have been described as members of the ASK family. ASK-1 is a MAPKKK (mitogen-activated protein kinase kinase kinase). Human and mouse ASK-1 consist of 1374 and 1380 amino acids, respectively, and possess a serine/threonine kinase domain. ASK-1 is activated by environmental stress. The stimuli include inter alia $H_2O_2$, LPS, ROS (reactive oxygen species), ER stress, influx of calcium ions, and various cytokines such as TNF (tumor necrosis factor) have been described to be stimuli. ASK-1 in turn induces various stress responses including apoptosis and has been described to mediate various cellular responses including survival and differentiation. ASK-1 is a member of the MAPKKK family that constitutes the JNK and p38 MAP kinase (MAPK) cascades. Trx (thioredoxin) was identified as a repressor of ASK-1 and also forms part of the "ASK-1 signalosome", a high molecular mass complex. ASK has been described to be involved in various diseases associated with autoimmune disorders and neurodegenerative disorders (e.g. H. Nagai et al., J. Biochem. and Mol. Biol., Vol. 40, No. 1, January 2007, pp. 1-6).

SUMMARY OF THE INVENTION

According to one aspect of the invention, are provided triazolopyridine compounds according to Formula (I):

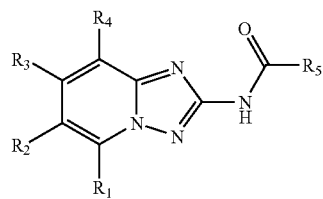

Formula (I)

wherein
$R_1$ is selected from
a. hydrogen;
b. $C_1$-$C_6$-alkyl;
c. $C_2$-$C_6$-alkenyl optionally substituted with $C_1$-$C_6$-alkyl;
d. —$NR_6R_7$;
e. $C_3$-$C_8$-cycloalkoxy, $C_1$-$C_6$-alkoxy;
f. $C_3$-$C_8$-cycloalkyl sulfanyl, $C_1$-$C_6$-alkyl sulfanyl; and
g. 5 or 6-membered heteroaryl having at least one heteroatom selected from N, S and O, said heteroaryl being optionally substituted with $C_1$-$C_6$ alkyl, halogen, or $C_1$-$C_6$ alkoxy;
$R_2$ is selected from
a. hydrogen;
b. halogen;
c. aryl optionally substituted with $R_{10}$, $R_{11}$ and/or $R_{12}$; and
d. 5 to 10-membered heteroaryl having at least one heteroatom selected from N, S and O and optionally substituted with $C_1$-$C_6$ alkyl;
or $R_1$ and $R_2$ taken together form a —C=C—C=C— group-;
$R_3$ is selected from
a. hydrogen;
b. halogen; and
c. $C_1$-$C_6$-alkyl optionally substituted with at least one fluoro;
$R_4$ is selected from
a. hydrogen; and
b. 5 or 6-membered heteroaryl having at least one heteroatom selected from N, S and O;
$R_5$ is selected from
a. $C_1$-$C_6$-alkyl optionally substituted with at least one of the following groups
  i. alkoxycarbonyl,
  ii. $C_1$-$C_6$-alkoxy,
  iii. —NC(O)R' wherein R' is aryl optionally substituted with $C_1$-$C_6$-alkyl,
  iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$-cycloalkyl optionally substituted with phenyl;
e. 3 to 8-membered heterocycloalkyl having a heteroatom selected from N, S and O optionally substituted with an acyl group;
f. aryl optionally substituted with at least one of the following groups
  i. $C_1$-$C_6$-alkyl,
  ii. perfluoro-$C_1$-$C_6$-alkyl,
  iii. at least one $C_1$-$C_6$-alkoxy optionally substituted with $C_1$-$C_6$-alkoxy carbonyl,
  iv. phenyl,
  v. $C_1$-$C_6$-alkyl sulfonyl,
  vi. —NHC(O)$C_1$-$C_6$-alkyl,
  vii. amino-$C_1$-$C_6$-alkyl wherein amino is selected from —$NH_2$, —NH$C_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy,
  viii. —N($C_1$-$C_6$-alkyl)($C_1$-$C_6$-alkoxy-$C_1$-$C_6$-alkyl),
  ix. 5 to 6-membered heterocycloalkyl-$C_1$-$C_6$-alkyl having a heteroatom selected from N and O,
  x. amido-$C_1$-$C_6$-alkyl,
  xi. $C_1$-$C_6$-alkoxy,
  xii. halogen;

g. 5 to 10-membered heteroaryl having at least one heteroatom selected from N, O or S optionally substituted with halogen; and
h. pyridinyl optionally substituted with at least one of the following groups
   i. halogen,
   ii. $C_1$-$C_6$-alkyl,
   iii. amino-$C_1$-$C_6$-alkyl wherein amino is selected from —$NH_2$, —$NHC_1$-$C_6$-alkyl or —$N(C_1$-$C_6$-alkyl$)_2$, wherein the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or hydroxy;
   iv. —NH(hydroxy-$C_1$-$C_6$-alkyl),
   v. —NH-(5-membered heteroaryl-$C_1$-$C_6$-alkyl having as heteroatom O),
   vi. 5 or 6-membered heterocycloalkyl-$C_1$-$C_6$-alkyl having at least one heteroatom selected from O and N;
   vii. 5 or 6-membered heterocycloalkyl having at least one heteroatom selected from O and N optionally substituted with hydroxy, —C(O)OR' wherein R' is $C_1$-$C_6$-alkyl, halogen or $C_1$-$C_6$-alkyl;
   viii. amino;
   ix. —NH(amino-$C_1$-$C_6$-alkyl);
   x. —N($C_1$-$C_6$-alkyl$)_2$;
$R_6$ is selected from
a. $C_1$-$C_6$-alkyl optionally substituted with one or two hydroxy groups,
b. phenyl optionally substituted with at least one of the following groups
   i. halogen
   ii. $C_1$-$C_6$-alkyl, or
   iii. $C_1$-$C_6$-alkoxy;
c. 5 or 6-membered heterocycloalkyl having a heteroatom selected from O and N optionally substituted with $C_1$-$C_6$-alkyl;
d. $C_3$-$C_8$-cycloalkyl optionally substituted with $R_8$; and
e. —$(CH_2)_n R_9$ wherein n equals 1, 2 or 3;
$R_7$ is
a. hydrogen or
b. $C_1$-$C_6$-alkyl;
or $R_6$ and $R_7$ can form a 3 to 8-membered heterocycloalkyl with the N to which they are attached to and wherein the heterocycloalkyl is optionally substituted with $C_1$-$C_6$-alkyl;
$R_8$ is selected from
a. hydrogen;
b. hydroxy;
c. $C_1$-$C_6$-alkyl optionally substituted with hydroxy;
d. C(O)O—$C_1$-$C_6$-alkyl; and
e. —$NH_2$;
$R_9$ is selected from
a. $C_3$-$C_8$-cycloalkyl optionally substituted with an unsubstituted $C_1$-$C_6$-alkyl;
b. 5 or 6-membered heterocycloalkyl having a heteroatom selected from N and O optionally substituted with $C_1$-$C_6$-alkyl;
c. 5 or 6-membered heteroaryl having a heteroatom selected from N and O optionally substituted with $C_1$-$C_6$-alkyl;
d. phenyl;
$R_{10}$, $R_{11}$ and $R_{12}$ are each independently selected from
a. hydrogen;
b. halogen;
c. hydroxy;
d. $C_1$-$C_6$-alkyl;
e. $C_1$-$C_6$-alkoxy;
f. cyano;
g. —C(o)NH($C_1$-$C_6$-alkyl)amino wherein the amino is —N($CH_3$)$_2$); and
h. —$NH_2$.
Any of the above chemical groups can be optionally substituted as laid out in the below definitions.

According to another aspect of the invention, are provided triazolopyridine compound intermediates.

According to another aspect of the invention, are provided triazolopyridine compounds according to Formula (I) for use as medicament.

According to another aspect of the invention, are provided pharmaceutical formulations comprising triazolopyridine compounds according to Formula (I).

According to another aspect of the invention, are provided triazolopyridine compounds according to Formula (I), which are able to modulate, especially inhibit the activity or function of ASK, in particular ASK-1, in disease states in mammals, especially in humans.

According to another aspect of the invention, are provided methods for the prevention or treatment of autoimmune diseases, inflammatory diseases, cardiovascular diseases and/or neurodegenerative diseases by administering an effective amount of a triazolopyridine compounds according to Formula (I) to a subject in need thereof.

According to another aspect of the invention, are provided methods for the prevention or treatment of autoimmune diseases, inflammatory diseases, cardiovascular diseases and/or neurodegenerative diseases by administering an effective amount of a triazolopyridine compounds according to Formula (I) to a subject in need thereof, by modulating, especially inhibiting the activity or function of ASK.

According to another aspect of the invention, is provided a process for the preparation of a triazolopyridine compound according to Formula (I).

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

The term "alkyl" refers to a linear or branched saturated hydrocarbon chain; this term is exemplified by groups such as methyl; ethyl; n-propyl; isopropyl; n-butyl; isobutyl; tert-butyl; n-hexyl. The term "$C_1$-$C_6$-alkyl" refers to alkyl groups having 1 to 6 carbon atoms.

The term "alkenyl" refers to unsaturated alkyl groups having at least one double bond and includes both linear- and branched alkenyl groups; this term is exemplified by groups such as propenyl, but-3-enyl, pent-4-enyl.

The term "$C_2$-$C_6$ alkenyl" refers to alkenyl groups having from 2 to 6 carbon atoms.

The term "aryl" refers to an aromatic carbocyclic group having at least one aromatic ring (e.g. phenyl or biphenyl) or multiple condensed rings in which at least one ring is aromatic, (e.g. naphthyl, anthryl, or phenanthryl).

The term "heteroaryl" refers to a monocyclic heteroaromatic, or a bicyclic or a tricyclic fused-ring heteroaromatic group, wherein the at least one heteroatom selected from nitrogen, oxygen, and sulfur. $C_3$-$C_8$-heteroaryl, $C_3$-$C_{10}$-heteroaryl etc. refers to the size of the corresponding heteroaryl. Particular examples of heteroaromatic groups include e.g., 2,3-dihydro benzofuranyl, 1-oxidopyridinyl, 2,3-dihydro-1, 4-benzo dioxinyl, quinoxalinyl, 2,2-difluoro-1,3-benzodioxolyl, pyridinyl, pyrrolyl, furanyl, thiophenyl, isoxazolyl, pyrazolyl, benzofuryl, [2,3-dihydro]benzofuryl, benzoxazolyl, quinoxalinyl.

The term "cycloalkyl" refers to alkyl groups having a monocyclic ring, bicyclic or multiple fused alkyl rings; such cycloalkyl rings include e.g. cyclopropyl, cyclobutyl, cyclopentyl; cyclohexyl, cycloheptyl, cyclooctyl; and the like; such multiple ring structures include e.g. adamantanyl; and bicyclo[2.2.1]heptane. "$C_3$-$C_8$", "$C_3$-$C_{10}$" etc. refers to the cycle size of the corresponding cycloalkyl.

The term "heterocycloalkyl" means a non-aromatic monocyclic or polycyclic ring comprising carbon and hydrogen atoms and at least one heteroatom selected from nitrogen, oxygen, and sulfur. "$C_3$-$C_8$"-heterocycloalkyl, "$C_3$-$C_{10}$" etc. refers to the size of the corresponding heterocycloalkyl. Particular examples of heterocycloalkyl groups include e.g. tetrahydrofuranyl, tetrahydro-2H-pyranyl, morpholinyl, pyrrolidinyl, piperidinyl, 2-oxopyrrolidinyl, piperazinyl.

The term "halogen" refers to Br, Cl, I, F.

The term "cyano" refers to a —C≡N group.

The term "perfluoro $C_1$-$C_6$-alkyl" refers to a $C_1$-$C_6$-alkyl group wherein each hydrogen atom has been replaced by a fluoro atom.

The term "amino" refers to a —NRR' group wherein R and R' are each independently selected from a) hydrogen, b) $C_1$-$C_6$-alkyl optionally substituted with hydroxy, $C_1$-$C_6$-alkoxy, c) heteroaryl-$C_1$-$C_6$-alkyl wherein the heteroatom is O, d) acylamino-$C_1$-$C_6$-alkyl, e) —C(O)OC$_1$-$C_6$-alkyl.

The term "acyl" refers to a group —C(O)R wherein R is H, $C_1$-$C_6$-alkyl or phenyl.

The term "amido" refers to a group —C(O)—NRR' wherein R and R' are independently H or $C_1$-$C_6$-alkyl, and may form a cycle with the N to which they are attached.

The term "$C_1$-$C_6$-alkylamino" refers to a $C_1$-$C_6$-alkyl group attached to the parent molecular group through an amino.

The term "amino-$C_1$-$C_6$-alkyl" refers to an amino group attached to the parent molecular group through a $C_1$-$C_6$-alkyl wherein the amino group is selected from —NH$_2$, —NHC$_1$-$C_6$-alkyl, and —N($C_1$-$C_6$-alkyl)$_2$ wherein the two substituents $C_1$-$C_6$-alkyl can be the same or different, and wherein the two substitutents may form a 3 to 8-membered heterocycloalkyl with the N to which they are attached to and which heterocycloalkyl may be optionally substituted with $C_1$-$C_6$-alkyl.

The term "alkyloxy" or "alkoxy" refers to the group —OR (e.g methoxy, ethoxy) wherein R is alkyl.

The term "cycloalkyl-oxy" or "cycloalkoxy" refers to a group —O—R (e.g cyclohexyloxy) wherein R is a cycloalkyl.

The term "cycloalkyl-sulfanyl" refers to a group —S—R (e.g cyclohexylsulfanyl) wherein R is a cycloalkyl.

The term "cycloalkyl-$C_1$-$C_6$-alkyl" refers to a cycloalkyl group attached to the parent molecular group through a $C_1$-$C_6$-alkyl.

The term "aryl-$C_1$-$C_6$-alkyl" refers to an aryl group attached to the parent molecular group through a $C_1$-$C_6$-alkyl (e.g. benzyl).

The term "aryl-$C_1$-$C_6$-alkyloxy" refers to a —O—R group wherein R is aryl $C_1$-$C_6$-alkyl (e.g. benzyloxy).

The term "heteroaryl-$C_1$-$C_6$-alkyl" refers to a heteroaryl group attached to the parent molecular group through a $C_1$-$C_6$alkyl.

The term "—C(O)O alkyl" or "alkoxycarbonyl" refers to a group C(O)—O—R wherein R is a $C_1$-$C_6$-alkyl.

The term carboxylic acid refers to a —COOH.

The term "hydroxy-$C_1$-$C_6$-alkyl" refers to a $C_1$-$C_6$-alkyl substituted by a hydroxyl.

The term "heterocycloalkyl-$C_1$-$C_6$-alkyl" refers to a heterocycloalkyl group attached to the parent molecular group through a $C_1$-$C_6$-alkyl.

The term "halogen-aryl" refers to a group aryl (e.g phenyl) substituted by a halogen (e.g. 4-chloro-phenyl, 3-iodo-phenyl, 4-fluoro-phenyl, 4-bromo-phenyl, 3-chloro-phenyl, 2-bromo-phenyl).

The term "$C_1$-$C_6$-alkyl-sulfonyl" refers to a group —S(O)$_2$—R wherein R is $C_1$-$C_6$-alkyl.

The term "acylamino-$C_1$-$C_6$-alkyl" refers to an acylamino group attached to the parent molecular group through a $C_1$-$C_6$-alkyl.

The term "acylamino" refers to a group —NH-acyl group which may also be defined as —NHC(O)R wherein R is a $C_1$-$C_6$-alkyl.

The above defined residues can be substituted or unsubstituted; the term "unsubstituted or substituted" or "optionally substituted" means that unless otherwise constrained by the definition of the individual substituent, the above set out groups, like "alkyl", "alkenyl", "alkynyl", "aryl", "heteroaryl", "cycloalkyl", "heterocycloalkyl" etc. can be substituted with at least one substituent selected from the group consisting of "$C_1$-$C_6$-alkyl", "$C_2$-$C_6$-alkenyl", "$C_2$-$C_6$-alkynyl", "cyclo alkyl", "hetero cyclo alkyl", "$C_1$-$C_6$-alkyl aryl", "$C_1$-$C_6$-alkyl hetero aryl", "$C_1$-$C_6$-alkyl cyclo alkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "—C(O)OC$_1$-$C_6$-alkyl", "heteroaryl", "sulfonyl", "alkoxy", in particular "$C_1$-$C_6$-alkoxy", "sulfanyl", "halogen", "carboxy", "trihalomethyl", "cyano", "hydroxy", "mercapto", "nitro", "halogen-aryl", "lactam", in particular "γ-lactam" or "δ-lactam", and the like.

"Pharmaceutically acceptable salts or complexes" refer to salts or complexes of the compounds disclosed herein. Examples of such salts include, but are not limited to, salts which are formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, methane sulfonic acid, naphthalene disulfonic acid, and poly-galacturonic acid, as well as salts formed with basic amino acids such as lysine or arginine.

Additionally, salts of compounds containing a carboxylic acid or other acidic functional group(s) can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

According to one aspect of the invention, are provided triazolopyridine compounds according to Formula (I):

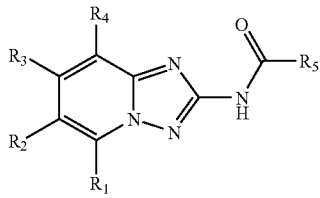

Formula (I)

wherein
$R_1$ is selected from
a. hydrogen;
b. $C_1$-$C_6$-alkyl;
c. $C_2$-$C_6$-alkenyl optionally substituted with $C_1$-$C_6$-alkyl;
d. —$NR_6R_7$;
e. $C_3$-$C_8$-cycloalkoxy, $C_1$-$C_6$-alkoxy;
f. $C_3$-$C_8$-cycloalkyl sulfanyl, $C_1$-$C_6$-alkyl sulfanyl; and
g. 5 or 6-membered heteroaryl having at least one heteroatom selected from N, S and O, said heteroaryl being optionally substituted with $C_1$-$C_6$ alkyl, halogen, or $C_1$-$C_6$ alkoxy;
$R_2$ is selected from
a. hydrogen;
b. halogen;
c. aryl optionally substituted with $R_{10}$, $R_{11}$ and/or $R_{12}$; and
d. 5 to 10-membered heteroaryl having at least one heteroatom selected from N, S and O and optionally substituted with $C_1$-$C_6$ alkyl;
or $R_1$ and $R_2$ taken together form a —C=C—C=C— group-;
$R_3$ is selected from
a. hydrogen;
b. halogen; and
c. $C_1$-$C_6$-alkyl optionally substituted with at least one fluoro;
$R_4$ is selected from
a. hydrogen; and
b. 5 or 6-membered heteroaryl having at least one heteroatom selected from N, S and O;
$R_5$ is selected from
a. $C_1$-$C_6$-alkyl optionally substituted with at least one of the following groups
  i. alkoxycarbonyl,
  ii. $C_1$-$C_6$-alkoxy,
  iii. —NC(O)R' wherein R' is aryl optionally substituted with $C_1$-$C_6$-alkyl,
  iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$-cycloalkyl optionally substituted with phenyl;
e. 3 to 8-membered heterocycloalkyl having a heteroatom selected from N, S and O optionally substituted with an acyl group;
f. aryl optionally substituted with at least one of the following groups
  i. $C_1$-$C_6$-alkyl,
  ii. perfluoro-$C_1$-$C_6$-alkyl,
  iii. at least one $C_1$-$C_6$-alkoxy optionally substituted with $C_1$-$C_6$-alkoxy carbonyl,
  iv. phenyl,
  v. $C_1$-$C_6$-alkyl sulfonyl,
  vi. —NHC(O)$C_1$-$C_6$-alkyl,
  vii. amino-$C_1$-$C_6$-alkyl wherein amino is selected from —$NH_2$, —NH$C_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy;
  viii. —N($C_1$-$C_6$-alkyl)($C_1$-$C_6$-alkoxy-$C_1$-$C_6$-alkyl),
  ix. 5 to 6-membered heterocycloalkyl-$C_1$-$C_6$-alkyl having a heteroatom selected from N and O;
  x. amido-$C_1$-$C_6$-alkyl,
  xi. $C_1$-$C_6$-alkoxy,
  xii. halogen;
g. 5 to 10-membered heteroaryl having at least one heteroatom selected from N, O or S optionally substituted with halogen; and
h. pyridinyl optionally substituted with at least one of the following groups
  i. halogen,
  ii. $C_1$-$C_6$-alkyl,
  iii. amino-$C_1$-$C_6$-alkyl wherein amino is selected from —$NH_2$, —NH$C_1$-$C_6$-alkyl or —N($C_1$-$C_6$-alkyl)$_2$, wherein the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or hydroxy;
  iv. —NH(hydroxy-$C_1$-$C_6$-alkyl),
  v. —NH-(5-membered heteroaryl-$C_1$-$C_6$-alkyl having as heteroatom O),
  vi. 5 or 6-membered heterocycloalkyl-$C_1$-$C_6$-alkyl having at least one heteroatom selected from O and N;
  vii. 5 or 6-membered heterocycloalkyl having at least one heteroatom selected from O and N optionally substituted with hydroxy, —C(O)OR' wherein R' is $C_1$-$C_6$-alkyl, halogen or $C_1$-$C_6$-alkyl;
  viii. amino;
  ix. —NH(amino-$C_1$-$C_6$-alkyl);
  x. —N($C_1$-$C_6$-alkyl)$_2$;
$R_6$ is selected from
a. $C_1$-$C_6$-alkyl optionally substituted with one or two hydroxy groups,
b. phenyl optionally substituted with at least one of the following groups
  i. halogen
  ii. $C_1$-$C_6$-alkyl, or
  iii. $C_1$-$C_6$-alkoxy;
c. 5 or 6-membered heterocycloalkyl having a heteroatom selected from O and N optionally substituted with $C_1$-$C_6$-alkyl;
d. $C_3$-$C_8$-cycloalkyl optionally substituted with $R_8$; and
e. —(CH$_2$)$R_9$ wherein n equals 1, 2 or 3;
$R_7$ is
a. hydrogen or
b. $C_1$-$C_6$-alkyl;
or $R_6$ and $R_7$ can form a 3 to 8-membered heterocycloalkyl with the N to which they are attached to and wherein the heterocycloalkyl is optionally substituted with $C_1$-$C_6$-alkyl;
$R_8$ is selected from
a. hydrogen;
b. hydroxy;

c. $C_1$-$C_6$-alkyl optionally substituted with hydroxy;
d. C(O)O—$C_1$-$C_6$-alkyl; and
e. —$NH_2$;

$R_9$ is selected from
a. $C_3$-$C_8$-cycloalkyl optionally substituted with an unsubstituted $C_1$-$C_6$-alkyl;
b. 5 or 6-membered heterocycloalkyl having a heteroatom selected from N and O optionally substituted with $C_1$-$C_6$-alkyl;
c. 5 or 6-membered heteroaryl having a heteroatom selected from N and O optionally substituted with $C_1$-$C_6$-alkyl;
d. phenyl;

$R_{10}$, $R_{11}$ and $R_{12}$ are each independently selected from
a. hydrogen;
b. halogen;
c. hydroxy;
d. $C_1$-$C_6$-alkyl;
e. $C_1$-$C_6$-alkoxy;
f. cyano;
g. —C(o)NH($C_1$-$C_6$-alkyl)amino wherein the amino is —N($CH_3$)$_2$); and
h. —$NH_2$.

Any of the above chemical groups can be optionally substituted.

The compounds according to the invention advantageously inhibit ASK, preferably ASK1. The inventors could achieve good $IC_{50}$ values by the particular design of the compounds according to the invention.

The $IC_{50}$ value of the compounds of the invention measured according to the procedure as outlined in the experiments is 30 µM or less, preferably 20 µM or less, more preferably 15 µM or less, even more preferably 10 µM or less, still more preferably 5 µM or less, and more preferably 1 µM or less.

It was found by the inventors that by refining the design of the compounds in particular positions with a selection of chemical groups as will be evident from the below description advantageous $IC_{50}$ values in the nanomolar range could be achieved. Preferred compounds of the invention exhibit an $IC_{50}$ value of, e.g. 900 nM or less, 700 nM or less, 500 nM or less, 200 nM or less, 100 nM or less, 50 nM or less.

The compounds according to the invention are also characterized by their positive inhibitory effect in the Lipopolysaccharide (LPS)-induced INFα release assay in mice as described in the below experimental section. Preferably the compounds of the invention exhibit an inhibition of 30% or more, preferably 40% or more, and more preferably 50% or more.

The dosage of a compound according to the invention applied in this assay is usually between 10 and 80 mg/kg body weight. Another dosage that may be used is between 20 and 60, preferably between 30 and 40 mg/kg.

Other in vitro and in vivo assays known to the person skilled in the art may be applied to show the positive effects of the compounds of the invention and their relevance for various diseases. These models are apparent and well known to the person skilled in the field.

In the following, compounds and compound groups according to the invention are described characterized by particular structural and functional features. Each of these compound groups exhibits also properties making them useful for particular applications, e.g. particular medical indications, which will be evident by normal experimentation available to the skilled person.

In one embodiment the invention relates to a triazolopyridine compound according to Formula I wherein $R_1$ is selected from
a. hydrogen;
b. $C_1$-$C_6$-alkyl;
c. $C_2$-$C_6$-alkenyl optionally substituted with $C_1$-$C_6$-alkyl;
d. —$NR_6R_7$;
e. $C_3$-$C_8$-cycloalkoxy;
f. $C_3$-$C_8$-cycloalkyl sulfanyl; and
g. 5 or 6-membered heteroaryl having at least one heteroatom selected from N, S and O optionally substituted with $C_1$-$C_6$-alkyl;

$R_2$ is selected from
a. hydrogen;
b. Cl or Br;
c. aryl optionally substituted with $R_{10}$, $R_{11}$ and/or $R_{12}$; and
d. 5, 6 or 9-membered heteroaryl having at least one heteroatom selected from N, S and O and optionally substituted with $C_1$-$C_6$ alkyl;

or $R_1$ and $R_2$ taken together form a —C=C—C=C— group-;

$R_3$ is selected from
a. hydrogen;
b. chloro; bromo;
c. methyl; and
d. $CF_3$;

$R_4$ is selected from
a. hydrogen; and
b. furanyl;

$R_5$ is selected from
a. $C_1$-$C_6$-alkyl optionally substituted with at least one of the following groups
   i. alkoxycarbonyl,
   ii. $C_1$-$C_6$-alkoxy,
   iii. —NHC(O)R' wherein R' is aryl optionally substituted with $C_1$-$C_6$-alkyl,
   iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$ cycloalkyl optionally substituted with phenyl;
e. 3 to 8-membered heterocycloalkyl having a heteroatom selected from N, S and O optionally substituted with an acyl group;
f. aryl optionally substituted with at least one of the following groups
   i. $C_1$-$C_6$-alkyl,
   ii. perfluoro-$C_1$-$C_6$-alkyl,
   iii. at least one $C_1$-$C_6$-alkoxy optionally substituted with $C_1$-$C_6$-alkoxy carbonyl,
   iv. phenyl,
   v. $C_1$-$C_6$-alkyl sulfonyl,
   vi. —NC(O)$C_1$-$C_6$-alkyl,
   vii. amino-$C_1$-$C_6$-alkyl wherein amino is selected from —$NH_2$, —NH$C_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy,
   viii. —N($C_1$-$C_6$-alkyl)($C_1$-$C_6$-alkoxy-$C_1$-$C_6$-alkyl),
   ix. 5 to 6-membered heterocycloalkyl-$C_1$-$C_6$-alkyl having a heteroatom selected from N and O,
   x. amido-$C_1$-$C_6$-alkyl,
   xi. $C_1$-$C_6$-alkoxy,
   xii. halogen;

g. 5 to 10-membered heteroaryl having at least one heteroatom selected from N optionally substituted with halogen; and
h. pyridinyl optionally substituted with at least one of the following groups
  i. halogen,
  ii. $C_1$-$C_6$-alkyl optionally substituted with a 5 or 6-membered heterocycloalkyl having at least one heteroatom selected from O and N,
  iii. 5 or 6-membered heterocycloalkyl having at least one heteroatom selected from O and N,
  iv. —NH(hydroxy-$C_1$-$C_6$-alkyl),
  v. —NH-(5-membered heteroaryl-$C_1$-$C_6$-alkyl having as heteroatom O),
  vi. 5 or 6-membered heterocycloalkyl-$C_1$-$C_6$-alkyl having at least one heteroatom selected from O and N;
  vii. 5 or 6-membered heterocycloalkyl having at least one heteroatom selected from O and N optionally substituted with hydroxy, —C(O)OR' wherein R' is $C_1$-$C_6$-alkyl, halogen or $C_1$-$C_6$-alkyl,
  viii. amino,
  ix. —NH(amino-$C_1$-$C_6$-alkyl),
  x. —N($C_1$-$C_6$-alkyl)$_2$;
$R_6$ is selected from
a. $C_1$-$C_6$-alkyl optionally substituted with one or two hydroxy groups,
b. phenyl optionally substituted with at least one of the following groups
  i. halogen,
  ii. $C_1$-$C_6$-alkyl, or
  iii. $C_1$-$C_6$-alkoxy;
c. 5 or 6-membered heterocycloalkyl having a heteroatom selected from O and N optionally substituted with is $C_1$-$C_6$-alkyl;
d. $C_3$-$C_8$-cycloalkyl optionally substituted with $R_8$; and
e. —(CH$_2$)$_n$$R_9$ wherein n equals 1, 2 or 3;
$R_7$ is
a. hydrogen or
b. $C_1$-$C_6$-alkyl; or
or $R_6$ and $R_7$ can form a 3 to 8-membered heterocycloalkyl with the N to which they are attached to and wherein the heterocycloalkyl is optionally substituted with $C_1$-$C_6$-alkyl;
$R_8$ is selected from
a. hydrogen;
b. hydroxy;
c. unsubstituted or substituted $C_1$-$C_6$-alkyl wherein the substituent is hydroxyl;
d. C(O)O—$C_1$-$C_6$-alkyl; and
e. —NH$_2$;
$R_9$ is selected from
a. $C_3$-$C_8$-cycloalkyl optionally substituted with an unsubstituted $C_1$-$C_6$-alkyl;
b. 5 or 6-membered heterocycloalkyl having a heteroatom selected from N and O optionally substituted with $C_1$-$C_6$-alkyl;
c. 5 or 6-membered heteroaryl having a heteroatom selected from N and O optionally substituted with $C_1$-$C_6$-alkyl; and
d. phenyl.
$R_{10}$, $R_{11}$ and $R_{12}$ are each independently selected from
a. hydrogen;
b. fluoro, bromo;
c. hydroxyl;
d. $C_1$-$C_6$-alkyl;
e. $C_1$-$C_6$-alkoxy;
f. cyano;
g. —C(o)NH($C_1$-$C_6$-alkyl)amino wherein the amino is —N(CH$_3$)$_2$); and
h. —NH$_2$.

In another embodiment the invention relates to triazolopyridine compounds according to the following Formula I-1

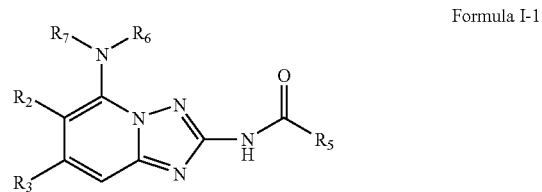

Formula I-1 wherein
$R_2$ is hydrogen or bromo;
$R_3$ is selected from
a. hydrogen;
b. halogen; and
c. $C_1$-$C_6$-alkyl optionally substituted with at least one fluoro;
$R_5$ is selected from
a. $C_1$-$C_6$-alkyl optionally substituted with at least one of the following groups
  i. $C_1$-$C_6$-alkoxycarbonyl,
  ii. $C_1$-$C_6$-alkoxy,
  iii. —NHC(O)R' wherein R' is aryl optionally substituted with $C_1$-$C_6$-alkyl,
  iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$ cycloalkyl optionally substituted with phenyl;
e. 3 to 8-membered heterocycloalkyl having a heteroatom selected from N, S and O optionally substituted with an acyl group;
f. aryl optionally substituted with
  i. $C_1$-$C_6$-alkyl optionally substituted with a γ-lactam or δ-lactam,
  ii. perfluoro-$C_1$-$C_6$-alkyl,
  iii. at least one $C_1$-$C_6$-alkoxy optionally substituted with $C_1$-$C_6$-alkoxycarbonyl,
  iv. phenyl,
  v. $C_1$-$C_6$-alkyl sulfonyl,
  vi. —NHC(O)$C_1$-$C_6$-alkyl,
  vii. amino-$C_1$-$C_6$-alkyl wherein amino is selected from —NH$_2$, —NHC$_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy,
  viii. —N($C_1$-$C_6$-alkyl)($C_1$-$C_6$-alkoxy-$C_1$-$C_6$-alkyl),
  ix. 5 to 6-membered heterocycloalkyl-$C_1$-$C_6$-alkyl having a heteroatom selected from N and O,
  x. amido-$C_1$-$C_6$-alkyl,
  xi. $C_1$-$C_6$-alkoxy,
  xii. halogen;
g. 5 to 10-membered heteroaryl having at least one heteroatom selected from N optionally substituted with halogen; and h. pyridinyl optionally substituted with at least one of the following groups
  i. halogen,
  ii. $C_1$-$C_6$-alkyl optionally substituted with a 5 or 6-membered heterocycloalkyl having at least one heteroatom selected from O and N,
  iii. 5 or 6-membered heterocycloalkyl having at least one heteroatom selected from O and N,
  iv. —NH(hydroxy-$C_1$-$C_6$-alkyl),
  v. —NH-(5-membered heteroaryl-$C_1$-$C_6$-alkyl having as heteroatom O),
  vi. 5 or 6-membered heterocycloalkyl-$C_1$-$C_6$-alkyl having at least one heteroatom selected from O and N;
$R_6$ is selected from
a. $C_1$-$C_6$-alkyl optionally substituted with one or two hydroxy groups,
b. phenyl optionally substituted with at least one of the following groups
  i. halogen,
  ii. $C_1$-$C_6$-alkyl,
  iii. $C_1$-$C_6$-alkoxy;
c. 5 or 6-membered heterocycloalkyl having a heteroatom selected from O and N optionally substituted with is $C_1$-$C_6$-alkyl;
d. $C_3$-$C_8$-cycloalkyl optionally substituted with $R_8$; and
e. —$(CH_2)_n R_9$ wherein n equals 1, 2 or 3;
$R_7$ is
a. hydrogen or
b. $C_1$-$C_6$-alkyl.

In another embodiment the invention relates to triazolopyridine compounds according to the following Formula I-2

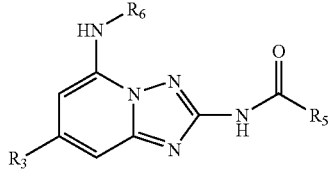

Formula I-2 wherein
$R_3$ is selected from
a. hydrogen;
b. halogen; and
c. $C_1$-$C_6$-alkyl optionally substituted with at least one fluoro;
$R_5$ is selected from
a. $C_1$-$C_6$-alkyl optionally substituted with at least one of the following groups
  i. $C_1$-$C_6$-alkoxycarbonyl,
  ii. $C_1$-$C_6$-alkoxy,
  iii. —NHC(O)R' wherein R' is aryl optionally substituted with $C_1$-$C_6$-alkyl,
  iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$ cycloalkyl optionally substituted with phenyl;
e. 3 to 8-membered heterocycloalkyl having a heteroatom selected from N, S and O optionally substituted with an acyl group;
f. aryl optionally substituted with
  i. $C_1$-$C_6$-alkyl optionally substituted with a γ-lactam or δ-lactam,
  ii. perfluoro-$C_1$-$C_6$-alkyl,
  iii. at least one $C_1$-$C_6$-alkoxy optionally substituted with $C_1$-$C_6$-alkoxycarbonyl,
  iv. phenyl,
  v. $C_1$-$C_6$-alkyl sulfonyl,
  vi. —NHC(O)$C_1$-$C_6$-alkyl,
  vii. amino-$C_1$-$C_6$-alkyl wherein amino is selected from —$NH_2$, —NH$C_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy;
  viii. —N($C_1$-$C_6$-alkyl)($C_1$-$C_6$-alkoxy-$C_1$-$C_6$-alkyl),
  ix. 5 to 6-membered heterocycloalkyl-$C_1$-$C_6$-alkyl having a heteroatom selected from N and O;
  x. amido-$C_1$-$C_6$-alkyl,
  xi. $C_1$-$C_6$-alkoxy,
  xii. halogen;
g. 5 to 10-membered heteroaryl having at least one heteroatom selected from N optionally substituted with halogen; and
h. pyridinyl optionally substituted with at least one of the following groups
  i. halogen,
  ii. $C_1$-$C_6$-alkyl optionally substituted with a 5 or 6-membered heterocycloalkyl having at least one heteroatom selected from O and N,
  iii. 5 or 6-membered heterocycloalkyl having at least one heteroatom selected from O and N,
  iv. —NH(hydroxy-$C_1$-$C_6$-alkyl),
  v. —NH-(5-membered heteroaryl-$C_1$-$C_6$-alkyl having as heteroatom O),
  vi. 5 or 6-membered heterocycloalkyl-$C_1$-$C_6$-alkyl having at least one heteroatom selected from O and N;
$R_6$ is selected from
a. $C_1$-$C_6$-alkyl optionally substituted with one or two hydroxy groups,
b. phenyl optionally substituted with at least one of the following groups
  i. halogen
  ii. $C_1$-$C_6$-alkyl,
  iii. $C_1$-$C_6$-alkoxy;
c. 5 or 6-membered heterocycloalkyl having a heteroatom selected from O and N optionally substituted with is $C_1$-$C_6$-alkyl;
d. $C_3$-$C_8$-cycloalkyl optionally substituted with $R_8$; and
e. —$(CH_2)_n R_9$ wherein n equals 1, 2 or 3.
$R_8$ and $R_9$ are as above defined.
Compounds according to Formula I-2 as defined above exhibit an $IC_{50}$ of 20 μM or less, preferably 15 μM or less, more preferably 10 μM or less, even more preferably 5 μM or less and even more preferably 1 μM or less.
Preferred embodiments of the above Formula I-2 are:
1. wherein $R_3$ is Cl, Br, —$CH_3$ or —$CF_3$;
2. wherein $R_3$ is Cl, Br, —$CH_3$ or —$CF_3$.
$R_5$ is selected from
a. phenyl optionally substituted with at least one of the following groups
  i. $C_1$-$C_6$-alkyl,
  ii. at least one $C_1$-$C_6$-alkoxy optionally substituted with $C_1$-$C_6$-alkoxy carbonyl,
  iii. —NHC(O)$C_1$-$C_6$-alkyl,
  iv. —N($C_1$-$C_6$-alkyl)$_2$, v. 5 to 6-membered heterocycloalkyl-$C_1$-$C_6$-alkyl having a heteroatom selected from N and O optionally substituted with $C_1$-$C_6$-alkyl, halogen or $C_1$-$C_6$-alkoxy
vi. $C_1$-$C_6$-alkoxy,
vii. halogen; and
b. pyridinyl optionally substituted with at least one of the following groups
 i. $C_1$-$C_6$-alkyl optionally substituted with a 5 or 6-membered heterocycloalkyl having at least one heteroatom selected from O and N,
 ii. 5 or 6-membered heterocycloalkyl having at least one heteroatom selected from O and N,
 iii. —NH-(5-membered heteroaryl-$C_1$-$C_6$-alkyl having as heteroatom O),
 iv. 5 or 6-membered heterocycloalkyl-$C_1$-$C_6$-alkyl having at least one heteroatom selected from O and N;
$R_6$ is selected from
a. unsubstituted $C_1$-$C_6$-alkyl,
b. phenyl optionally substituted with at least one of the following groups
 i. halogen, preferably F, Cl,
 ii. $C_1$-$C_6$-alkyl,
 iii. $C_1$-$C_6$-alkoxy,
c. 6-membered heterocycloalkyl having a heteroatom selected from O and N optionally substituted with $C_1$-$C_6$-alkyl;
d. $C_3$-$C_8$-cycloalkyl optionally substituted with $C_1$-$C_6$-alkyl.
3. wherein $R_3$ is Cl, Br, —$CH_3$ or —$CF_3$;
$R_5$ is selected from
a. phenyl optionally substituted with amino-$C_1$-$C_6$-alkyl wherein amino is selected from
 i. —$NH_2$,
 ii. —$NHC_1$-$C_6$-alkyl,
 iii. —$N(C_1$-$C_6$-alkyl$)_2$, and
 iv. 5 or 6-membered heterocycloalkyl having as heteroatom N or O;
b. pyridinyl;
c. and pyridin-$C_1$-$C_6$-alkyl;
$R_6$ is selected from
a. $C_1$-$C_6$-alkyl optionally substituted with
 i. hydroxy, or
 ii. $C_1$-$C_6$-alkoxy;
b. $C_3$-$C_8$-cycloalkyl;
c. $CH_2R_9$ wherein $R_9$ is $C_3$-$C_6$-cycloalkyl.

These preferred embodiments of the invention preferably exhibit an $IC_{50}$ of 5 μM or less, preferably 1 μM or less, more preferably 0.9 μM or less, even more preferably 0.5 μM or less, even more preferably 0.3 μM or less and still preferably 0.1 μM or less.

In another embodiment the invention relates to triazolopyridine compounds according to the following Formula I-3

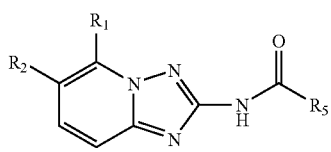

Formula I-3 wherein
$R_1$ is selected from
a. hydrogen;
b. unsubstituted $C_1$-$C_6$-alkyl;
c. $C_2$-$C_6$-alkenyl optionally substituted with $C_1$-$C_6$-alkyl;
d. —$NR_6R_7$;
e. unsubstituted $C_3$-$C_8$-cycloalkoxy;
f. unsubstituted $C_3$-$C_8$-cycloalkyl sulfanyl; and
g. 5 or 6 membered heteroaryl having at least one heteroatom selected from N, S and O optionally substituted with $C_1$-$C_6$ alkyl;
$R_2$ is hydrogen or bromo;
$R_5$ is selected from
a. $C_1$-$C_6$-alkyl optionally substituted with at least one of the following groups
 i. $C_1$-$C_6$-alkoxycarbonyl,
 ii. $C_1$-$C_6$-alkoxy,
 iii. —NHC(O)R' wherein R' is aryl optionally substituted with $C_1$-$C_6$-alkyl,
 iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$ cycloalkyl optionally substituted with phenyl;
e. 3 to 8-membered heterocycloalkyl having a heteroatom selected from N, S and O optionally substituted with an acyl group;
f. aryl optionally substituted with
 i. $C_1$-$C_6$-alkyl optionally substituted with a γ-lactam or δ-lactam,
 ii. perfluoro-$C_1$-$C_6$-alkyl,
 iii. at least one $C_1$-$C_6$-alkoxy optionally substituted with $C_1$-$C_6$-alkoxycarbonyl,
 iv. phenyl,
 v. $C_1$-$C_6$-alkyl sulfonyl,
 vi. —NHC(O)$C_1$-$C_6$-alkyl,
 vii. amino-$C_1$-$C_6$-alkyl wherein amino is selected from —$NH_2$, —$NHC_1$-$C_6$-alkyl, —$N(C_1$-$C_6$-alkyl$)_2$, $N(C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy,
 viii. —$N(C_1$-$C_6$-alkyl)($C_1$-$C_6$-alkoxy-$C_1$-$C_6$-alkyl),
 ix. 5 to 6-membered heterocycloalkyl-$C_1$-$C_6$-alkyl having a heteroatom selected from N and O,
 x. amido-$C_1$-$C_6$-alkyl,
 xi. $C_1$-$C_6$-alkoxy,
 xii. halogen;
g. 5 to 10-membered heteroaryl having at least one heteroatom selected from N optionally substituted with halogen; and
h. pyridinyl optionally substituted with at least one of the following groups
 i. halogen,
 ii. $C_1$-$C_6$-alkyl optionally substituted with a 5 or 6-membered heterocycloalkyl having at least one heteroatom selected from O and N,
 iii. 5 or 6-membered heterocycloalkyl having at least one heteroatom selected from O and N,
 iv. —NH(hydroxy-$C_1$-$C_6$-alkyl),
 v. —NH-(5-membered heteroaryl-$C_1$-$C_6$-alkyl having as heteroatom O),
 vi. 5 or 6-membered heterocycloalkyl-$C_1$-$C_6$-alkyl having at least one heteroatom selected from O and N.

In another embodiment the invention relates to triazolopyridine compounds according to the following Formula I-4

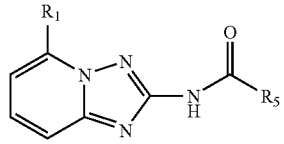

Formula I-4 wherein
$R_1$ is selected from
a. unsubstituted $C_1$-$C_6$-alkyl;
b. $C_2$-$C_6$-alkenyl optionally substituted with $C_1$-$C_6$-alkyl;
c. —$NR_6R_7$;
d. unsubstituted $C_3$-$C_8$-cycloalkoxy;
e. unsubstituted $C_3$-$C_8$-cycloalkyl sulfanyl; and
f. 5 or 6 membered heteroaryl having at least one heteroatom selected from N, S and O optionally substituted with $C_1$-$C_6$ alkyl;
$R_5$ is selected from
a. $C_1$-$C_6$-alkyl optionally substituted with at least one of the following groups
  i. $C_1$-$C_6$-alkoxycarbonyl,
  ii. $C_1$-$C_6$-alkoxy,
  iii. —NHC(O)R' wherein R' is aryl optionally substituted with $C_1$-$C_6$-alkyl,
  iv. benzyloxy;
b. aryl-$C_1$-$C_6$-alkyl;
c. 5 or 6-membered heteroaryl-$C_1$-$C_6$-alkyl having a heteroatom selected from N, S and O optionally substituted with $C_1$-$C_6$-alkyl, halogen or $C_1$-$C_6$-alkoxy;
d. $C_3$-$C_6$ cycloalkyl optionally substituted with phenyl;
e. 3 to 8-membered heterocycloalkyl having a heteroatom selected from N, S and O optionally substituted with an acyl group;
f. aryl optionally substituted with
  i. $C_1$-$C_6$-alkyl optionally substituted with a γ-lactam or δ-lactam,
  ii. perfluoro-$C_1$-$C_6$-alkyl,
  iii. at least one $C_1$-$C_6$-alkoxy optionally substituted with $C_1$-$C_6$-alkoxycarbonyl,
  iv. phenyl,
  v. $C_1$-$C_6$-alkyl sulfonyl,
  vi. —NHC(O)$C_1$-$C_6$-alkyl,
  vii. amino-$C_1$-$C_6$-alkyl wherein amino is selected from —$NH_2$, —$NHC_1$-$C_6$-alkyl, —$N(C_1$-$C_6$-alkyl)$_2$, $N(C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached to and wherein the heterocycloalkyl is optionally substituted with $C_1$-$C_6$-alkyl or with hydroxy,
  viii. —$N(C_1$-$C_6$-alkyl)($C_1$-$C_6$-alkoxy-$C_1$-$C_6$-alkyl),
  ix. 5 to 6-membered heterocycloalkyl-$C_1$-$C_6$-alkyl having a heteroatom selected from N and O,
  x. amido-$C_1$-$C_6$-alkyl,
  xi. $C_1$-$C_6$-alkoxy,
  xii. halogen;
g. 5 to 10-membered heteroaryl having at least one heteroatom selected from N optionally substituted with halogen; and
h. pyridinyl optionally substituted with at least one of the following groups
  i. halogen,
  ii. $C_1$-$C_6$-alkyl optionally substituted with a 5 or 6-membered heterocycloalkyl having at least one heteroatom selected from O and N,
  iii. 5 or 6-membered heterocycloalkyl having at least one heteroatom selected from O and N,
  iv. —NH(hydroxy-$C_1$-$C_6$-alkyl),
  v. —NH-(5-membered heteroaryl-$C_1$-$C_6$-alkyl having as heteroatom O),
  vi. 5 or 6-membered heterocycloalkyl-$C_1$-$C_6$-alkyl having at least one heteroatom selected from O and N;

Preferably these compounds exhibit an $IC_{50}$ of 20 μM or less, preferably 15 μM or less, more preferably 10 μM or less, even more preferably 5 μM or less.

A preferred embodiment of the above Formula I-4 is where
$R_1$ is an unsubstituted 5-membered heteroaryl having at least one heteroatom selected from O, S and N;
$R_5$ is selected from
a. phenyl optionally substituted with at least one of the following groups
  i. $C_1$-$C_6$-alkyl,
  ii. perfluoro-$C_1$-$C_6$-alkyl,
  iii. $C_1$-$C_6$-alkoxy;
  iv. $C_1$-$C_6$-alkoxy,
  v. halogen; and
b. pyridinyl optionally substituted with at least one of the following groups
  i. Cl,
  ii. Br,
  iii. —NH(hydroxy-$C_1$-$C_6$-alkyl).

Preferably these compounds exhibit an $IC_{50}$ of 15 μM or less, more preferably 10 μM or less, even more preferably 5 μM or less, even more preferably 1 μM or less, and still more preferably 0.9 μM or less.

In another embodiment the invention relates to triazolopyridine compounds according to the following Formula I-5

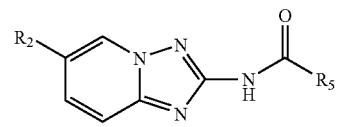

Formula I-5 wherein
$R_2$ is selected from
a. phenyl optionally substituted with
  i. at least one unsubstituted $C_1$-$C_6$-alkyl,
  ii. unsubstituted $C_1$-$C_6$-alkoxy,
  iii. fluoro,
  iv. bromo,
  v. hydroxy,
  vi. cyano, or
  vii. —$NH_2$; and
b. 5 or 9-membered heteroaryl having a heteroatom selected from N, S and O;
$R_5$ is selected from
a. unsubstituted $C_1$-$C_6$-alkyl;
b. aryl optionally substituted with
  i. amino-$C_1$-$C_6$-alkyl wherein amino is selected from —$NH_2$, —$NHC_1$-$C_6$alkyl or —$N(C_1$-$C_6$-alkyl)$_2$, and the two substituents $C_1$-$C_6$-alkyl may form a 3 to 8-membered heterocycloalkyl with the N to which they are attached to and wherein the heterocycloalkyl is optionally substituted with $C_1$-$C_6$-alkyl, or ii. 5 or 6-membered heterocycloalkyl-$C_1$-$C_6$-alkyl; and
c. pyridinyl optionally substituted with at least one of the following groups
  i. $C_1$-$C_6$-alkyl optionally substituted with a 5 or 6-membered heterocycloalkyl having at least one heteroatom selected from O and N,
  ii. 5 or 6-membered heterocycloalkyl having at least one heteroatom selected from O and N,
  iii. —NH-(5-membered heteroaryl-$C_1$-$C_6$-alkyl having as heteroatom O),
  iv. 5 or 6-membered heterocycloalkyl-$C_1$-$C_6$-alkyl having at least one heteroatom selected from O and N.

Preferably these compounds exhibit an $IC_{50}$ of 20 µM or less, more preferably 15 µM or less, even more preferably 10 µM or less, and even more preferably 5 µM or less.

A preferred embodiment of the above Formula I-5 is where $R_2$ is selected from
a. phenyl optionally substituted with at least one of the following groups
  i. at least one unsubstituted $C_1$-$C_6$-alkyl,
  ii. unsubstituted $C_1$-$C_6$-alkoxy,
  iii. fluoro,
  iv. bromo,
  v. hydroxy,
  vi. cyano
  vii. —$NH_2$;
b. furanyl; and
c. thienyl;
$R_5$ is selected from
a. unsubstituted $C_1$-$C_6$-alkyl;
b. phenyl optionally substituted with
  i. amino-$C_1$-$C_6$-alkyl wherein amino is selected from —$NH_2$, —$NHC_1$-$C_6$-alkyl or —$N(C_1$-$C_6$-alkyl$)_2$, or
  ii. 5 or 6-membered heterocycloalkyl-$C_1$-$C_6$-alkyl;
c. pyridinyl optionally substituted with at least one of the following groups
  i. $C_1$-$C_6$-alkyl optionally substituted with a 5 or 6-membered heterocycloalkyl having at least one heteroatom selected from O and N,
  ii. 5 or 6-membered heterocycloalkyl having at least one heteroatom selected from O and N,
  iii. —NH-(5-membered heteroaryl-$C_1$-$C_6$-alkyl having as heteroatom O),
  iv. 5 or 6-membered heterocycloalkyl-$C_1$-$C_6$-alkyl having at least one heteroatom selected from O and N.

Preferably these compounds exhibit an $IC_{50}$ of 20 µM or less, more preferably 15 µM or less, even more preferably 10 µM or less, even more preferably 5 µM or less, and even more preferably 1 µM or less.

In another embodiment the invention relates to triazolopyridine compounds according to the following Formula I-6

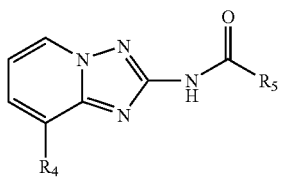

Formula I-6 wherein
$R_4$ is furanyl;
$R_5$ is selected from unsubstituted phenyl; and 5 or 6-membered heteroaryl having a heteroatom selected from N, S and O.

A preferred embodiment of the above Formula I-6 is wherein $R_5$ is selected from phenyl and 5-membered heteroaryl having a heteroatom selected from N, S and O.

In one embodiment $R_1$ is hydrogen; furanyl, preferably furan-2-yl, more preferably furan-3-yl; or —$NR_6R_7$; $R_2$ is hydrogen, or methoxy-hydroxy-phenyl, preferably 1H pyrazol-4-yl; $R_3$ is perfluoromethyl, Cl or Br; $R_4$ is hydrogen; $R_5$ is unsubstituted or substituted pyridine wherein the substituent is halogeno, preferably Cl or Br; dihydro-1,4-benzodioxin-6-yl, 3,5-bis (methoxy)phenyl; phenyl; or 4-(morpholin-4-yl methyl)phenyl; Either of $R_6$ and $R_7$ is hydrogen; cycloalkyl, preferably cyclopropyl, more preferably cyclohexyl; cyclohexyl $C_1$-$C_6$-alkyl; $C_1$-$C_6$-alkyl, preferably methyl, more preferably isobutyl, even more preferably isopropyl. The remaining chemical groups are as earlier defined.

These compounds according to the invention are preferably characterized by an $IC_{50}$ of 5 µM or less, preferably of 1 µM or less.

The embodiments of Formulae I-1, I-2, I-3, I-4, I-5 and I-6 and the embodiments thereof described as preferred may bear in further preferred embodiments at each chemical moiety substituents as described in the definitions regarding substituents above.

It was found by the inventors that the combination of these specific chemical groups leads to triazolopyridine compounds exhibiting very good inhibition properties to its target, i.e. the ASK target, in particular to ASK1.

One structure of the compounds according to the invention is characterized by cyclo alkyl, aryl or heteroaryl groups for $R_1$ or $R_2$ and $R_5$ wherein the remaining chemical groups are as defined above. Yet another structure is a substituted cycloalkyl, a substituted aryl or a substituted heteroaryl group for $R_1$ or $R_2$ and a substituted aryl or heteroaryl group for $R_5$ wherein the substituent is defined as above.

These structures of the compounds according to the invention exhibit good inhibition of the target ASK, in particular ASK1, which is obvious from the advantageous $IC_{50}$ values as exemplified in the experimental section below. Moreover, such compounds show positive results, i.e. inhibition, in in vivo assays as exemplified by the LPS-induced TNFα release assay.

In this assay it could be shown that compounds according to the invention as defined in this section characterized by the structural features as outlined above exhibit an in vivo inhibition of at least about 40%, preferably at least about 50%. Particularly good results could be achieved with compounds of the invention according to Formula I-3 and Formula I-4 that may achieve an in vivo inhibition of at least about 40%, preferably at least about 42%, more preferably at least about 45%, and even more preferably at least about 48%. A particular group of compounds is characterized by —$NR_6R_7$ with $R_6$ and $R_7$ as defined above or a 5 or 6 membered heteroaryl in position $R_1$ and a pyridinyl in position $R_5$ that exhibit an in vivo inhibition of at least about 43%, preferably at least about 48%.

The structural motif as described in the above section may even enhance the properties by additional groups such as —$CF_3$ or a halogen in positions $R_2$ or $R_3$.

In particular advantageous is a perfluoromethyl group for $R_3$ and/or a furanyl for $R_1$ and/or a pyridine for $R_5$. Such compounds are preferably characterized by positive $IC_{50}$ values of e.g. 10 µM or less, preferably 5 µM or less, preferably 1 µM or less, more preferably of 0.1 µM or less and even more preferably of 0.5 µM or less.

Advantageously, it was found by the inventors that the above characterized positions play a significant role in the positive inhibition effects of the inventive compounds to the target ASK.

The invention is further exemplified by the following triazolopyridine compounds:

N-[5-(3-furyl)[1,2,4]triazolo[1,5-a]pyridin-2-yl]-2-phenylacetamide;
N-[5-(3-furyl)[1,2,4]triazolo[1,5-a]pyridin-2-yl]nicotinamide;
N-[5-(3-furyl)[1,2,4]triazolo[1,5-a]pyridin-2-yl]-4-(trifluoromethyl)benzamide;
ethyl 3-{[5-(3-furyl)[1,2,4]triazolo[1,5-a]pyridin-2-yl]amino}-3-oxopropanoate;
N-[5-(3-furyl)[1,2,4]triazolo[1,5-a]pyridin-2-yl]-2-methoxyacetamide;
6-chloro-N-[5-(3-furyl)[1,2,4]triazolo[1,5-a]pyridin-2-yl]nicotinamide;
methyl 4-{[5-(3-furyl)[1,2,4]triazolo[1,5-a]pyridin-2-yl]amino}-4-oxobutanoate;
2-(benzyloxy)-N-[5-(3-furyl)[1,2,4]triazolo[1,5-a]pyridin-2-yl]acetamide;
3-methoxy-N-[5-(1H-pyrrol-2-yl)[1,2,4]triazolo[1,5-a]pyridin-2-yl]benzamide;
N-[5-(1H-pyrrol-2-yl)[1,2,4]triazolo[1,5-a]pyridin-2-yl]cyclopentanecarboxamide;
N-[5-(1H-pyrrol-2-yl)[1,2,4]triazolo[1,5-a]pyridin-2-yl]benzamide;
N-[5-(1H-pyrazol-4-yl)[1,2,4]triazolo[1,5-a]pyridin-2-yl]benzamide;
N-[5-(1H-pyrrol-2-yl)[1,2,4]triazolo[1,5-a]pyridin-2-yl]nicotinamide;
N-[5-(2-furyl)[1,2,4]triazolo[1,5-a]pyridin-2-yl]benzamide;
N-[6-(3-fluorophenyl)[1,2,4]triazolo[1,5-a]pyridin-2-yl]nicotinamide;
N-(6-phenyl[1,2,4]triazolo[1,5-a]pyridin-2-yl)nicotinamide;
N-[6-(3-furyl)[1,2,4]triazolo[1,5-a]pyridin-2-yl]nicotinamide;
N-[6-(3-thienyl)[1,2,4]triazolo[1,5-a]pyridin-2-yl]nicotinamide;
N-[5-(3-furyl)[1,2,4]triazolo[1,5-a]pyridin-2-yl]-3-methoxybenzamide;
N-[5-(3-furyl)[1,2,4]triazolo[1,5-a]pyridin-2-yl]-2-(2-thienyl)acetamide;
N-[5-(3-furyl)[1,2,4]triazolo[1,5-a]pyridin-2-yl]cyclopentanecarboxamide;
N-[5-(3-furyl)[1,2,4]triazolo[1,5-a]pyridin-2-yl]-4-methoxybenzamide;
N-[5-(3-furyl)[1,2,4]triazolo[1,5-a]pyridin-2-yl]isonicotinamide;
N-[5-(3-furyl)[1,2,4]triazolo[1,5-a]pyridin-2-yl]quinoxaline-6-carboxamide;
N-[6-(3-methoxyphenyl)[1,2,4]triazolo[1,5-a]pyridin-2-yl]nicotinamide;
N-[6-(3-aminophenyl)[1,2,4]triazolo[1,5-a]pyridin-2-yl]nicotinamide;
N-[6-(3-cyanophenyl)[1,2,4]triazolo[1,5-a]pyridin-2-yl]nicotinamide;
N-[5-(3-furyl)[1,2,4]triazolo[1,5-a]pyridin-2-yl]isoxazole-5-carboxamide;
N-[5-(3-furyl)[1,2,4]triazolo[1,5-a]pyridin-2-yl]-2,3-dihydro-1,4-benzodioxine-6-carboxamide;
N-[5-(cyclopropylamino)[1,2,4]triazolo[1,5-a]pyridin-2-yl]nicotinamide;
N-(5-pyrrolidin-1-yl[1,2,4]triazolo[1,5-a]pyridin-2-yl)nicotinamide;
N-[5-(3-furyl)[1,2,4]triazolo[1,5-a]pyridin-2-yl]-3,5-dimethoxybenzamide;
N-[5-(3-furyl)[1,2,4]triazolo[1,5-a]pyridin-2-yl]biphenyl-4-carboxamide;
1-(4-chlorophenyl)-N-[5-(3-furyl)[1,2,4]triazolo[1,5-a]pyridin-2-yl]cyclopentanecarboxamide;
N-[5-(3-furyl)[1,2,4]triazolo[1,5-a]pyridin-2-yl]-2,3-dihydro-1-benzofuran-5-carboxamide;
N-[5-(3-furyl)[1,2,4]triazolo[1,5-a]pyridin-2-yl]-3-furamide;
1-acetyl-N-[5-(3-furyl)[1,2,4]triazolo[1,5-a]pyridin-2-yl]piperidine-4-carboxamide;
2,2-difluoro-N-[5-(3-furyl)[1,2,4]triazolo[1,5-a]pyridin-2-yl]-1,3-benzodioxole-4-carboxamide;
N-[5-(3-thienyl)[1,2,4]triazolo[1,5-a]pyridin-2-yl]nicotinamide;
N-[1,2,4]triazolo[1,5-a]quinolin-2-ylnicotinamide;
N-[5-(cyclopentylamino)[1,2,4]triazolo[1,5-a]pyridin-2-yl]benzamide;
N-[5-(3-furyl)[1,2,4]triazolo[1,5-a]pyridin-2-yl]nicotinamide 1-oxide;
N-{5-[(3-methoxypropyl)amino][1,2,4]triazolo[1,5-a]pyridin-2-yl}benzamide;
N-{5-[(2-furylmethyl)amino][1,2,4]triazolo[1,5-a]pyridin-2-yl}benzamide;
N-{5-[(tetrahydro furan-2-ylmethyl)amino][1,2,4]triazolo[1,5-a]pyridin-2-yl}benzamide;
3-(acetylamino)-N-[5-(3-furyl)[1,2,4]triazolo[1,5-a]pyridin-2-yl]benzamide;
N-[5-(cyclohexylamino)[1,2,4]triazolo[1,5-a]pyridin-2-yl]benzamide;
N-[5-(3-furyl)[1,2,4]triazolo[1,5-a]pyridin-2-yl]-3-(methylsulfonyl)benzamide;
3-(aminomethyl)-N-[5-(3-furyl)[1,2,4]triazolo[1,5-a]pyridin-2-yl]benzamide;
N-(5-{[1-(hydroxymethyl)propyl]amino}[1,2,4]triazolo[1,5-a]pyridin-2-yl)benzamide;
N-[6-(3-hydroxyphenyl)[1,2,4]triazolo[1,5-a]pyridin-2-yl]benzamide;
tert-butyl[4-({[5-(3-furyl)[1,2,4]triazolo[1,5-a]pyridin-2-yl]amino}carbonyl)benzyl]carbamate;
N-[5-(3-furyl)[1,2,4]triazolo[1,5-a]pyridin-2-yl]-4-isobutylbenzamide;
tert-butyl[4-({[5-(3-furyl)[1,2,4]triazolo[1,5-a]pyridin-2-yl]amino}carbonyl)phenoxy]acetate;
4-butyl-N-[5-(3-furyl)[1,2,4]triazolo[1,5-a]pyridin-2-yl]benzamide;
N-[6-(4-hydroxy-3-methoxyphenyl)[1,2,4]triazolo[1,5-a]pyridin-2-yl]benzamide hydrochloride;
N-{5-[(2-methoxyethyl)amino][1,2,4]triazolo[1,5-a]pyridin-2-yl}benzamide;
N-{5-[(2,3-dihydroxypropyl)amino][1,2,4]triazolo[1,5-a]pyridin-2-yl}benzamide;
N-[6-(2,3-dihydro-1-benzofuran-5-yl)[1,2,4]triazolo[1,5-a]pyridin-2-yl]benzamide;
N-[5-(b enzylamino)[1,2,4]triazolo[1,5-a]pyridin-2-yl]nicotinamide;
N-[5-(cyclo heptylamino)[1,2,4]triazolo[1,5-a]pyridin-2-yl]nicotinamide dihydrochloride;
N-[5-(cyclohexylamino)[1,2,4]triazolo[1,5-a]pyridin-2-yl]nicotinamide;
N-(5-{[(5-methyl-2-furyl)methyl]amino}[1,2,4]triazolo[1,5-a]pyridin-2-yl)nicotinamide;
N-{5-[(tetrahydrofuran-2-ylmethyl)amino][1,2,4]triazolo[1,5-a]pyridin-2-yl}nicotinamide;
N-[6-(4-hydroxyphenyl)[1,2,4]triazolo[1,5-a]pyridin-2-yl]benzamide;

N-[6-(4-hydroxy-3-methoxyphenyl)[1,2,4]triazolo[1,5-a]pyridin-2-yl]nicotinamide hydrochloride;
N-[5-(cyclooctylamino)[1,2,4]triazolo[1,5-a]pyridin-2-yl]nicotinamide;
N-{5-[cyclohexyl(methyl)amino][1,2,4]triazolo[1,5-a]pyridin-2-yl}nicotinamide;
N-[5-(tetrahydro-2H-pyran-4-ylamino)[1,2,4]triazolo[1,5-a]pyridin-2-yl]nicotinamide;
N-{5-[(1-methylpiperidin-4-yl)amino][1,2,4]triazolo[1,5-a]pyridin-2-yl}nicotinamide;
N-{5-[(3-aminocyclohexyl)amino][1,2,4]triazolo[1,5-a]pyridin-2-yl}benzamide;
N-{5-[(1-methylpiperidin-4-yl)amino][1,2,4]triazolo[1,5-a]pyridin-2-yl}benzamide;
N-[5-(cyclopropylamino)-7-(trifluoromethyl)[1,2,4]triazolo[1,5-a]pyridin-2-yl]nicotinamide;
N-[5-(cyclohexylamino)-7-(trifluoromethyl)[1,2,4]triazolo[1,5-a]pyridin-2-yl]nicotinamide;
N-[5-(cycloheptylamino)-7-(trifluoromethyl)[1,2,4]triazolo[1,5-a]pyridin-2-yl]nicotinamide;
N-[5-(cyclopentylamino)-7-(trifluoromethyl)[1,2,4]triazolo[1,5-a]pyridin-2-yl]nicotinamide;
N-[5-[(cyclohexylmethyl)amino]-7-(trifluoromethyl)[1,2,4]triazolo[1,5-a]pyridin-2-yl]nicotinamide;
N-(6-bromo-5-methyl[1,2,4]triazolo[1,5-a]pyridin-2-yl)nicotinamide;
N-{5-[(3-hydroxycyclohexyl)amino][1,2,4]triazolo[1,5-a]pyridin-2-yl}nicotinamide;
N-{5-[(4-tert-butylcyclohexyl)amino][1,2,4]triazolo[1,5-a]pyridin-2-yl}nicotinamide;
N-[5-(tetrahydro-2H-pyran-3-ylamino)[1,2,4]triazolo[1,5-a]pyridin-2-yl]benzamide;
N-[5-(cycloheptylamino)[1,2,4]triazolo[1,5-a]pyridin-2-yl]-4-(morpholin-4-ylmethyl)benzamide;
N-[5-(cyclohexylthio)[1,2,4]triazolo[1,5-a]pyridin-2-yl]nicotinamide;
N-{5-[(trans-4-hydroxycyclohexyl)amino][1,2,4]triazolo[1,5-a]pyridin-2-yl}nicotinamide;
N-[5-(cyclobutylamino)-7-(trifluoromethyl)[1,2,4]triazolo[1,5-a]pyridin-2-yl]nicotinamide;
N-[5-(cyclohexylamino)[1,2,4]triazolo[1,5-a]pyridin-2-yl]-6-morpholin-4-ylnicotinamide;
N-[5-(cyclohexylamino)[1,2,4]triazolo[1,5-a]pyridin-2-yl]-4-[(dimethylamino)methyl]benzamide;
N-[5-(cyclohexylamino)[1,2,4]triazolo[1,5-a]pyridin-2-yl]-3-(morpholin-4-ylmethyl)benzamide;
N-[5-[(cyclopropylmethyl)amino]-7-(trifluoromethyl)[1,2,4]triazolo[1,5-a]pyridin-2-yl]nicotinamide;
methyltrans-4-{[2-[(pyridin-3-ylcarbonyl)amino]-7-(trifluoromethyl)[1,2,4]triazolo[1,5-a]pyridin-5-yl]amino}cyclohexanecarboxylate;
N-[5-{[(1RS,2RS)-2-(hydroxymethyl)cyclohexyl]amino}-7-(trifluoromethyl)[1,2,4]triazolo[1,5-a]pyridin-2-yl]nicotinamide;
N-[6-bromo-5-(cyclohexylamino)[1,2,4]triazolo[1,5-a]pyridin-2-yl]nicotinamide;
N-[5-(cycloheptylamino)[1,2,4]triazolo[1,5-a]pyridin-2-yl]tetrahydro-2H-pyran-4-carboxamide;
N-[5-(2-methylprop-1-en-1-yl)[1,2,4]triazolo[1,5-a]pyridin-2-yl]nicotinamide dihydrochloride;
N-(3-oxo-3-{[5-(1H-pyrazol-1-yl)[1,2,4]triazolo[1,5-a]pyridin-2-yl]amino}propyl)benzamide;
N-(3-{[5-(3-furyl)[1,2,4]triazolo[1,5-a]pyridin-2-yl]amino}-3-oxopropyl)benzamide;
N-(3-{[5-(2-furyl)[1,2,4]triazolo[1,5-a]pyridin-2-yl]amino}-3-oxopropyl)benzamide;
N-(3-{[5-(cyclohexylamino)[1,2,4]triazolo[1,5-a]pyridin-2-yl]amino}-3-oxopropyl)benzamide;
N-[5-(isopropylamino)-7-(trifluoromethyl)[1,2,4]triazolo[1,5-a]pyridin-2-yl]nicotinamide;
N-[5-(sec-butylamino)-7-(trifluoromethyl)[1,2,4]triazolo[1,5-a]pyridin-2-yl]nicotinamide;
N-[5-(methylamino)-7-(trifluoromethyl)[1,2,4]triazolo[1,5-a]pyridin-2-yl]nicotinamide;
N-[8-(3-furyl)[1,2,4]triazolo[1,5-a]pyridin-2-yl]benzamide;
N-[5-(cyclohexyloxy)[1,2,4]triazolo[1,5-a]pyridin-2-yl]-2-(3-methoxyphenyl)acetamide;
N-[5-(cyclohexyloxy)[1,2,4]triazolo[1,5-a]pyridin-2-yl]nicotinamide;
N-[5-(cyclohexylamino)[1,2,4]triazolo[1,5-a]pyridin-2-yl]-6-(2-pyrrolidin-1-ylethyl)nicotinamide;
N-[5-(cyclohexylamino)[1,2,4]triazolo[1,5-a]pyridin-2-yl]-6-(morpholin-4-ylmethyl)nicotinamide;
N-[5-(3-furyl)[1,2,4]triazolo[1,5-a]pyridin-2-yl]cyclopropanecarboxamide;
N-[5-(3-thienyl)[1,2,4]triazolo[1,5-a]pyridin-2-yl]benzamide;
N-[5-(3-furyl)[1,2,4]triazolo[1,5-a]pyridin-2-yl]benzamide;
N-[5-(3-furyl)[1,2,4]triazolo[1,5-a]pyridin-2-yl]benzamide;
N-[6-(4-hydroxy-3-methoxyphenyl)[1,2,4]triazolo[1,5-a]pyridin-2-yl]acetamide;
N-[6-(4-hydroxy-3,5-dimethylphenyl)[1,2,4]triazolo[1,5-a]pyridin-2-yl]nicotinamide;
4-[2-(benzoylamino)[1,2,4]triazolo[1,5-a]pyridin-6-yl]-N-[2-(dimethylamino)ethyl]benzamide;
N-[6-(1H-pyrazol-4-yl)[1,2,4]triazolo[1,5-a]pyridin-2-yl]benzamide;
N-{5-[(cyclohexylmethyl)amino][1,2,4]triazolo[1,5-a]pyridin-2-yl}nicotinamide;
N-{5-[(4-hydroxycyclohexyl)amino][1,2,4]triazolo[1,5-a]pyridin-2-yl}-3-methoxybenzamide;
N-[5-(cyclopentylamino)[1,2,4]triazolo[1,5-a]pyridin-2-yl]-2-furamide;
N-[7-chloro-5-(cyclobutylamino)[1,2,4]triazolo[1,5-a]pyridin-2-yl]nicotinamide;
N-[7-chloro-5-(cyclopentylamino)[1,2,4]triazolo[1,5-a]pyridin-2-yl]nicotinamide;
N-[7-chloro-5-(cyclohexylamino)[1,2,4]triazolo[1,5-a]pyridin-2-yl]nicotinamide;
N-[5-(sec-butylamino)-7-chloro[1,2,4]triazolo[1,5-a]pyridin-2-yl]nicotinamide;
N-[7-chloro-5-(cyclopropylamino)[1,2,4]triazolo[1,5-a]pyridin-2-yl]nicotinamide;
N-[5-[(2-methoxyethyl)amino]-7-(trifluoromethyl)[1,2,4]triazolo[1,5-a]pyridin-2-yl]nicotinamide;
N-[5-[(3-hydroxypropyl)amino]-7-(trifluoromethyl)[1,2,4]triazolo[1,5-a]pyridin-2-yl]nicotinamide;
N-[5-[(2-hydroxyethyl)amino]-7-(trifluoromethyl)[1,2,4]triazolo[1,5-a]pyridin-2-yl]nicotinamide;
N-[5-(dimethylamino)-7-(trifluoromethyl)[1,2,4]triazolo[1,5-a]pyridin-2-yl]nicotinamide;
N-[5-(cyclohexylamino)[1,2,4]triazolo[1,5-a]pyridin-2-yl]-2-pyridin-3-ylacetamide;
N-[5-(cyclohexylamino)[1,2,4]triazolo[1,5-a]pyridin-2-yl]-4-(piperidin-1-ylmethyl)benzamide;
N-[5-(cyclohexylamino)[1,2,4]triazolo[1,5-a]pyridin-2-yl]-4-(pyrrolidin-1-ylmethyl)benzamide;
N-[5-(cyclohexylamino)[1,2,4]triazolo[1,5-a]pyridin-2-yl]-4-{[(2-methoxyethyl)(methyl)amino]methyl}benzamide;
N-[5-(cyclohexylamino)[1,2,4]triazolo[1,5-a]pyridin-2-yl]-6-methylnicotinamide;
N-[5-(cyclohexylamino)[1,2,4]triazolo[1,5-a]pyridin-2-yl]-6-[(3-hydroxypropyl)amino]nicotinamide;

N-[5-(cyclohexylamino)[1,2,4]triazolo[1,5-a]pyridin-2-yl]-6-[(2-furylmethyl)amino]nicotinamide;
N-[5-(cyclohexylamino)[1,2,4]triazolo[1,5-a]pyridin-2-yl]nicotinamide 1-oxide;
N-[5-(isopropylamino)-7-(trifluoromethyl)[1,2,4]triazolo[1,5-a]pyridin-2-yl]-2-pyridin-3-ylacetamide trihydrochloride;
N-[5-[(1-ethylpropyl)amino]-7-(trifluoromethyl)[1,2,4]triazolo[1,5-a]pyridin-2-yl]nicotinamide;
N-[5-(isopropylamino)-7-(trifluoromethyl)[1,2,4]triazolo[1,5-a]pyridin-2-yl]nicotinamide 1-oxide;
N-[5-[(3-hydroxycyclohexyl)amino]-7-(trifluoromethyl)[1,2,4]triazolo[1,5-a]pyridin-2-yl]nicotinamide formic acid;
N-{7-chloro-5-[(3-hydroxycyclohexyl)amino][1,2,4]triazolo[1,5-a]pyridin-2-yl}nicotinamide formic acid;
N-[5-(cyclopropylamino)-7-(trifluoromethyl)[1,2,4]triazolo[1,5-a]pyridin-2-yl]-4-[dimethylamino)methyl]benzamide;
N-[5-(cyclopropylamino)-7-(trifluoromethyl)[1,2,4]triazolo[1,5-a]pyridin-2-yl]-4-[(2-oxopyrrolidin-1-yl)methyl]benzamide;
N-[5-(cyclopropylamino)-7-(trifluoromethyl)[1,2,4]triazolo[1,5-a]pyridin-2-yl]-6-pyrrolidin-1-ylnicotinamide;
N-[5-(cyclopropylamino)-7-(trifluoromethyl)[1,2,4]triazolo[1,5-a]pyridin-2-yl]-6-methylnicotinamide;
N-[6-(4-hydroxy-3-methoxyphenyl)[1,2,4]triazolo[1,5-a]pyridin-2-yl]-4-(piperidin-1-ylmethyl)benzamide;
N-[6-(4-hydroxy-3-methoxyphenyl)[1,2,4]triazolo[1,5-a]pyridin-2-yl]-6-methylnicotinamide;
N-[6-(4-hydroxy-3-methoxyphenyl)[1,2,4]triazolo[1,5-a]pyridin-2-yl]-4-[(2-oxopyrrolidin-1-yl)methyl]benzamide;
4-[(dimethylamino)methyl]-N-[6-(4-hydroxy-3-methoxyphenyl)[1,2,4]triazolo[1,5-a]pyridin-2-yl]benzamide;
N-[5-{[(1R,2 S)-2-(hydroxymethyl)cyclohexyl]amino}-7-(trifluoromethyl)[1,2,4]triazolo[1,5-a]pyridin-2-yl]nicotinamide hydrochloride;
N-[5-(cyclopropylamino)-7-(trifluoromethyl)[1,2,4]triazolo[1,5-a]pyridin-2-yl]-4-[(4-hydroxypiperidin-1-yl)methyl]benzamide;
N-[5-(cyclopropylamino)-7-(trifluoromethyl)[1,2,4]triazolo[1,5-a]pyridin-2-yl]-4-(pyrrolidin-1-ylmethyl)benzamide;
N-[5-(cyclopropylamino)-7-(trifluoromethyl)[1,2,4]triazolo[1,5-a]pyridin-2-yl]-6-(4-hydroxypiperidin-1-yl)nicotinamide;
N-[5-(cyclopropylamino)-7-(trifluoromethyl)[1,2,4]triazolo[1,5-a]pyridin-2-yl]-6-piperazin-1-ylnicotinamide;
N-[5-(cyclopropylamino)-7-(trifluoromethyl)[1,2,4]triazolo[1,5-a]pyridin-2-yl]-6-(dimethylamino)nicotinamide;
N-[6-bromo-5-(cyclopentylamino)[1,2,4]triazolo[1,5-a]pyridin-2-yl]-6-morpholin-4-ylnicotinamide;
N-[5-(cyclopropylamino)-7-(trifluoromethyl)[1,2,4]triazolo[1,5-a]pyridin-2-yl]-6-morpholin-4-ylnicotinamide;
N-[5-(cyclohexylamino)[1,2,4]triazolo[1,5-a]pyridin-2-yl]-6-(dimethylamino)nicotinamide;
tert-butyl 4-[5-({[5-(cyclopropylamino)-7-(trifluoromethyl)[1,2,4]triazolo[1,5-a]pyridin-2-yl]amino}carbonyl)pyridin-2-yl]piperazine-1-carboxylate;
N-[5-(cyclohexylamino)[1,2,4]triazolo[1,5-a]pyridin-2-yl]-4-[(4-hydroxypiperidin-1-yl)methyl]benzamide;
N-[5-(cyclohexylamino)[1,2,4]triazolo[1,5-a]pyridin-2-yl]-6-(4-fluoropiperidin-1-yl)nicotinamide;
N-[5-(cyclohexylamino)[1,2,4]triazolo[1,5-a]pyridin-2-yl]-6-(1H-pyrazol-1-yl)nicotinamide;
tert-butyl 4-[5-({[5-(cyclohexylamino)[1,2,4]triazolo[1,5-a]pyridin-2-yl]amino}carbonyl)pyridin-2-yl]piperazine-1-carboxylate;
N-[5-(cyclopropylamino)-7-(trifluoromethyl)[1,2,4]triazolo[1,5-a]pyridin-2-yl]-6-[(3-hydroxypropyl)amino]nicotinamide;
N-[5-(isopropylamino)-7-(trifluoromethyl)[1,2,4]triazolo[1,5-a]pyridin-2-yl]-6-(morpholin-4-ylmethyl)nicotinamide;
N-[5-[(pyrrolidin-3-ylmethyl)amino]-7-(trifluoromethyl)[1,2,4]triazolo[1,5-a]pyridin-2-yl]nicotinamide;
N-[5-(cyclohexylamino)[1,2,4]triazolo[1,5-a]pyridin-2-yl]-4-(piperazin-1-ylmethyl)benzamide;
N-[5-(cyclohexylamino)[1,2,4]triazolo[1,5-a]pyridin-2-yl]-4-[(4-formylpiperazin-1-yl)methyl]benzamide;
N-[5-(piperidin-3-ylamino)-7-(trifluoromethyl)[1,2,4]triazolo[1,5-a]pyridin-2-yl]nicotinamide;
N-[5-(sec-butylamino)-7-chloro[1,2,4]triazolo[1,5-a]pyridin-2-yl]-6-[(2-methoxyethyl)(methyl)amino]nicotinamide;
N-[5-(sec-butylamino)-7-chloro[1,2,4]triazolo[1,5-a]pyridin-2-yl]-6-[(3-hydroxypropyl)amino]nicotinamide;
N-[5-(sec-butylamino)-7-chloro[1,2,4]triazolo[1,5-a]pyridin-2-yl]-6-morpholin-4-ylnicotinamide;
N-[5-(sec-butylamino)-7-chloro[1,2,4]triazolo[1,5-a]pyridin-2-yl]-4-{[(2-methoxyethyl)(methyl)amino]methyl}benzamide;
N-[5-(sec-butylamino)-7-chloro[1,2,4]triazolo[1,5-a]pyridin-2-yl]-6-methylnicotinamide;
N-[7-chloro-5-(isopropylamino)[1,2,4]triazolo[1,5-a]pyridin-2-yl]nicotinamide;
N-[5-[(3-isopropoxyphenyl)amino]-7-(trifluoromethyl)[1,2,4]triazolo[1,5-a]pyridin-2-yl]nicotinamide;
N-[5-[(3-fluoro-4-methoxyphenyl)amino]-7-(trifluoromethyl)[1,2,4]triazolo[1,5-a]pyridin-2-yl]nicotinamide;
N-[5-{[3-(benzyloxy)phenyl]amino}-7-(trifluoromethyl)[1,2,4]triazolo[1,5-a]pyridin-2-yl]nicotinamide;
N-[5-(sec-butylamino)-7-chloro[1,2,4]triazolo[1,5-a]pyridin-2-yl]-4-(morpholin-4-ylmethyl)benzamide;
N-[5-(isopropylamino)-7-(trifluoromethyl)[1,2,4]triazolo[1,5-a]pyridin-2-yl]-6-methylnicotinamide;
6-chloro-N-[5-(isopropylamino)-7-(trifluoromethyl)[1,2,4]triazolo[1,5-a]pyridin-2-yl]nicotinamide;
6-[(2-aminoethyl)amino]-N-[5-(isopropylamino)-7-(trifluoromethyl)[1,2,4]triazolo[1,5-a]pyridin-2-yl]nicotinamide;
N-[5-(sec-butylamino)-7-methyl[1,2,4]triazolo[1,5-a]pyridin-2-yl]nicotinamide;
N-[5-(isopropylamino)-7-methyl[1,2,4]triazolo[1,5-a]pyridin-2-yl]nicotinamide.

In another aspect the invention relates to the following intermediate compounds:
5-(3-thienyl)[1,2,4]triazolo[1,5-a]pyridin-2-amine;
5-(3-furyl)[1,2,4]triazolo[1,5-a]pyridin-2-amine;
5-bromo[1,2,4]triazolo[1,5-a]pyridin-2-amine;
5-chloro[1,2,4]triazolo[1,5-a]pyridin-2-amine;
6-bromo[1,2,4]triazolo[1,5-a]pyridin-2-amine;
tert-butyl 2-(2-amino[1,2,4]triazolo[1,5-a]pyridin-5-yl)-1H-pyrrole-1-carboxylate;
5-chloro-7-(trifluoromethyl)[1,2,4]triazolo[1,5-a]pyridin-2-amine;
6-bromo-5-methyl[1,2,4]triazolo[1,5-a]pyridin-2-amine;
$N^5$-cyclohexyl[1,2,4]triazolo[1,5-a]pyridine-2,5-diamine;
$N^5$-cycloheptyl[1,2,4]triazolo[1,5-a]pyridine-2,5-diamine;
5-(cyclohexyloxy)[1,2,4]triazolo[1,5-a]pyridin-2-amine;
5-(1H-pyrazol-1-yl)[1,2,4]triazolo[1,5-a]pyridin-2-amine;
[1,2,4]triazolo[1,5-a]quinolin-2-amine;
6-bromo-$N^5$-cyclohexyl[1,2,4]triazolo[1,5-a]pyridine-2,5-diamine;
6-bromo-$N^5$-cyclohexyl[1,2,4]triazolo[1,5-a]pyridine-2,5-diamine;

5-(2-furyl)[1,2,4]triazolo[1,5-a]pyridin-2-amine;
$N^5$-isopropyl-7-(trifluoromethyl)[1,2,4]triazolo[1,5-a]pyridine-2,5-diamine;
N-(5-bromo[1,2,4]triazolo[1,5-a]pyridin-2-yl)benzamide;
N-(5-bromo[1,2,4]triazolo[1,5-a]pyridin-2-yl)nicotinamide;
N-(5-chloro[1,2,4]triazolo[1,5-a]pyridin-2-yl)benzamide;
N-(5-chloro[1,2,4]triazolo[1,5-a]pyridin-2-yl)nicotinamide;
N-(6-bromo[1,2,4]triazolo[1,5-a]pyridin-2-yl)benzamide;
N-(6-bromo[1,2,4]triazolo[1,5-a]pyridin-2-yl)nicotinamide hydrochloride;
N-[5-chloro-7-(trifluoromethyl)[1,2,4]triazolo[1,5-a]pyridin-2-yl]nicotinamide;
4-(chloromethyl)-N-[5-(cyclohexylamino)[1,2,4]triazolo[1,5-a]pyridin-2-yl]benzamide;
N-(8-bromo[1,2,4]triazolo[1,5-a]pyridin-2-yl)benzamide;
N-(5,7-dichloro[1,2,4]triazolo[1,5-a]pyridin-2-yl)nicotinamide;
6-chloro-N-[5-(cyclohexylamino)[1,2,4]triazolo[1,5-a]pyridin-2-yl]nicotinamide;
$N^5$-cyclopropyl-7-(trifluoromethyl)[1,2,4]triazolo[1,5-a]pyridine-2,5-diamine;
5-chloro-7-methyl[1,2,4]triazolo[1,5-a]pyridin-2-amine;
N-(5-chloro-7-methyl[1,2,4]triazolo[1,5-a]pyridin-2-yl)nicotinamide.

In another aspect the invention relates to the use of triazolopyridine compounds according to the invention for use as a medicament.

In another aspect the invention relates to a method for the prevention and/or treatment of autoimmune disorders, inflammatory diseases, cardiovascular diseases and/or neurodegenerative diseases in a subject, comprising administering to the subject an effective amount of a compound according to the invention.

The compounds according to the invention may be used for the preparation of a medicament for modulating and/or inhibiting the activity or function of ASK, in particular ASK-1, in a subject and in particular for preventing and/or treating autoimmune disorders, inflammatory diseases, cardiovascular diseases and/or neurodegenerative diseases.

In another aspect the invention relates to a method for the prevention and/or treatment of autoimmune disorders, inflammatory diseases, cardiovascular diseases and/or neurodegenerative diseases in a subject, comprising administering to the subject an effective amount of a compound according to the invention in combination with other active compounds useful in the same indication in order to achieve increased efficacy.

In another aspect the compounds according to the invention may advantageously be used in a method for modulating and/or inhibiting the activity or function of ASK, in particular ASK-1, in a subject, comprising administering to the subject an effective amount of one or more of said compounds.

Another aspect of the invention is a pharmaceutical composition containing at least one triazolopyridine compound according to the invention and a pharmaceutically acceptable carrier, diluent or excipient.

Another aspect of the invention is a process for the preparation of a triazolopyridine compound according to formula (I), comprising the step of reacting a compound of Formula (II) with an acylating agent of Formulas (IIIa or IIIb) in a presence of a base or a coupling agent:

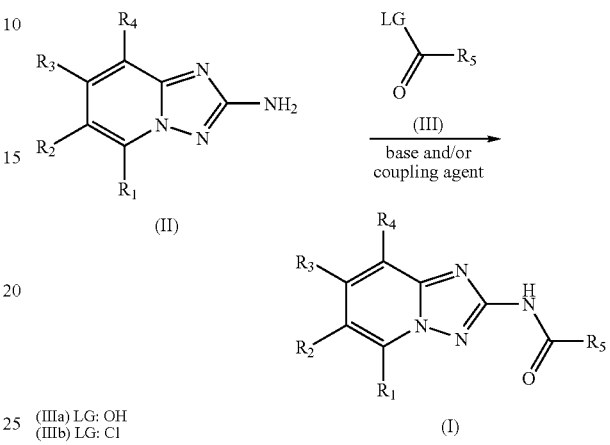

(IIIa) LG: OH
(IIIb) LG: Cl wherein $R_1$, $R_2$, $R_3$, $R_4$, $R_5$ are as defined in any of the above definitions, wherein the base is selected from tertiary amine bases such as DIEA, TEA, NMM or pyridine, and the coupling agent is selected from a peptide coupling agent such as DCC, HATU, EDC/HOBt, i-butylchloroformate, carbonyl diimidazole, Mukaiyama's reagent in a suitable solvent such as DCM or $CH_3CN$; and optionally further purifying the obtained compound.

A further aspect is a process for the preparation of a triazolopyridine compound according to formula (Ia) or (Ic), comprising A) the step of reacting a compound of Formula (Ib) wherein $R_1$, $R_2$, $R_3$, $R_4$ are as above defined but at least one is a group X selected from a halogen such as F, Br, Cl, I or a sulfonate ester such as OTf, with a boronic agent of formula (IVa) or ester (IVb) wherein $R'_1$ is an optionally substituted aryl, heteroaryl or alkenyl group as above defined in the presence of a base such as $K_2CO_3$, $K_3PO_4$ and a catalytic amount of a palladium catalyst such as $PdCl_2(PPh_3)_2$ or $Pd(OAc)_2$ with a ligand such as DPPF in an appropriate solvent such as DMF, THF, dioxane or a combination of water with toluene, DMF, THF or dioxane to give a compound of formula (Ia) wherein at least one of $R_1$, $R_2$, $R_3$, $R_4$ is $R'_1$ or B) the step of reacting a compound of Formula (Id) wherein $R_1$ is a leaving group such as F, Cl, Br, I, OMs, OTf or $SR_{13}$ where $R_{13}$ is an alkyl group with a secondary amine $NHR_6R_7$ of formula (V) wherein $R_6$ and $R_7$ are as above defined in a polar solvent such as ethanol or butanol or the amine itself to give a compound of formula (Ic) wherein $R_1$ is $NR_5R_6$, and optionally further purifying the obtained compound.

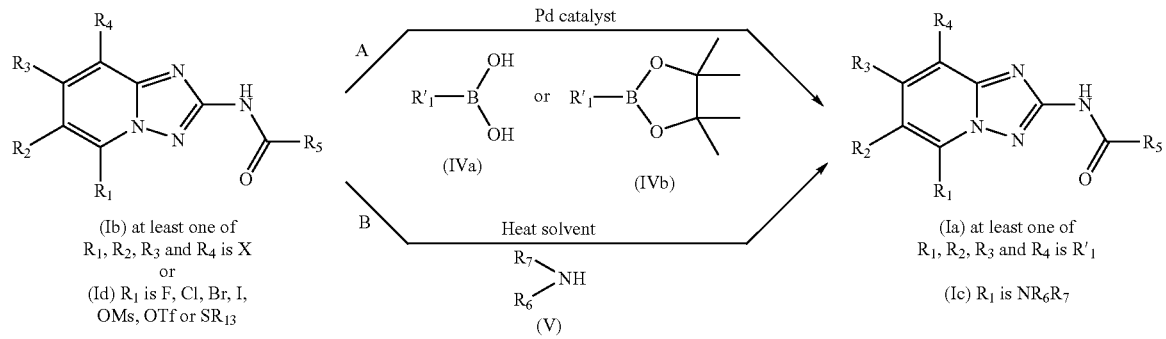

Yet another aspect of the invention is a process for the preparation of a triazolopyridine compound according to formula (IIa) wherein $R_2$, $R_3$, $R_4$, $R_5$ and $R_6$ are as above defined, comprising the step of reacting a triazolopyridine compound of Formula (IIb) wherein $R_1$ is a leaving group such as F, Cl, Br, I, OMs, OTf or $SR_{13}$ where $R_{13}$ is an alkyl group with a secondary amine $NHR_6R_7$ of formula (V) wherein $R_6$ and $R_7$ are as above defined in a polar solvent such as ethanol or butanol or the amine itself to give a compound of formula (Ic) wherein $R_1$ is $NR_5R_6$; and optionally further purifying the obtained compound.

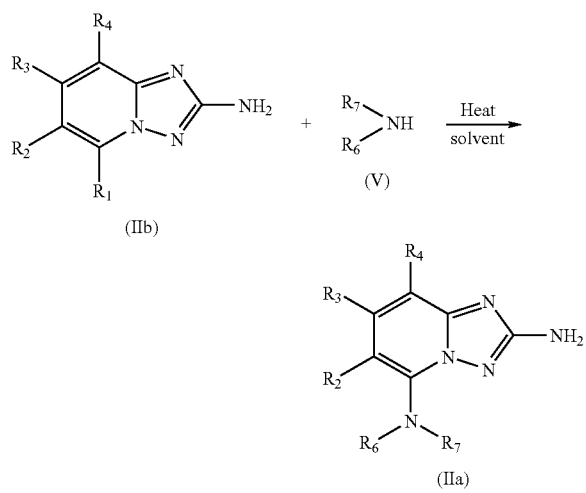

Synthesis of Compounds of the Invention

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq. (equivalent), mL (milliliter), μL (microliter), ACN (acetonitrile), BINAP (2,2'-bis(di phenylphosphino)-1,1'-binaphthalene), Boc (tert-Butoxycarbonyl), BuLi (Butyl Lithium), HATU (O-(7-azabenzotriazol-1-yl)-N,N,N',N'-tetramethyluronium hexafluoro-phosphate), c-Hex (Cyclohexane), DCC (Dicycloexylcarbodiimide), DCM (Dichloromethane), DEA (diethylamine), DIEA (Diisopropylethylamine), DMF (Dimethylformamide), DMSO (Dimethyl sulfoxide), DMSO-$d_6$ (Deuterated dimethylsulfoxide), DPPF (1,1'-bis(diphenylphosphino)ferrocene), EDC (1-ethyl-3-(3-dimethylaminopropyl)carbodiimide hydrochloride), EtOAc (Ethyl acetate), ESI (Electro-spray ionization), $Et_2O$ (Diethyl ether), EtOH (Ethanol), HOBT (1-hydroxybenzotriazole), HPLC (High Performance Liquid Chromatography), i-PrOH (2-propanol), MS (mass spectrometry), MTBE (Methyl tert-butyl ether), MW (micro-wave irradiation), NMM (N-methylmorpholine), NMR (Nuclear Magnetic Resonance), OTf (trifluoromethanesulfonate), rt (room temperature), SPE (solid phase extraction), TEA (Triethylamine), TFA (Trifluoroacetic acid), THF (Tetrahydrofuran), TLC (Thin Layer Chromatography).

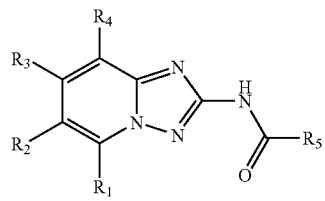

The triazolopyridines compounds according to Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated.

Generally, the triazolopyridines compounds according to the general Formula (I) may be obtained by several processes using both solution-phase and solid-phase chemistry protocols. Examples of synthetic pathways will be described. Optimum reaction conditions may vary with the particular reactants or solvents used, but such conditions can be determined by the person skilled in the art, using routine optimisation procedures.

Depending on the nature of $R_1$, $R_2$, $R_3$, $R_4$ and $R_5$, different synthetic strategies may be selected for the synthesis of compounds of Formula (I). In the process illustrated in the following schemes $R_1$, $R_2$, $R_3$, $R_4$ and $R_5$ are as above-defined in the description.

In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

According to one process as of scheme 1, triazolopyridine compounds according to the general Formula (I) whereby $R_1$, $R_2$, $R_3$, $R_4$ and $R_5$ are defined as in any of the above definitions, are prepared from the corresponding triazolopyridine amino compounds of formula (II) by reaction with an acylating agent of general Formula (III) whereby the substituent $R_5$ is as in any of the above definitions, while LG could be any appropriate leaving group such as Cl, OH. Preferred acylating agents (III) are acid chlorides (IIIa) used in conjunction with a base such as tertiary amine bases (e.g. DIEA, TEA, NMM), pyridine, or carboxylic acids (IIIb), used in conjunction with a peptide coupling agent (in solution or solid supported) such as DCC, HATU, EDC/HOBt, i-butylchloroformate, carbonyl diimidazole, Mukaiyama's reagent in the presence or the absence of a base such as DIEA, sodium tert-butytoxide.

Scheme 1

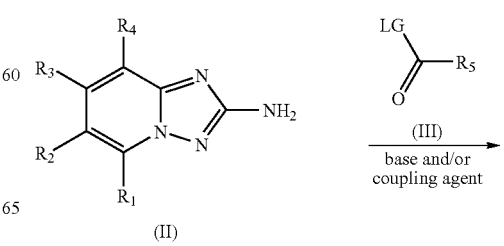

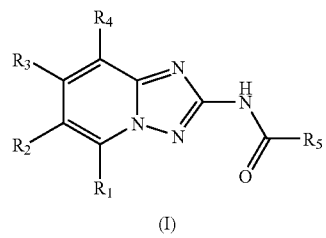

(I)

(IIIa) LG: Cl
(IIIb) LG: OH

A preferred condition for the preparation of a compound of Formula (I) whereby $R_1$, $R_2$, $R_3$, $R_4$ and $R_5$ are as in any of the above definitions consists in the reaction of triazolopyridines amino derivatives of Formula (II) with an acid chloride (IIIa) wherein $R_5$ is as defined above, in a suitable solvent such as DCM or $CH_3CN$ at a temperature between 0° C. and 100° C. in the presence of pyridine.

According to a further general process, compounds of Formula (I) can be converted to alternative compounds of Formula (I), employing suitable interconversion techniques well known by a person skilled in the art.

A preferred method as of scheme 2 to prepare the triazolopyridine compounds as of scheme 2 according to the general Formula (Ia) wherein $R_1$, $R_2$, $R_3$, $R_4$ are as above defined but at least one is an aryl, a heteroaryl or an alkenyl group $R'_1$, consist in reacting triazolopyridine compounds according to the general Formula (Ib) wherein one of $R_1$, $R_2$, $R_3$ and $R_4$ are as above defined, but at least one is a group X selected from a halogen atom such as Cl, Br, I or a sulfonate ester such as OTf with a boronic acid (IVa) or ester (IVb) wherein $R'_1$ is as above defined using well known Suzuki-Miyaura reaction conditions (Miyaura, N.; Suzuki, A. *Chem. Rev.* 1995, 95, 2457; Takahiro I. and Toshiaki M., *Tetrahedron Lett.* 2005, 46, 3573-3577). In a typical procedure, triazolopyridine compounds (Ib) and boronic acid (IVa) or ester (IVb) are heated at various temperature by traditional thermic methods or using microwave technology in presence of a base such as $K_2CO_3$, $K_3PO_4$ or CsF and a catalytic amount of palladium catalyst such as $PdCl_2(PPh_3)_2$ or $Pd(OAc)_2$ with a ligand such as DPPF in an appropriate solvent such as DMF or a combination of water with THF or dioxane such as those described hereinafter in the Examples.

Scheme 2

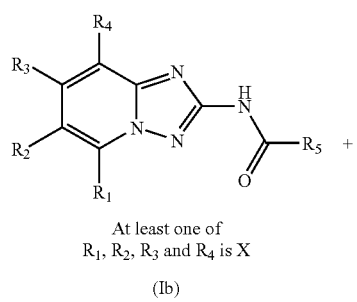

At least one of
$R_1$, $R_2$, $R_3$ and $R_4$ is X (Ib)

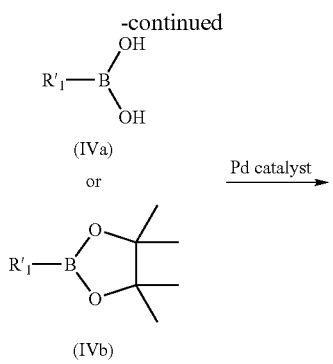

(IVa)

or

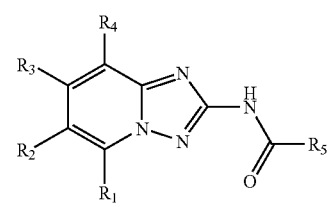

(IVb)

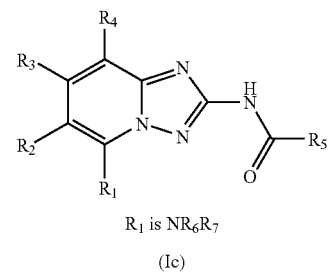

At least one of
$R_1$, $R_2$, $R_3$ and $R_4$ is $R'_1$ (Ia)

A preferred method as of scheme 3 to prepare the triazolopyridine compounds according to the general Formula (Ic) whereby $R_2$, $R_3$, $R_4$ and $NR_6R_7$ are as defined above, consists in reacting triazolopyridine compounds according to the general Formula (Id) whereby $R_2$, $R_3$, $R_4$ and $R_5$ are as above defined and $R_1$ is F, Cl, Br, I, OMs, OTf or $SR_{13}$ where $R_{13}$ is an alkyl group with an amine $R_6R_7NH$ (V). In a typical procedure, triazolopyridine compounds according to the general Formula (Id) and amines $R_6R_7NH$ (V) are heated at various temperature by traditional thermic methods or using microwave technology in an appropriate solvent such as ethanol, butanol or the amine itself such as those described hereafter in the examples.

Scheme 3

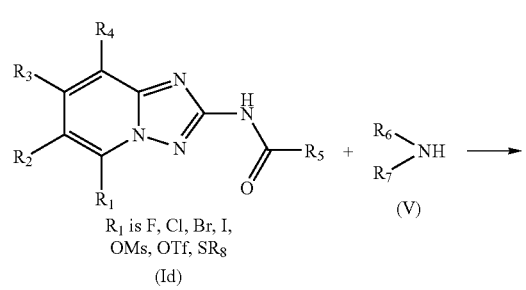

$R_1$ is F, Cl, Br, I, OMs, OTf, $SR_8$ (Id)

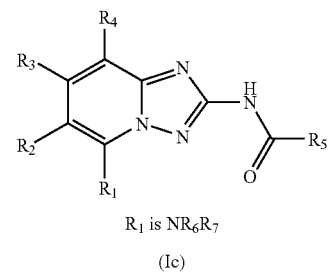

$R_1$ is $NR_6R_7$ (Ic)

Triazolopyridine amino compounds of formula (II), whereby the substituent $R^1$, $R^2$, $R^3$, and $R^4$ are as above defined, are prepared from 2-aminopyridine compounds of Formula (VI) by well known protocols such as shown in Scheme 4 below (Nettekoven M. et al., *Synthesis* 2003, 11, 1649-1652). In a typical procedure, 2-aminopyridine compounds of Formula (VI) whereby $R_1$, $R_2$, $R_3$, and $R_4$ are as above defined are reacted with an alkyloxycarbonylisothiocyanate of Formula (IX) where $R_{14}$ is an alkyl group such as methyl or ethyl in an appropriate solvent such as dioxane to give thiourea compounds (VII). Cyclisation of thiourea compounds (VII) to triazolopyridine amines of Formula (II) is then performed in presence of hydroxylamine or hydroxylamine hydrochloride in conjunction with an appropriate base such diisopropylethylamine and in an appropriate solvent such as methanol and ethanol.

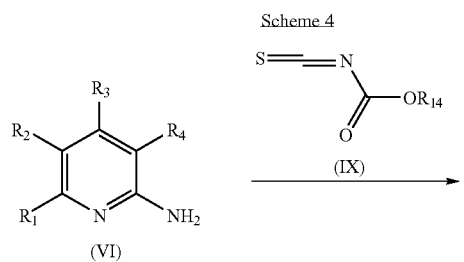

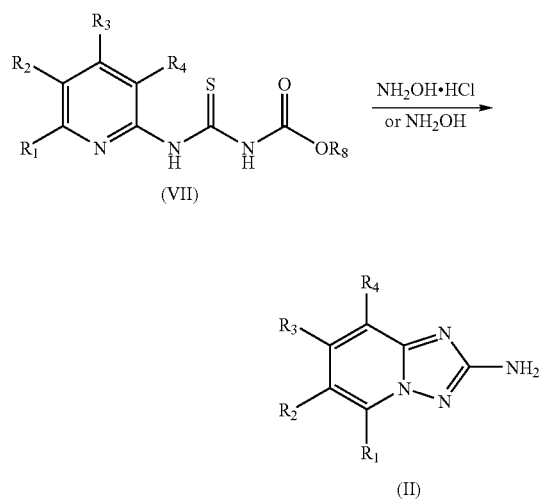

According to a further general process, compounds of Formula (II) can be converted to alternative compounds of Formula (II), employing suitable interconversion techniques well known by a person skilled in the art.

A preferred method as of scheme 5 to prepare the triazolopyridine amine compounds of Formula (IIa) whereby $R_2$, $R_3$, $R_4$ and $NR_6R_7$ are as above defined, consists in reacting triazolopyridine amine compounds according to the general Formula (IIb) whereby $R_2$, $R_3$ and $R_4$ are as above defined and $R^1$ is F, Cl, Br, I, OMs, OTf or $SR_{13}$ where $R_{13}$ is an alkyl group with an amine $R_6R_7NH$ (V). In a typical procedure, triazolopyridine amine compounds according to the general Formula (IIb) and amines $R_6R_7NH$ (V) are heated at various temperature by traditional thermic methods or using microwave technology in an appropriate solvent such as ethanol, butanol or the amine itself such as those described hereafter in the examples.

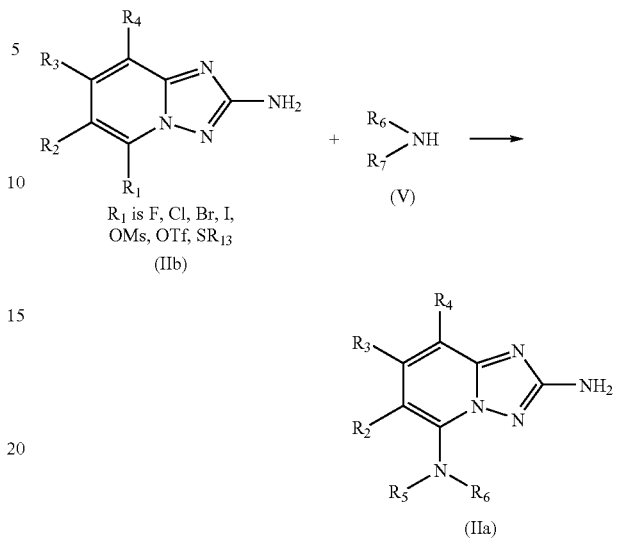

2-aminopyridine compounds of Formula (VI) whereby $R^1$, $R^2$, $R^3$, and $R^4$ are as above defined may be obtained either from commercial sources or they may be prepared from known compounds using procedures such as those described hereinafter in the examples, or conventional procedures, known by one skilled in the art.

A preferred method as of scheme 6 to prepare 2-amino pyridine compounds (VIa) whereby one of $R^1$, $R^2$, $R^3$ and $R^4$, as above defined, is an aryl, a heteroaryl or an alkenyl group $R^{11}$, consist in reacting 2-aminopyridine compounds (VIb) whereby one of $R^1$, $R^2$, $R^3$ and $R^4$, as above defined, is a group X selected from a halogen atom such as Cl, Br, I or a sulfonate ester such as OTf with a boronic acid (IVa) or ester (IVb) whereby $R^{11}$ is as above defined using well known Suzuki-Miyaura reaction conditions (Miyaura, N.; Suzuki, A. *Chem. Rev.* 1995, 95, 2457; Takahiro I. and Toshiaki M., *Tetrahedron Lett.* 2005, 46, 3573-3577). In a typical procedure, 2-aminopyridine compounds of Formula (VIb) and boronic acid (IVa) or ester (IVb) are heated at various temperature by traditional thermic methods or using microwave technology in presence of a base such as $K_2CO_3$, $K_3PO_4$ or CsF and a catalytic amount of palladium catalyst such as $PdCl_2(PPh_3)_2$ or $Pd(OAc)_2$ with DPPF in an appropriate solvent such as DMF or a combination of water with THF or dioxane such as those described hereinafter in the Examples.

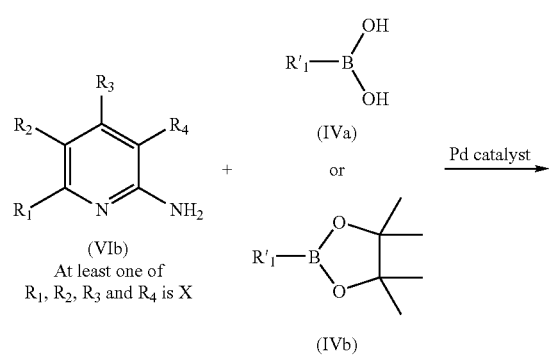

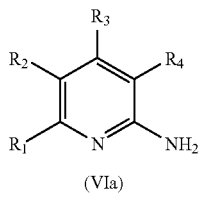

(VIa)

At least one of
R₁, R₂, R₃ and R₄ is R'₁

If the above set of general synthetic methods is not applicable to obtain compounds according to Formula (I) and/or necessary intermediates for the synthesis of compounds of Formula (I), suitable methods of preparation known by a person skilled in the art should be used. Compounds of this invention can be isolated in association with solvent molecules by crystallization or from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

The compounds of invention have been named according the standards used in the program "ACD/Name Batch" from Advanced Chemistry Development Inc., ACD/Labs (7.00 Release). Product version: 7.10, build: 15 Sep. 2003.

EXAMPLES

The novel compounds according to Formula (I) can be prepared from readily available starting materials by several synthetic approaches, using both solution-phase and solid-phase chemistry protocols or mixed solution and solid phase protocols. Examples of synthetic pathways for the will be described.

The commercially available starting materials used in the following experimental description were purchased from Aldrich, Fluka or Acros unless otherwise reported.

The HPLC, NMR and MS data provided in the examples described below are obtained as followed: HPLC: Waters Alliance 2695 equipped with Waters X-Bridge column C8 50×4.6 mm 3.5 μm, Conditions: MeCN (0.05% TFA)/H2O (0.1% TFA), 5 to 100% (8 min), max plot 230-400 nm; LC/MS spectra: waters ZMD (ES) equipped with Waters X-Bridge column C8 30×2.1 mm 3.5 μm; ¹H-NMR: Bruker DPX-300 MHz unless otherwise reported.

The preparative HPLC purifications are performed with a mass directed autopurification Fractionlynx from Waters equipped with a sunfire prep C18 OBD column 19×100 mm 5 μm, unless otherwise reported. All HPLC purifications were performed with a gradient of ACN/H2O or ACN/H2O/HCOOH (0.1%).

The microwave chemistry is performed on a single mode microwave reactor Emrys™ Optimiser from Personal Chemistry.

INTERMEDIATES

Intermediate A

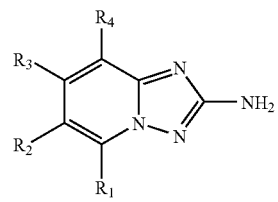

Intermediate A1

5-(3-thienyl)[1,2,4]triazolo[1,5-a]pyridin-2-amine

Step a) Formation of 6-(3-thienyl)pyridin-2-amine

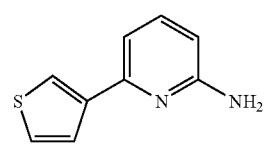

To a mixture of 2-amino-6-bromopyridine (Lancaster, 5.0 g; 28.9 mmol; 1.0 eq.), 3-thienylboronic acid (4.44 g; 34.7 mmol; 1.2 eq.), potassium phosphate (12.27 g; 57.8 mmol; 2.0 eq.) in dry dioxane (150 mL) was added 1,1'-bis(diphenylphosphino)ferrocenedichloro palladium (1.06 g; 1.44 mmol; 0.05 eq.) under inert atmosphere. The reaction mixture was heated at 80° C. overnight, cooled down to rt, filtered on a bed of celite and filtrates were evaporated under reduced pressure. Purification of the crude by flash chromatography on silica (gradient EtOAc/c-Hex, 5:95 to 50:50) gave the title compound as a beige solid (3.71 g, 73%). HPLC, Rt: 1.51 min. (purity 96.4%). LC/MS, M⁺(ESI): 177.4.

Step b) Formation of ethyl({[6-(3-thienyl)pyridin-2-yl]amino}carbonothioyl)carbamate

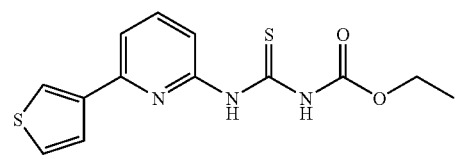

A solution of 6-(3-thienyl)pyridin-2-amine (3.70 g; 21.0 mmol; 1.0 eq.) and ethoxycarbonyl isothiocyanate (2.73 mL; 24.1 mmol; 1.15 eq.) in dioxane (100 mL) was stirred at rt overnight. The precipitate formed was filtered and washed with c-Hex to give the title compound as a white solid (4.73 g; 73%). HPLC, Rt: 4.26 min. (purity 99.9%). LC/MS, M⁺(ESI): 308.3.

Step c) Formation of
5-(3-thienyl)[1,2,4]triazolo[1,5-a]pyridin-2-amine

Intermediate A1

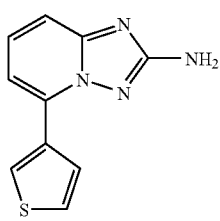

A suspension of ethyl({[6-(3-thienyl)pyridin-2-yl]amino}carbonothioyl)carbamate (4.0 g; 13.01 mmol; 1.0 eq.), hydroxylamine hydrochloride (4.52 g; 65.1 mmol; 5.0 eq.) and DIEA (6.55 mL) in MeOH/EtOH (1:1, 120 mL) was stirred at rt for 2 hours and then at 70° C. for 3 hours. Solvents were removed under reduced pressure, the residue was taken up in dioxane/water (1:1) and filtered to give the title compound as a white powder (2.3 g; 82%). HPLC, Rt: 1.75 min. (purity 94.8%). LC/MS, M⁺(ESI): 217.3.

Intermediate A2

5-(3-furyl)[1,2,4]triazolo[1,5-a]pyridin-2-amine

Step a) Formation of 6-(3-furyl)pyridin-2-amine

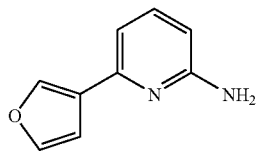

The title compound was prepared following procedure described for intermediate A1 step a), but starting from 2-amino-6-chloropyridine (25.0 g; 194.5 mmol; 1.0 eq.) and furan-3-boronic acid (26.11 g; 233.4 mmol; 1.2 eq.). The crude was purified by flash chromatography (EtOAc/c-Hex, 50:50) to give the title compound as a brown oil (16.91 g; 54%). ¹H NMR (DMSO-d₆) δ 7.96 (s, 1H), 7.42 (m, 2H), 6.82 (m, 2H), 6.37 (d, J=7.2 Hz, 1H), 4.54 (m, 2H). HPLC, Rt: 1.30 min. (purity 84.9%). LC/MS, M⁺(ESI): 161.4.

Step b) Formation of ethyl({[6-(3-furyl)pyridin-2-yl]amino}carbonothioyl)carbamate

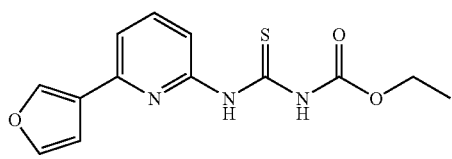

The title compound was prepared following procedure described for intermediate A1 step b), but starting from 6-(3-furyl)pyridin-2-amine (16.0 g; 105.5 mmol; 1.0 eq.) as a white solid (28.2 g; 92%). HPLC, Rt: 3.98 min. (purity 99.7%). LC/MS, M⁺(ESI): 292.3, M⁻(ESI): 290.2.

Step c) Formation of
5-(3-furyl)[1,2,4]triazolo[1,5-a]pyridin-2-amine

Intermediate A2

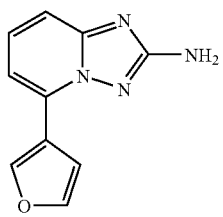

The title compound was prepared following procedure described for intermediate A1 step c), but starting from ethyl ({[6-(3-furyl)pyridin-2-yl]amino}carbonothioyl)carbamate (28.1 g; 96.5 mmol; 1.0 eq.) as a clear beige powder (17.26 g; 89%). ¹H NMR (DMSO-d₆) δ 8.92 (s, 1H), 7.88 (d, J=1.7 Hz, 1H), 7.50 (t, J=8.1 Hz, 1H), 7.29-7.37 (m, 3H), 6.11 (s, 2H). HPLC, Rt: 1.59 min. (purity 99.6%). LC/MS, M⁺(ESI): 201.3.

Intermediate A3

5-bromo[1,2,4]triazolo[1,5-a]pyridin-2-amine

Step a) Formation of ethyl {[(6-bromopyridin-2-yl)amino]carbonothioyl}carbamate

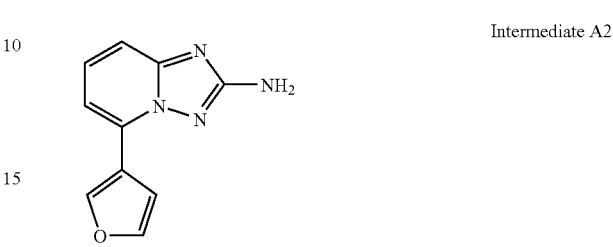

The title compound was prepared following procedure described for intermediate A1 step b), but starting from 2-amino-6-bromopyridine (20.0 g; 115.6 mmol; 1.0 eq.) as a white solid (36 g, quant. yield). HPLC, Rt: 4.17 min. (purity 99.8%). LC/MS, M⁺(ESI): 306.1.

Step b) Formation of
5-bromo[1,2,4]triazolo[1,5-a]pyridin-2-amine

Intermediate A3

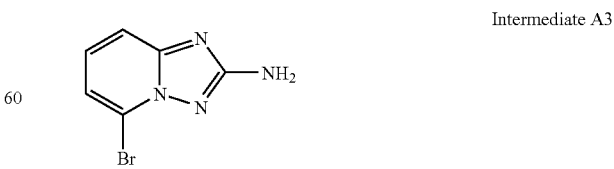

The title compound was prepared following procedure described for intermediate A1 step c), but starting from ethyl {[(6-bromopyridin-2-yl)amino]carbonothioyl}carbamate (36.0 g; 118.4 mmol; 1.0 eq.) as a yellowish solid (20.65 g; 82%). HPLC, Rt: 1.03 min. (purity 97.6%). LC/MS, M⁺(ESI): 215.2.

Intermediate A4

5-chloro[1,2,4]triazolo[1,5-a]pyridin-2-amine

Step a) formation of ethyl {[(6-chloropyridin-2-yl)amino]carbonothioyl}carbamate

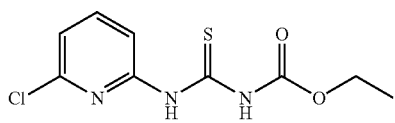

The title compound was prepared following procedure described for intermediate A1 step b), but starting from 2-amino-6-chloropyridine (49.38 g; 384.1 mmol; 1.0 eq.) as a yellow solid (107 g, quant. yield). HPLC, Rt: 3.93 min. (purity 94.5%). LC/MS, M⁺(ESI): 260.0.

Step b) formation of 5-chloro[1,2,4]triazolo[1,5-a]pyridin-2-amine

Intermediate A4

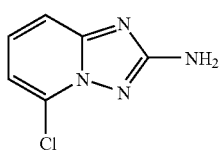

The title compound was prepared following procedure described for intermediate A1 step c), but starting from ethyl {[(6-chloropyridin-2-yl)amino]carbonothioyl}carbamate (99.76 g; 384.1 mmol; 1.0 eq.) as a greenish solid (51.19 g; 79.0%). HPLC, Rt: 0.92 min. (purity 98.1%). LC/MS, M⁺(ESI): 169.0.

Intermediate A5

6-bromo[1,2,4]triazolo[1,5-a]pyridin-2-amine

Step a) Formation of ethyl {[(5-bromopyridin-2-yl)amino]carbonothioyl}carbamate

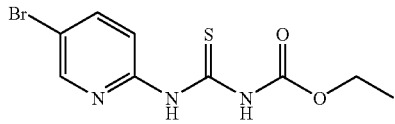

The title compound was prepared following procedure described for intermediate A1 step b), but starting from 2-amino-5-bromopyridine (35.0 g; 202.3 mmol; 1.0 eq.) as a yellowish solid (60 g; 97%). HPLC, Rt: 4.04 min. (purity 92.4%). LC/MS, M⁺(ESI): 305.9.

Step b) Formation of 6-bromo[1,2,4]triazolo[1,5-a]pyridin-2-amine

Intermediate A5

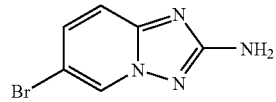

The title compound was prepared following procedure described for intermediate A1 step c), but starting from ethyl {[(5-bromopyridin-2-yl)amino]carbonothioyl}carbamate (61.0 g; 200.6 mmol; 1.0 eq.) as an off white powder (42.6 g; 99%). HPLC, Rt: 1.18 min. (purity 97.3%). LC/MS, M⁺(ESI): 214.9.

Intermediate A6 tert-butyl 2-(2-amino[1,2,4]triazolo[1,5-a]pyridin-5-yl)-1H-pyrrole-1-carboxylate Step a) Formation of tert-butyl 2-(6-aminopyridin-2-yl)-1H-pyrrole-1-carboxylate

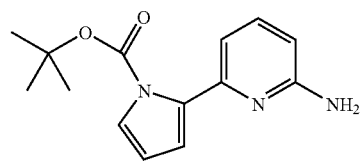

The title compound was prepared following procedure described for intermediate A1 step a), but starting from 2-amino-6-chloropyridine (2.05 g; 16.0 mmol; 1.0 eq.) and ethyl 1-(t-butoxycarbonyl)pyrrole-2-boronic acid (5.06 g; 24.0 mmol; 1.5 eq.) as a beige powder (1.15 g, 27%). HPLC, Rt: 2.65 min. (purity 97.0%). LC/MS, M⁺(ESI): 204.3.

Step b) Formation of tert-butyl 2-[6-({[(ethoxycarbonyl)amino]carbonothioyl}amino)pyridin-2-yl]-1H-pyrrole-1-carboxylate

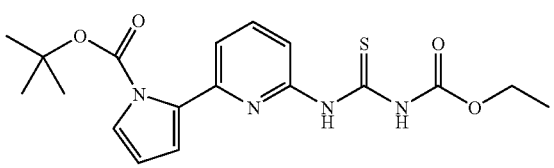

The title compound was prepared following procedure described for intermediate A1 step b), but starting from tert-butyl 2-(6-aminopyridin-2-yl)-1H-pyrrole-1-carboxylate (1.15 g; 4.43 mmol; 1.0 eq.) as a beige solid (1.47 g, 85%). HPLC, Rt: 4.99 min. (purity 94.0%). LC/MS, M⁺(ESI): 335.2.

Step c) Formation of tert-butyl 2-(2-amino[1,2,4] triazolo[1,5-a]pyridin-5-yl)-1H-pyrrole-1-carboxylate

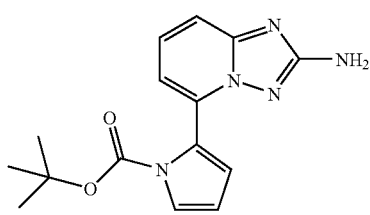

Intermediate A6

The title compound was prepared following procedure described for intermediate A1 step c), but starting from tert-butyl 2-[6-({[(ethoxycarbonyl)amino]carbonothioyl}amino)pyridin-2-yl]-1H-pyrrole-1-carboxylate (1.47 g; 3.76 mmol; 1.0 eq.) as a beige solid (870 mg, 77%). HPLC, Rt: 2.68 min. (purity 98.5%). LC/MS, M⁺(ESI): 244.3.

Intermediate A7

5-chloro-7-(trifluoromethyl)[1,2,4]triazolo[1,5-a]pyridin-2-amine

Step a) Formation of 6-chloro-4-(trifluoromethyl)pyridin-2-amine

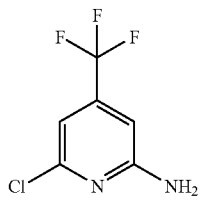

A solution of 2,6-dichloro-4-(trifluoromethylpyridine) (Fluorochem, 10.0 g; 46.30 mmol; 1.0 eq.) in ammonium hydroxide (~25% in water) (40.0 mL; 4.0 V) was heated to 180° C. for 3 h in a Parr apparatus and cooled down to rt. After this time, reaction mixture was filtered over a bed of celite, evaporated to dryness under reduced pressure, triturated with DCM and filtered. The mother liquors were concentrated under reduced pressure to give the title compound as a yellow oil that crystallized upon standing (4.83 g; 53%). HPLC, Rt: 3.58 min. (purity 96.9%). LC/MS, M⁺(ESI): 196.8, M⁻(ESI): 194.8.

Step b) formation of ethyl({[6-chloro-4-(trifluoromethyl)pyridin-2-yl]amino}carbonothioyl)carbamate

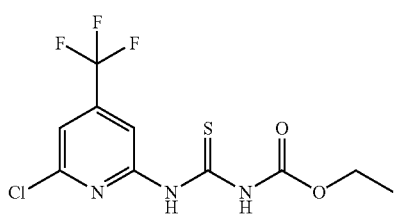

The title compound was prepared following procedure described for intermediate A1 step b), but starting from 6-chloro-4-(trifluoromethyl)pyridin-2-amine (4.83 g; 24.57 mmol; 1.0 eq.) as a beige solid (6.90 g; 86%). HPLC, Rt: 5.00 min. (purity 96.0%). LC/MS, M⁺(ESI): 327.9.

Step c) Formation of 5-chloro-7-(trifluoromethyl)[1,2,4]triazolo[1,5-a]pyridin-2-amine

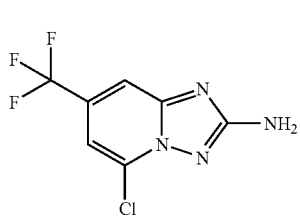

Intermediate A7

The title compound was prepared following procedure described for intermediate A1 step c), but starting from ethyl ({[6-chloro-4-(trifluoromethyl)pyridin-2-yl]amino}carbonothioyl)carbamate (6.90 g; 21.1 mmol; 1.0 eq.) as a white powder (3.6 g, 72%). HPLC, Rt: 2.45 min. (purity 98.9%). LC/MS, M⁺(ESI): 236.8, M⁻(ESI): 234.8.

Intermediate A8

6-bromo-5-methyl[1,2,4]triazolo[1,5-a]pyridin-2-amine

Step a) Formation of ethyl {[(5-bromo-6-methylpyridin-2-yl)amino]carbonothioyl}carbamate

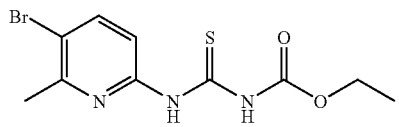

The title compound was prepared following procedure described for intermediate A1 step b), but starting from 6-amino-3-bromo-2-methylpyridine (25.0 g; 133.7 mmol; 1.0 eq.) as a yellow powder (41.80 g; 98%). HPLC, Rt: 4.49 min. (purity 99.3%). LC/MS, M⁺(ESI): 319.9, M⁻(ESI): 317.9.

Step b) Formation of 6-bromo-5-methyl[1,2,4]triazolo[1,5-a]pyridin-2-amine

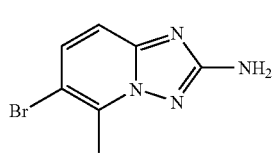

Intermediate A8

The title compound was prepared following procedure described for intermediate A1 step c), but starting from ethyl {[(5-bromo-6-methylpyridin-2-yl)amino]carbonothioyl}carbamate (41.8 g; 131.4 mmol; 1.0 eq.) as a white solid (23.90 g; 80%). HPLC, Rt: 1.55 min. (purity 99.9%). LC/MS, M+(ESI): 228.9.

Intermediate A9

N5-cyclohexyl[1,2,4]triazolo[1,5-a]pyridine-2,5-diamine

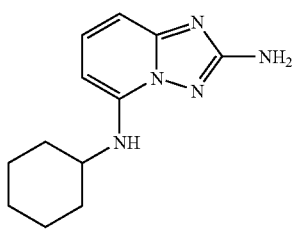

Intermediate A9

A suspension of 5-chloro[1,2,4]triazolo[1,5-a]pyridin-2-amine ((A4), 10.0 g; 59.32 mmol; 1.0 eq.) in cyclohexylamine (60 mL) was heated to reflux for 52 h. Reaction mixture was taken up in MTBE and filtered. The resulting cake was washed with MTBE and filtrate was concentrated to dryness. Residue was purified by flash chromatography (Hept/EtOAc, 1:1) to give the title compound as a beige powder (8.08 g, 59%). HPLC, Rt: 2.46 min. (purity 98.9%). LC/MS, M+(ESI): 231.9.

Intermediate A10

N5-cycloheptyl[1,2,4]triazolo[1,5-a]pyridine-2,5-diamine

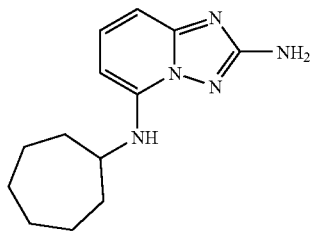

Intermediate A10

The title compound was prepared following procedure described for intermediate A9, but starting from 5-chloro[1,2,4]triazolo[1,5-a]pyridin-2-amine ((A4), 2.88 g; 17.1 mmol; 1.0 eq.) and cycloheptylamine (14 mL) and heated at 180° C. for 1 h under microwave radiation to give the title compound as a beige oil (2.48 g; 59%). HPLC, Rt: 2.90 min. (purity 97.2%). LC/MS, M+(ESI): 292.9.

Intermediate A11

5-(cyclohexyloxy)[1,2,4]triazolo[1,5-a]pyridin-2-amine

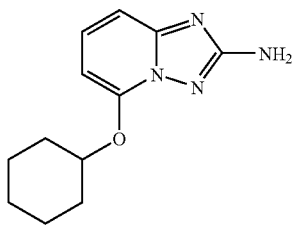

Intermediate A11

Cyclohexanol (1.68 mL; 15.84 mmol; 5.0 eq.) was added to a suspension of NaH (152 mg; 3.80 mmol; 1.2 eq.) in THF (6.0 mL) and maintained under inert atmosphere at 0° C. The reaction mixture was brought back to rt and stirred for 1 h before the addition of 5-chloro[1,2,4]triazolo[1,5-a]pyridin-2-amine ((A4), 534 mg; 3.17 mmol; 1.0 eq.). Reaction mixture was then heated at reflux for 3 h after which time it was quenched by addition of water. It was then extracted with EtOAc, washed with brine, dried over magnesium sulfate, filtered and concentrated. Purification by flash chromatography on silica gel (DCM/MeOH, 95:5 to 10:90) gave the title compound as a white solid (590 mg, 80%). HPLC, Rt: 2.18 min. (purity 90.1%). LC/MS, M+(ESI): 233.0.

Intermediate A12

5-(1H-pyrazol-1-yl)[1,2,4]triazolo[1,5-a]pyridin-2-amine

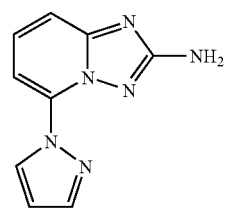

Intermediate A12

5-bromo[1,2,4]triazolo[1,5-a]pyridin-2-amine ((A3); 1.06 g; 5.0 mmol; 1.0 eq.), pyrazole (3.40 g; 50.0 mmol; 10 eq.) and potassium hydroxide (842 mg; 15.0 mmol; 3.0 eq.) were melted and stirred overnight at 110° C. After this time, reaction mixture was cooled to rt poured into water and extracted with Et2O. The combined organic layers were washed with water, dried over magnesium sulfate, filtered and evaporated under reduced pressure to give the title compound as a white solid (650 mg, 65%). HPLC, Rt: 1.22 min. (purity 96.6%). LC/MS, M+(ESI): 201.0.

Intermediate A13

[1,2,4]triazolo[1,5-a]quinolin-2-amine

Step a) Formation of ethyl[(quinolin-2-ylamino)carbonothioyl]carbamate

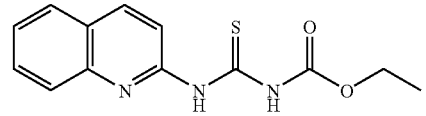

The title compound was prepared following procedure described for intermediate A1 step b), but starting from quinolin-2-amine (1.06 g; 7.35 mmol; 1.0 eq.) as a yellow powder (1.68 g, 83%). HPLC, Rt: 3.66 min. (purity 97.8%). LC/MS, M−(ESI): 274.3.

Step b) Formation of [1,2,4]triazolo[1,5-a]quinolin-2-amine

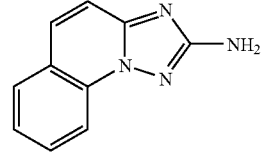

Intermediate A13

The title compound was prepared following procedure described for intermediate A1 step c), but starting from ethyl

[(quinolin-2-ylamino)carbonothioyl]carbamate (1.68 g; 6.10 mmol; 1.0 eq.) as a white powder (667 mg, 59%). ¹H NMR (DMSO-d₆) δ 8.26 (d, J=8.3 Hz, 1H), 7.81 (d, J=7.9 Hz, 1H), 7.74 (d, J=9.4 Hz, 1H), 7.70 (m, 1H), 7.47 (m, 1H), 7.45 (d, J=9.0 Hz, 1H). HPLC, Rt: 1.62 min. (purity 99.7%). LC/MS, M⁺(ESI): 185.4.

Intermediate A14

6-bromo-N⁵-cyclohexyl[1,2,4]triazolo[1,5-a]pyridine-2,5-diamine

Step a) Formation of 5-bromo-6-chloropyridin-2-amine

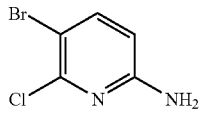

N-bromosuccinimide (16.45 g; 92.41 mmol; 1.10 eq.) was added portionwise to a solution of 2-amino-6-chloropyridine (10.80 g; 84.01 mmol; 1.0 eq.) in DMF (200 mL) at rt. The reaction mixture was stirred at rt for 2 hours. Solvents were removed under reduced pressure and the residue was taken up in EtOAc and aqueous ammonia. The organic phase was washed again with aqueous ammonia and brine, dried over magnesium sulfate, filtered and concentrated under reduced pressure. The black solid obtained was washed with pentane and dried under vacuum to give the title compound as a beige powder (12.5 g, 72%). HPLC, Rt: 2.81 min. (purity 95.8%).

Step b) Formation of ethyl {[(5-bromo-6-chloropyridin-2-yl)amino]carbonothioyl}carbamate

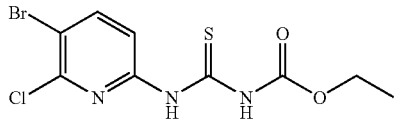

The title compound was prepared following procedure described for intermediate A1 step b), but starting from 5-bromo-6-chloropyridin-2-amine (7.09 g; 34.2 mmol; 1.0 eq.) as an off-white solid (8.80 g; 76%). HPLC, Rt: 4.65 min. (purity 100.0%).

Step c) Formation of 6-bromo-5-chloro[1,2,4]triazolo[1,5-a]pyridin-2-amine

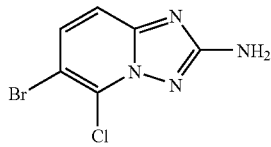

The title compound was prepared following procedure described for intermediate A1 step c), but starting from ethyl {[(5-bromo-6-chloropyridin-2-yl)amino]carbonothioyl}carbamate (8.80 g; 26.0 mmol; 1.0 eq.) as a beige powder (4.56 g; 70%). HPLC, Rt: 1.96 min. (purity 91.5%). LC/MS, M⁺(ESI): 248.8.

Step d) Formation of 6-bromo-N⁵-cyclohexyl[1,2,4]triazolo[1,5-a]pyridine-2,5-diamine

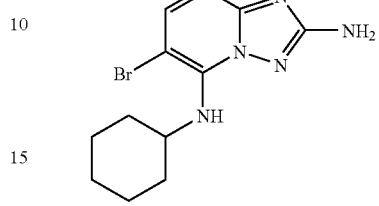

Intermediate A14

The title compound was prepared following procedure described for intermediate A9 but starting from 6-bromo-5-chloro[1,2,4]triazolo[1,5-a]pyridin-2-amine (3.0 g; 12.1 mmol; 1.0 eq.) and cyclohexylamine (12.0 mL; 104.9 mmol; 8.65 eq.) to give the title compound as a dark foam (2.5 g, 66%). HPLC, Rt: 3.21 min. (purity 76.6%). LC/MS, M⁺(ESI): 310.0.

Intermediate A15

6-bromo-N⁵-cyclohexyl[1,2,4]triazolo[1,5-a]pyridine-2,5-diamine

Step a) Formation of ethyl {[(3-bromopyridin-2-yl)amino]carbonothioyl}carbamate

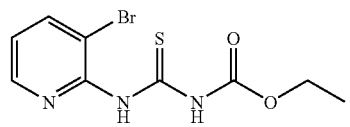

The title compound was prepared following procedure described for intermediate A1, step b) but starting from 2-amino-3-bromopyridine (4.18 g; 24.16 mmol; 1.0 eq.) to give the title compound as a light yellowish powder (7.4 g, quant. yield). HPLC, Rt: 2.72 min. (purity 99.7%). LC/MS, M⁺(ESI): 303.9.

Step b) Formation of 8-bromo[1,2,4]triazolo[1,5-a]pyridin-2-amine

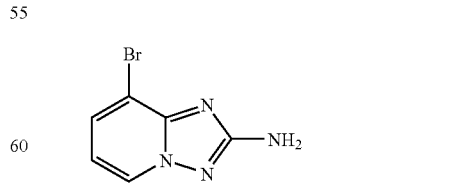

Intermediate A15

The title compound was prepared following procedure described for intermediate A1, step c) but starting from ethyl {[(3-bromopyridin-2-yl)amino]carbonothioyl}carbamate (7.40 g; 24.33 mmol; 1.0 eq.) to give the title compound as a white solid (4.4 g, 85%). HPLC, Rt: 1.16 min. (purity 99.8%). LC/MS, M⁺(ESI): 212.9, 214.9.

Intermediate A16

5-(2-furyl)[1,2,4]triazolo[1,5-a]pyridin-2-amine

Step a) Formation of 6-(2-furyl)pyridin-2-amine

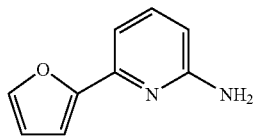

The title compound was prepared following procedure described for intermediate A1 step a), but starting from 2-amino-6-chloropyridine (925.64 mg; 7.20 mmol; 1.0 eq.) and 2-furanboronic acid (1.21 g; 10.8 mmol; 1.5 eq.). The crude was purified by flash chromatography (EtOAc/c-Hex, gradient from 25:75 to 40:60) to give the title compound (990 mg; 86%). HPLC, Rt: 1.33 min. (purity 99.9%). LC/MS, M⁺(ESI): 161.0.

Step b) Formation of ethyl({[6-(2-furyl)pyridin-2-yl]amino}carbonothioyl)carbamate

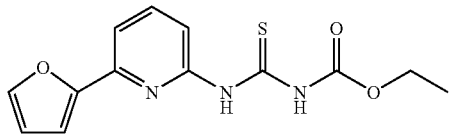

The title compound was prepared following procedure described for intermediate A1 step b), but starting from 6-(2-furyl)pyridin-2-amine (970 mg; 6.06 mmol; 1.0 eq.) as a white solid (1.67 g; 94%). HPLC, Rt: 4.07 min. (purity 98.4%). LC/MS, M⁺(ESI): 292.0, M⁻(ESI): 290.1.

Step c) Formation of 5-(2-furyl)[1,2,4]triazolo[1,5-a]pyridin-2-amine

Intermediate A16

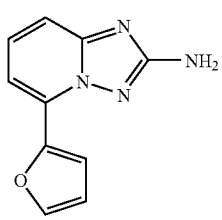

The title compound was prepared following procedure described for intermediate A1 step c), but starting from ethyl ({[6-(2-furyl)pyridin-2-yl]amino}carbonothioyl)carbamate (1.65 g; 5.66 mmol; 1.0 eq.) as a white powder (1.13 g; 99%). HPLC, Rt: 1.75 min. (purity 98.4%). LC/MS, M⁺(ESI): 201.1.

Intermediate A17

N⁵-isopropyl-7-(trifluoromethyl)[1,2,4]triazolo[1,5-a]pyridine-2,5-diamine

Intermediate A17

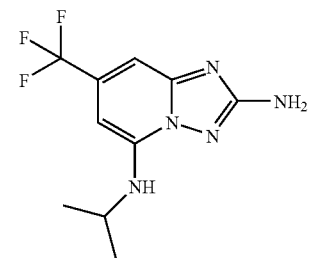

A suspension of 5-chloro-7-(trifluoromethyl)[1,2,4]triazolo[1,5-a]pyridin-2-amine ((A7), 183.00 mg; 0.77 mmol; 1.00 eq.) and isopropylamine (664.58 μl; 7.74 mmol; 10.00 eq.) in n-butanol (1.50 mL) was heated at 120° C. for 1 h30 under MW irradiation. The reaction mixture was then concentrated under vacuum till dryness. The solid obtained was triturated in water/MTBE and filtered. The solid which precipitated in mother liquor was finally filtered, washed with water and dried under vacuum at 40° C. to give the title compound as an off-white solid (122 mg, 61%). HPLC, Rt: 2.64 min. (purity 86.5%). LC/MS, M⁺(ESI): 259.9, M⁻(ESI): 257.9.

Intermediate A18

N⁵-cyclopropyl-7-(trifluoromethyl)[1,2,4]triazolo[1,5-a]pyridine-2,5-diamine

Intermediate A18

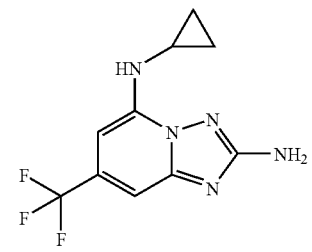

A suspension of 5-chloro-7-(trifluoromethyl)[1,2,4]triazolo[1,5-a]pyridin-2-amine ((A7), 3.60 g; 15.22 mmol; 1.0 eq.), cyclopropylamine (5.27 mL; 76.1 mmol; 5.0 eq.), and N-ethyldiisopropylamine (26.22 mL; 152.2 mmol; 10.0 eq.) was heated at 80° C. in 1-butanol (36.0 mL) for 23 h., then 15 h. at 100° C. The reaction mixture was then concentrated under vacuum till dryness. Diethyl ether was added and the solid was filtered, washed with water and dried. The product was then purified by chromatography on silicagel (from 5% to 95% EtOAc in c-Hex), to give the title compound as a white solid (2.0 g; 51.1%). HPLC, Rt: 2.54 min. (purity 100%). LC/MS, M⁺(ESI): 258.0, M⁻(ESI): 256.0.

Intermediate A19

5-chloro-7-methyl[1,2,4]triazolo[1,5-a]pyridin-2-amine

Step a) Formation of 6-Chloro-4-methylpyridin-2-amine

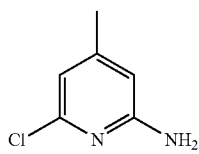

A solution of 2,6-Dichloro-4-methylpyridine (Chem. Mater., 2004, 16, 1564-1572, 30 g, 0.185 mol) in ammonium hydroxide (200 mL, 25% solution in water) was heated at 200° C. in a pressure vessel for 10 h. The reaction mixture was then concentrated under reduced pressure. The brown solid obtained was suspended in DCM for 30 min at 25-26° C. and filtered. Filtrate was concentrated under reduced pressure. Purification of the crude thus obtained by flash chromatography (20% ethyl acetate in pet ether) afforded the title compound as off-white solid (13.5 g, Yield 51%). LC/MS: M⁺(ESI): 142.7; ¹H NMR (DMSO d₆: 400 MHz) δ 6.34 (1H, s), 6.23 (2H, s), 6.15 (1H, s), 2.1 (3H, s).

Step b) Formation of ethyl {[(6-chloro-4-methylpyridin-2-yl)amino]carbonothioyl}carbamate

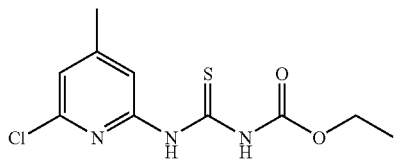

The title compound was prepared following procedure described for intermediate A1 step b), but starting from 2-amino-4,6-dichloropyridine (2.5 g; 15.3 mmol; 1.0 eq.) as an off-white solid (5.0 g; 64%). HPLC, Rt: 4.36 min. (purity 98.3%). LC/MS, M⁺(ESI): 273.8, M⁻(ESI): 271.8.

Step c) Formation of 5-chloro-7-methyl[1,2,4]triazolo[1,5-a]pyridin-2-amine

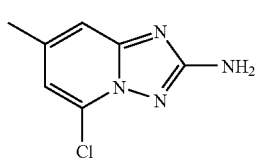

Intermediate A19

The title compound was prepared following procedure described for intermediate A1 step c), but starting from ethyl {[(6-chloro-4-methylpyridin-2-yl)amino]carbonothioyl}carbamate (5.0 g; 18.4 mmol; 1.0 eq.) as a white solid (3.34 g; 99.5%). HPLC, Rt: 1.17 min. (purity 92.8%). LC/MS, M⁺(ESI): 282.8.

Intermediate B

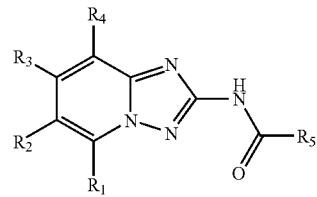

Intermediate B1

N-(5-bromo[1,2,4]triazolo[1,5-a]pyridin-2-yl)benzamide

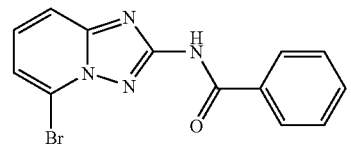

Intermediate B1

Benzoyl chloride (4.40 g; 31.4 mmol; 2.0 eq.) was added to a suspension of 5-bromo[1,2,4]triazolo[1,5-a]pyridin-2-amine ((A3), 3.34 g; 15.7 mmol; 1.0 eq.) in pyridine (2.53 mL; 31.4 mmol; 2.0 eq.) and DCM (60 mL). The reaction mixture was then heated at reflux for 4 hours, after which it was cooled down to rt. Diethyl ether was added to the reaction mixture and the solid which precipitated was filtered off. The precipitate was resuspended in an aqueous mixture (pH 4/5), filtered and dried under vacuum to give the title compound as a white powder (4.97 g, quant. yield). HPLC, Rt: 2.40 min. (purity 93.4%), LC/MS, M⁺(ESI): 317.1, M⁻(ESI): 315.1.

Intermediate B2

N-(5-bromo[1,2,4]triazolo[1,5-a]pyridin-2-yl)nicotinamide

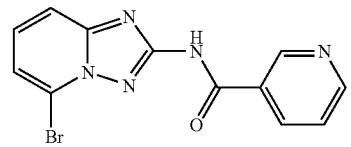

Intermediate B2

The title compound was prepared following procedure described for intermediate B1, but starting from 5-bromo[1,2,4]triazolo[1,5-a]pyridin-2-amine ((A3), 5.0 g; 23.5 mmol; 1.0 eq.) and nicotinoyl chloride hydrochloride (8.36 g; 47.0 mmol; 2.0 eq.) as a grey powder (5.86 g, 78%). HPLC, Rt: 1.24 min. (purity 97.4%). LC/MS, M⁺(ESI): 319.0, M⁻(ESI): 318.3.

Intermediate B3

N-(5-chloro[1,2,4]triazolo[1,5-a]pyridin-2-yl)benzamide

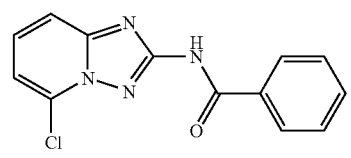

Intermediate B3

The title compound was prepared following procedure described for intermediate B1, but starting from 5-chloro[1, 2,4]triazolo[1,5-a]pyridin-2-amine ((A4), 84.29 mg; 0.50 mmol; 1.0 eq.) and benzoyl chloride (70 mg; 0.50 mmol; 1.0 eq.) as a white powder (136 mg, quant. yield). HPLC, Rt: 2.30 min. (purity 99.0%). LC/MS, M⁺(ESI): 273.0.

Intermediate B4

N-(5-chloro[1,2,4]triazolo[1,5-a]pyridin-2-yl)nicotinamide

Intermediate B4

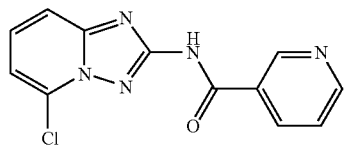

The title compound was prepared following procedure described for intermediate B1, but starting from 5-chloro[1,2,4]triazolo[1,5-a]pyridin-2-amine ((A4), 14.60 g; 86.60 mmol; 1.0 eq.) and nicotinoyl chloride hydrochloride (18.5 g; 104 mmol; 1.2 eq.) as a greenish solid (20.61 g; 87%). HPLC, Rt: 1.19 min. (purity 99.4%). LC/MS, M⁺(ESI): 274.3, M⁺(ESI): 272.3.

Intermediate B5

N-(6-bromo[1,2,4]triazolo[1,5-a]pyridin-2-yl)benzamide

Intermediate B5

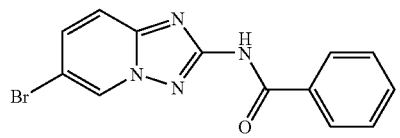

The title compound was prepared following procedure described for intermediate B1, but starting from 6-bromo[1,2,4]triazolo[1,5-a]pyridin-2-amine ((A5), 5.0 g; 23.47 mmol; 1.0 eq.) and benzoyl chloride (6.57 g; 46.9 mmol; 2.0 eq.) as a white powder (6.5 g, 87%). HPLC, Rt: 2.49 min. (purity 97.1%). LC/MS, M⁺(ESI): 317.0, M⁻(ESI): 316.9.

Intermediate B6

N-(6-bromo[1,2,4]triazolo[1,5-a]pyridin-2-yl)nicotinamide hydrochloride

Intermediate B6

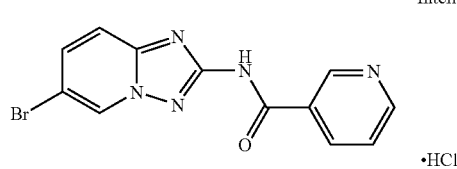

The title compound was prepared following procedure described for intermediate B1, but starting from 6-bromo[1,2,4]triazolo[1,5-a]pyridin-2-amine ((A5), 5.0 g; 23.5 mmol; 1.0 eq.) and nicotinoyl chloride hydrochloride (5.01 g; 28.2 mmol; 1.2 eq.) as a light yellow solid (6.30 g; 84%). HPLC, Rt: 1.32 min. (purity 99.6%). LC/MS, M⁺(ESI): 317.9. CHN analysis: [C₁₂H₈N₅OBr.1.0 HCl.1.0 H₂O] Corrected: C, 38.68%; H, 2.98%; N 18.80%. Found: C, 38.76%; H, 3.11%; N, 18.66%.

Intermediate B7

N-[5-chloro-7-(trifluoromethyl)[1,2,4]triazolo[1,5-a]pyridin-2-yl]nicotinamide

Intermediate B7

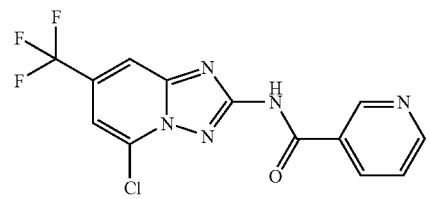

The title compound was prepared following procedure described for intermediate B1, but starting from 5-chloro-7-(trifluoromethyl)[1,2,4]triazolo[1,5-a]pyridin-2-amine ((A7), 2.72 g; 11.5 mmol; 1.0 eq.) and nicotinoyl chloride hydrochloride (2.46 g; 13.8 mmol; 1.2 eq.) as a greenish solid (1.42 g; 36%). HPLC, Rt: 2.16 min. (purity 100%). LC/MS, M⁺(ESI): 342.2, M⁻(ESI): 340.2.

Intermediate B8

4-(chloromethyl)-N-[5-(cyclohexylamino)[1,2,4]triazolo[1,5-a]pyridin-2-yl]benzamide Intermediate B8

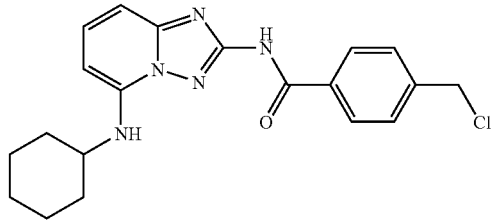

The title compound was prepared following procedure described for intermediate B1, but starting from N⁵-cyclohexyl[1,2,4]triazolo[1,5-a]pyridine-2,5-diamine ((A9), 800 mg; 3.46 mmol; 1.0 eq.) and 4-(chloromethyl)benzoyl chloride (981 mg; 5.2 mmol; 1.5 eq.) as a brownish foam (1.32 g, 99%). LC/MS, M⁺(ESI): 384.0, M⁻(ESI): 382.0.

Intermediate B9

N-(8-bromo[1,2,4]triazolo[1,5-a]pyridin-2-yl)benzamide

Intermediate B9

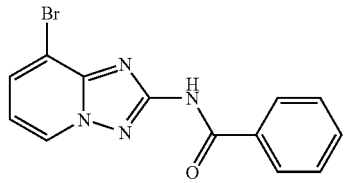

The title compound was prepared following procedure described for intermediate B1, but starting from 8-bromo[1, 2,4]triazolo[1,5-a]pyridin-2-amine ((A15), 4.40 g; 20.7 mmol; 1.0 eq.) and benzoyl chloride (5.81 g; 41.3 mmol; 2.0 eq.) as a white solid (4.9 g, 74%). HPLC, Rt: 2.45 min. (purity 90.1%). LC/MS, M⁺(ESI): 318.9, M⁻(ESI): 316.9.

Intermediate B10

N-(5,7-dichloro[1,2,4]triazolo[1,5-a]pyridin-2-yl)nicotinamide

Step a) Formation of ethyl {[(4,6-dichloropyridin-2-yl)amino]carbonothioyl}carbamate

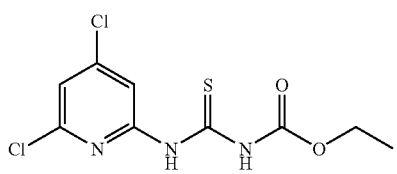

The title compound was prepared following procedure described for intermediate A1 step b), but starting from 2-amino-4,6-dichloropyridine (J&W Pharma, 2.50 g; 15.34 mmol; 1.00 eq.) as a white solid (4.27 g; 94%). HPLC, Rt: 4.68 min. (purity 100%).

Step b) Formation of 5,7-dichloro[1,2,4]triazolo[1,5-a]pyridin-2-amine

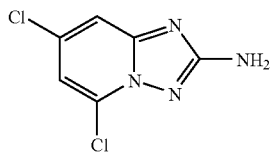

The title compound was prepared following procedure described for intermediate A1 step c), but starting from ethyl {[(4,6-dichloropyridin-2-yl)amino]carbonothioyl}carbamate (4.27 g; 14.52 mmol; 1.00 eq.) as a white solid (2.61 g; 88%). HPLC, Rt: 1.78 min (purity 97.9%). LC/MS, M⁺(ESI): 202.8.

Step c) Formation of N-(5,7-dichloro[1,2,4]triazolo[1,5-a]pyridin-2-yl)nicotinamide

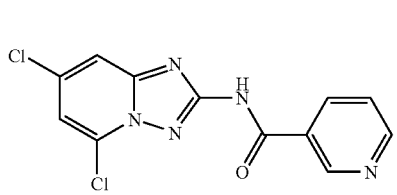

Intermediate B10

The title compound was prepared following procedure described for intermediate B1, but starting from 5,7-dichloro[1,2,4]triazolo[1,5-a]pyridin-2-amine (1.00 g; 4.93 mmol; 1.00 eq.) and nicotinoyl chloride hydrochloride (1052.16 mg; 5.91 mmol; 1.20 eq.) as a yellowish solid (1.06 g, 70%). HPLC, Rt 1.61 min. (purity 92.4%). LC/MS, M⁺(ESI): 307.7, M⁻(ESI): 305.8.

Intermediate B11

6-chloro-N-[5-(cyclohexylamino)[1,2,4]triazolo[1,5-a]pyridin-2-yl]nicotinamide

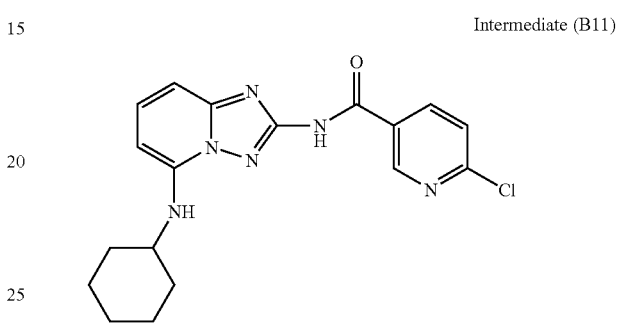

Intermediate (B11)

To a reaction vessel containing N-5-cyclohexyl-[1,2,4]triazolo[1,5-a]pyridine-2,5-diamine (500 mg, 2.16 mmol, 1 eq.) and triethylamine (0.75 mL, 5.40 mmol, 2.5 eq.) in acetonitrile (8 mL) was added 6-chloronicotinyl chloride (952 mg, 5.40 mmol, 2.5 eq.) in acetonitrile (2 mL), dropwise. The vessel was capped and stirred at room temperature for 16 hours. The solvent was removed in vacuo and the resulting solid dissolved in methanolic ammonia (15 mL, 7 N) and stirred at room temperature for a further 24 hours. The solvent was removed in vacuo and the solid dissolved in ethyl acetate (40 mL). The organic phase was washed with water (3×20 mL), dried (MgSO₄) and concentrated. The resulting solid was triturated with dichloromethane and filtered to give the title compound as a white solid (250 mg, 31%). No further purification carried out.

Intermediate B12

N-(5-chloro-7-methyl[1,2,4]triazolo[1,5-a]pyridin-2-yl)nicotinamide

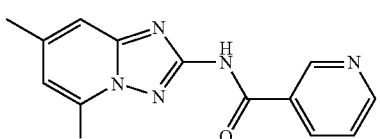

Intermediate B12

The title compound was prepared following procedure described for intermediate B1, but starting from 5-chloro-7-methyl[1,2,4]triazolo[1,5-a]pyridin-2-amine (282 mg; 1.54 mmol; 1.0 eq.) and nicotinoyl chloride hydrochloride (330 mg; 1.85 mmol; 1.20 eq.) as a off-white powder (244 mg, 55%). HPLC, Rt: 1.51 min. (purity 90.4%). LC/MS, M+(ESI): 288.1, M−(ESI): 286.2.

Example 1

N-[5-(3-furyl)[1,2,4]triazolo[1,5-a]pyridin-2-yl]-2-phenylacetamide

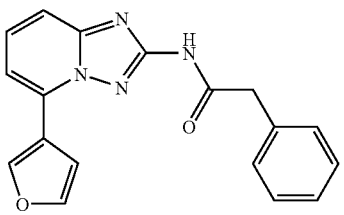

(1)

The title compound was prepared following procedure described for intermediate B1, but starting from 5-(3-furyl)[1,2,4]triazolo[1,5-a]pyridin-2-amine ((A2), 41 mg; 0.20 mmol; 1.0 eq.) and phenylacetyl chloride (38 µl; 0.41 mmol; 2.0 eq). Purification of the compound by flash chromatography on silica (EtOAc/c-Hex, 50:50) gave the title compound as a white powder (21 mg, 29%). $^1$H NMR (DMSO-d$_6$) δ 8.98 (brs, 1H), 8.61 (brs, 1H), 7.55 (m, 3H), 7.37 (m, 5H), 7.22 (m, 1H), 6.91 (s, 1H), 3.96 (brs, 2H), 1.99 (brs, 3H, water). HPLC, Rt: 3.27 min. (purity 94.5%). LC/MS, M+(ESI): 319.3, M−(ESI): 317.3.

Example 2

N-[5-(3-furyl)[1,2,4]triazolo[1,5-a]pyridin-2-yl]nicotinamide

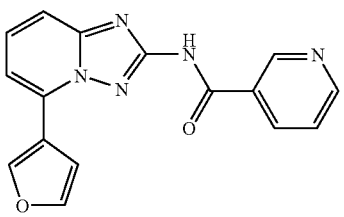

(2)

A solution of nicotinic acid (74 mg, 0.6 mmol, 1.2 eq.) and 1,1-carbonyldiimidazole (122 mg, 0.75 mmol, 1.5 eq.) in dry THF (1 mL) was stirred for 45 min. at rt. In parallel, a solution of 5-(3-furyl)[1,2,4]triazolo[1,5-a]pyridin-2-amine ((A2), 100 mg; 0.50 mmol; 1.0 eq.) and sodium tert-butoxide (96 mg, 1.0 mmol, 2.0 eq.) in dry THF (2 mL) was stirred for 45 min. at rt. The two solutions were then combined and the reaction mixture was stirred overnight at rt. Et$_2$O was then added and the precipitate obtained was filtered, washed with Et$_2$O, THF, a 5N solution of NaOH and water. It was resuspended in an acidic aqueous solution (pH 1) and filtered to give the title compound as a white powder (52.4 mg, 31%). HPLC, Rt: 1.98 min. (purity 95.1%). LC/MS, M+(ESI): 306.1, M−(ESI): 304.1.

Example 3

N-[5-(3-furyl)[1,2,4]triazolo[1,5-a]pyridin-2-yl]-4-(trifluoromethyl)benzamide

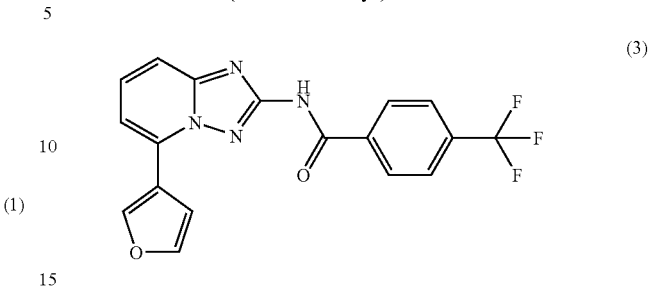

(3)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and 4-(trifluoromethyl)benzoyl chloride (125 mg, 0.60 mmol; 2.0 eq.) as a white powder (31.2 mg, 28%). HPLC, Rt: 4.02 min. (purity 99.4%). LC/MS, M+(ESI): 373.2, M−(ESI): 373.1.

Example 4 ethyl 3-{[5-(3-furyl)[1,2,4]triazolo[1,5-a]pyridin-2-yl]amino}-3-oxopropanoate

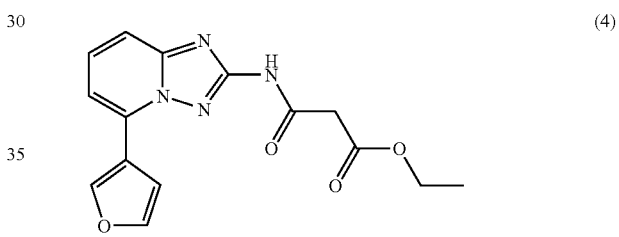

(4)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and ethyl 3-chloro-3-oxopropionate (90 mg, 0.60 mmol; 2.0 eq.) as a white powder (42 mg, 45%). HPLC, Rt: 2.72 min. (purity 90.8%). LC/MS, M+(ESI): 315.3, M−(ESI): 313.3.

Example 5

N-[5-(3-furyl)[1,2,4]triazolo[1,5-a]pyridin-2-yl]-2-methoxyacetamide

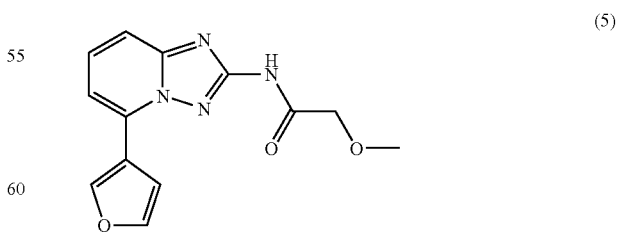

(5)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and methoxyacetyl chloride (65 mg, 0.60 mmol; 2.0 eq.) as a white powder (59 mg, 72%). HPLC, Rt: 2.21 min. (purity 98.2%). LC/MS, M⁺(ESI): 273.4, M⁻(ESI): 271.4.

Example 6

6-chloro-N-[5-(3-furyl)[1,2,4]triazolo[1,5-a]pyridin-2-yl]nicotinamide

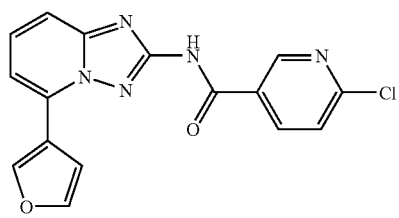

(6)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and 6-chloronicotinoyl chloride (65 mg, 0.60 mmol; 2.0 eq.) as a white powder (47.7 mg, 47%). HPLC, Rt: 3.00 min. (purity 98.6%). LC/MS, M⁺(ESI): 340.2, M⁻(ESI): 338.2.

Example 7 methyl 4-{[5-(3-furyl)[1,2,4]triazolo[1,5-a]pyridin-2-yl]amino}-4-oxobutanoate

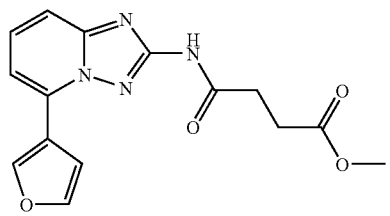

(7)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and 3-carbomethoxypropionyl chloride (65 mg, 0.60 mmol; 2.0 eq.) as a white powder (83.5 mg, 88%). HPLC, Rt: 2.40 min. (purity 95.4%). LC/MS, M⁻(ESI): 313.2.

Example 8

2-(benzyloxy)-N-[5-(3-furyl)[1,2,4]triazolo[1,5-a]pyridin-2-yl]acetamide

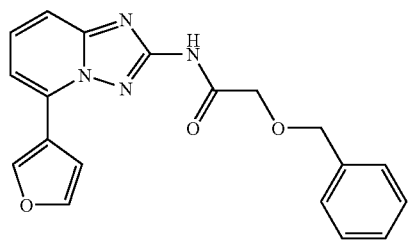

(8)

The title compound was prepared following procedure described for intermediate B1, but starting from 5-(3-furyl)[1,2,4]triazolo[1,5-a]pyridin-2-amine ((A2), 660 mg; 0.30 mmol; 1.0 eq.) and phenoxyacetyl chloride (65 mg, 0.60 mmol; 2.0 eq.) as a white powder (61.3 mg, 58%). HPLC, Rt: 3.59 min. (purity 96.1%). LC/MS, M⁺(ESI): 349.3, M⁻(ESI): 347.3.

Example 9

3-methoxy-N-[5-(1H-pyrrol-2-yl)[1,2,4]triazolo[1,5-a]pyridin-2-yl]-benzamide

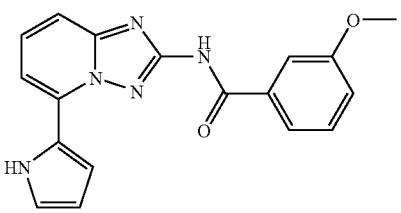

(9)

The title compound was prepared following procedure described for intermediate B1, but starting from tert-butyl 2-(2-amino[1,2,4]triazolo[1,5-a]pyridin-5-yl)-1H-pyrrole-1-carboxylate ((A6), 50 mg; 0.17 mmol; 1.0 eq.) and m-anisoyl chloride (57 mg; 0.33 mmol; 2.0 eq.). Further treatment with a DCM/TFA solution (2:1) and purification by flash chromatography on silica (EtOAc/c-Hex, gradient from 50:60 to 80:20) gave the title compound as a white solid (23.1 mg, 41%). HPLC, Rt: 3.40 min. (purity 94.7%). LC/MS, M⁺(ESI): 334.3, M⁺(ESI): 332.1

Example 10

N-[5-(1H-pyrrol-2-yl)[1,2,4]triazolo[1,5-a]pyridin-2-yl]cyclopentanecarboxamide

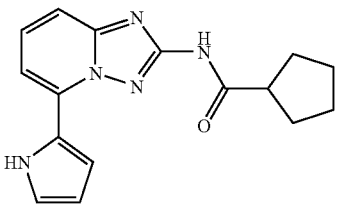

(10)

The title compound was prepared following procedure and work up described for example 9, but starting from tert-butyl 2-(2-amino[1,2,4]triazolo[1,5-a]pyridin-5-yl)-1H-pyrrole-1-carboxylate ((A6), 50 mg; 0.17 mmol; 1.0 eq.) and cyclopentanecarbonyl chloride (44 mg; 0.33 mmol; 2.0 eq.) as a white solid (25.4 mg, 51%). HPLC, Rt: 3.17 min. (purity 99.7%). LC/MS, M⁺(ESI): 296.4, M⁻(ESI): 294.3.

Example 11

N-[5-(1H-pyrrol-2-yl)[1,2,4]triazolo[1,5-a]pyridin-2-yl]benzamide

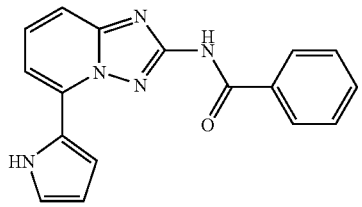

(11)

The title compound was prepared following procedure and work up described for example 9, but starting from tert-butyl 2-(2-amino[1,2,4]triazolo[1,5-a]pyridin-5-yl)-1H-pyrrole-1-carboxylate ((A6), 50 mg; 0.17 mmol; 1.0 eq.) and benzoyl chloride (47 mg; 0.33 mmol; 2.0 eq.) as a white solid (22.7 mg, 45%). HPLC, Rt: 3.23 min. (purity 91.6%). LC/MS, M+(ESI): 304.3, M−(ESI): 302.3.

Example 12

N-[5-(1H-pyrazol-4-yl)[1,2,4]triazolo[1,5-a]pyridin-2-yl]benzamide

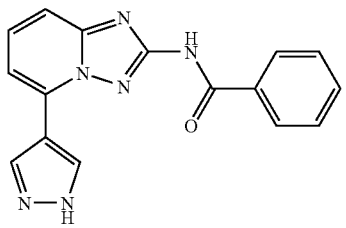

(12)

The title compound was prepared following procedure described for intermediate A1 step a), but starting from N-(5-bromo[1,2,4]triazolo[1,5-a]pyridin-2-yl)benzamide ((B1), 75 mg; 0.24 mmol; 1.0 eq.) and 4-(4,4,5,5-tetramethyl-1,3,2-dioxaborolan-2-yl)-pyrazole-1-carboxylic acid tert-butyl ester (139 mg; 0.47 mmol; 2.0 eq.), at 140° C. for 14 h. Further treatment with a 1 N methanolic HCl solution (0.5 mL) and purification by flash chromatography on silica (EtOAc/c-Hex, 80:20) gave the title compound as a white powder (23 mg, 32%). HPLC, Rt: 2.07 min. (purity 96.9%). LC/MS, M+(ESI): 305.3, M−(ESI): 303.3.

Example 13

N-[5-(1H-pyrrol-2-yl)[1,2,4]triazolo[1,5-a]pyridin-2-yl]nicotinamide

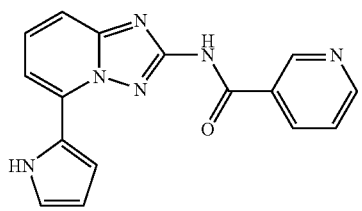

(13)

The title compound was prepared following procedure described for example 9, but starting from tert-butyl 2-(2-amino[1,2,4]triazolo[1,5-a]pyridin-5-yl)-1H-pyrrole-1-carboxylate ((A6), 360 mg; 1.20 mmol; 1.0 eq.) and nicotinoyl chloride hydrochloride (428 mg; 2.41 mmol; 2.0 eq.) as a brown powder (245 mg, 67%). HPLC, Rt: 2.14 min. (purity 100.0%). LC/MS, M−(ESI): 303.3.

Example 14

N-[5-(2-furyl)[1,2,4]triazolo[1,5-a]pyridin-2-yl]benzamide

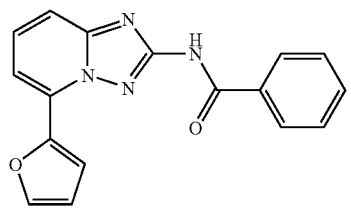

(14)

The title compound was prepared following procedure described for intermediate A1 step a), but starting from N-(5-bromo[1,2,4]triazolo[1,5-a]pyridin-2-yl)benzamide ((B1), 75 mg; 0.24 mmol; 1.0 eq.) and 2-furanboronic acid (53 mg; 0.47 mmol; 2.0 eq.). Purification by flash chromatography on silica (EtOAc/c-Hex, 45:55) gave the title compound as an off-white powder (19 mg, 26%). HPLC, Rt: 3.24 min. (purity 97.9%). LC/MS, M+(ESI): 305.3, M−(ESI): 303.2.

Example 15

N-[6-(3-fluorophenyl)[1,2,4]triazolo[1,5-a]pyridin-2-yl]nicotinamide

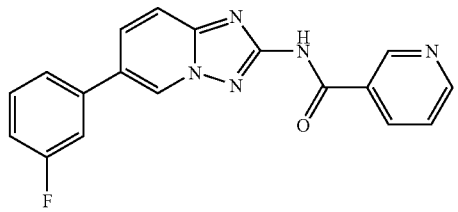

(15)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and 3-fluorophenylboronic acid (66 mg; 0.47 mmol; 2.0 eq.). Purification by flash chromatography on silica (MeOH/EtOAc, 5:95) gave the title compound as a beige powder (42 mg, 53%). HPLC, Rt: 2.40 min. (purity 99.7%). LC/MS, M+(ESI): 334.3, M−(ESI): 332.3.

Example 16

N-(6-phenyl[1,2,4]triazolo[1,5-a]pyridin-2-yl)nicotinamide

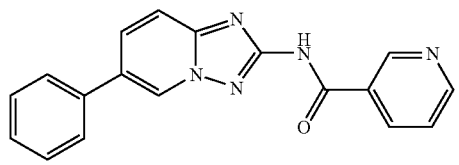
(16)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and phenylboronic acid (57 mg; 0.47 mmol; 2.0 eq.). Purification by flash chromatography on silica (MeOH/EtOAc, 5:95) gave the title compound as a beige powder (42 mg, 56%). HPLC, Rt: 2.26 min. (purity 98.7%).

Example 17

N-[6-(3-furyl)[1,2,4]triazolo[1,5-a]pyridin-2-yl]nicotinamide

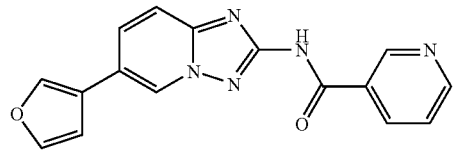
(17)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and furan-3-boronic acid (57 mg; 0.47 mmol; 2.0 eq.). Purification by flash chromatography on silica (MeOH/EtOAc, 5:95) gave the title compound as a beige powder (15.6 mg, 21%). HPLC, Rt: 1.82 min. (purity 92.2%). LC/MS, M$^+$(ESI): 306.3, M$^-$(ESI): 304.3.

Example 18

N-[6-(3-thienyl)[1,2,4]triazolo[1,5-a]pyridin-2-yl]nicotinamide

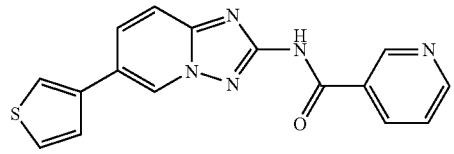
(18)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and 3-thienylboronic acid (60 mg; 0.47 mmol; 2.0 eq.). Purification by flash chromatography on silica (MeOH/EtOAc, 5:95) gave the title compound as a beige powder (18.1 mg, 23%). HPLC, Rt: 2.13 min. (purity 94.3%). LC/MS, M$^+$(ESI): 322.3, M$^-$(ESI): 320.2.

Example 19

N-[5-(3-furyl)[1,2,4]triazolo[1,5-a]pyridin-2-yl]-3-methoxybenzamide

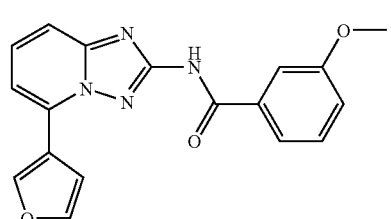
(19)

The title compound was prepared following procedure described for intermediate B1, but starting from 5-(3-furyl)[1,2,4]triazolo[1,5-a]pyridin-2-amine ((A2), 50 mg; 0.25 mmol; 1.0 eq.) and m-anisoyl chloride (85 mg; 0.50 mmol; 2.0 eq.). Crude was purified on SPE NH$_2$ column and the title compound was isolated as a white powder (26.9 mg, 32%). HPLC, Rt: 3.32 min. (purity 89.0%). LC/MS, M$^+$(ESI): 306.4.

Example 20

N-[5-(3-furyl)[1,2,4]triazolo[1,5-a]pyridin-2-yl]-2-(2-thienyl)acetamide

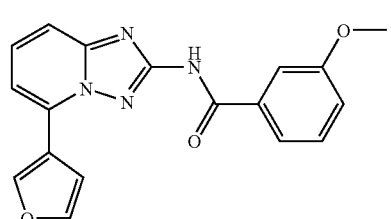
(20)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 2-thiopheneacetyl chloride (80 mg; 0.50 mmol; 2.0 eq.) as a white powder (30.9 mg, 38%). HPLC, Rt: 3.28 min. (purity 96.6%). LC/MS, M$^+$(ESI): 357.2, M$^-$(ESI): 355.2.

Example 21

N-[5-(3-furyl)[1,2,4]triazolo[1,5-a]pyridin-2-yl]cyclopentanecarboxamide

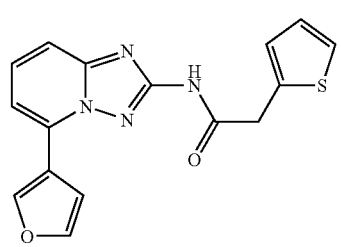
(21)

The title compound was prepared following procedure and work up described for example 19, but starting from 5-(3- furyl)[1,2,4]triazolo[1,5-a]pyridin-2-amine ((A2), 50 mg; 0.25 mmol; 1.0 eq.) and cyclopentanecarbonyl chloride (66 mg; 0.50 mmol; 2.0 eq.) as a white powder (64.1 mg, 86%). HPLC, Rt: 3.11 min. (purity 82.7%). LC/MS, M⁺(ESI): 297.4, M⁻(ESI): 295.3.

Example 22

N-[5-(3-furyl)[1,2,4]triazolo[1,5-a]pyridin-2-yl]-4-methoxybenzamide

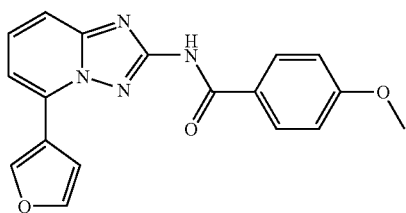

(22)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and p-anisoyl chloride (66 mg; 0.50 mmol; 2.0 eq.) as a white powder (58.2 mg, 69%). HPLC, Rt: 3.19 min. (purity 97.0%).

Example 23

N-[5-(3-furyl)[1,2,4]triazolo[1,5-a]pyridin-2-yl]isonicotinamide

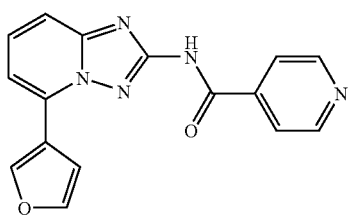

(23)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and isonicotinoyl chloride hydrochloride (89 mg; 0.50 mmol; 2.0 eq.) as a white powder (39.4 mg, 51%). HPLC, Rt: 1.90 min. (purity 97.2%). LC/MS, M⁺(ESI): 306.4, M⁻(ESI): 304.4.

Example 24

N-[5-(3-furyl)[1,2,4]triazolo[1,5-a]pyridin-2-yl]quinoxaline-6-carboxamide

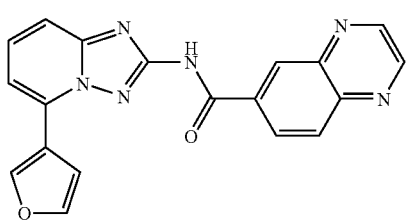

(24)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 6-quinoxalinecarbonyl chloride (96 mg; 0.50 mmol; 2.0 eq.) as a white powder (47.5 mg, 53%). HPLC, Rt: 2.73 min. (purity 62.3%). LC/MS, M⁺(ESI): 357.4, M⁻(ESI): 355.3.

Example 25

N-[6-(3-methoxyphenyl)[1,2,4]triazolo[1,5-a]pyridin-2-yl]nicotinamide

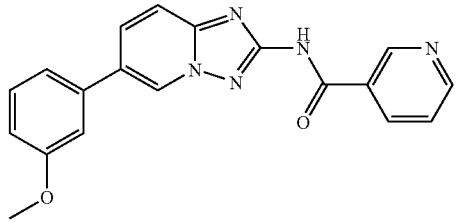

(25)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and 3-methoxybenzeneboronic acid (71 mg; 0.47 mmol; 2.0 eq.). Purification by flash chromatography on silica (MeOH/DCM, gradient from 0:100 to 10:90) gave the title compound as a beige powder (43 mg, 53%). HPLC, Rt: 2.41 min. (purity 99.2%). LC/MS, M⁺(ESI): 346.4, M⁻(ESI): 344.4.

Example 26

N-[6-(3-aminophenyl)[1,2,4]triazolo[1,5-a]pyridin-2-yl]nicotinamide

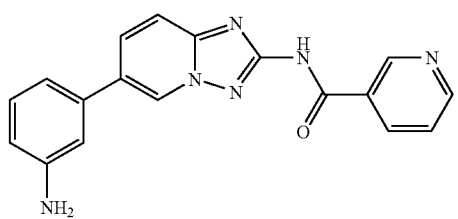

(26)

The title compound was prepared following procedure described for intermediate A1 step a) but starting from N-(6-bromo[1,2,4]triazolo[1,5-a]pyridin-2-yl)nicotinamide ((B6), 75 mg; 0.24 mmol; 1.0 eq.) and 3-aminobenzeneboronic acid (64 mg; 0.47 mmol; 2.0 eq.). Purification by flash chromatography on silica (MeOH/DCM, gradient from 0:100 to 10:90) gave the title compound as a dark red solid (31 mg, 40%). HPLC, Rt: 1.07 min. (purity 96.3%). LC/MS, M+(ESI): 331.4, M−(ESI): 329.4.

Example 27

N-[6-(3-cyanophenyl)[1,2,4]triazolo[1,5-a]pyridin-2-yl]nicotinamide

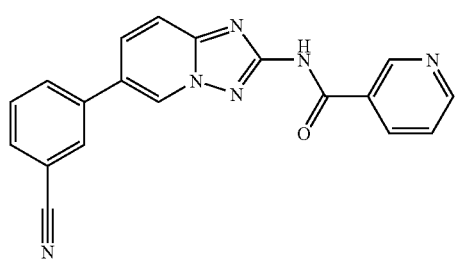

(27)

The title compound was prepared following procedure described for intermediate A1 step a), but starting from N-(6-bromo[1,2,4]triazolo[1,5-a]pyridin-2-yl)nicotinamide ((B6), 75 mg; 0.24 mmol; 1.0 eq.) and 3-cyanophenylboronic acid (69 mg; 0.47 mmol; 2.0 eq.). Purification by flash chromatography on silica (MeOH/DCM, gradient from 0:100 to 10:90) gave the title compound as a brown powder (6 mg, 7%). HPLC, Rt: 2.09 min. (purity 92.5%). LC/MS, M+(ESI): 341.4.

Example 28

N-[5-(3-furyl)[1,2,4]triazolo[1,5-a]pyridin-2-yl]isoxazole-5-carboxamide

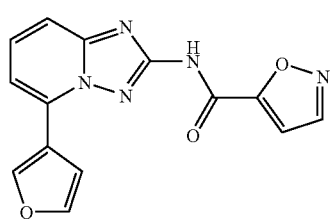

(28)

The title compound was prepared following procedure described for example 19, but starting from 5-(3-furyl)[1,2,4]triazolo[1,5-a]pyridin-2-amine ((A2), 50 mg; 0.25 mmol; 1.0 eq.) and isoxazole-5-carbonyl chloride (49 mg; 0.37 mmol; 1.5 eq.) as a white powder (19.4 mg, 26%). HPLC, Rt: 2.62 min. (purity 95.3%). LC/MS, M+(ESI): 296.4, M−(ESI): 294.3.

Example 29

N-[5-(3-furyl)[1,2,4]triazolo[1,5-a]pyridin-2-yl]-2,3-dihydro-1,4-benzodioxine-6-carboxamide

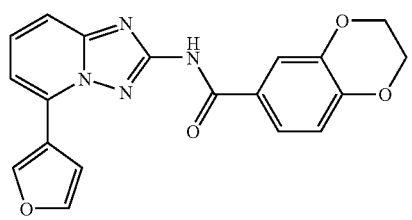

(29)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 2,3-dihydro-1,4-benzodioxine-6-carbonyl chloride (74 mg; 0.37 mmol; 1.5 eq.) as a white powder (34 mg, 37%). HPLC, Rt: 3.17 min. (purity 81.5%). LC/MS, M+(ESI): 363.0.

Example 30

N-[5-(cyclopropylamino)[1,2,4]triazolo[1,5-a]pyridin-2-yl]nicotinamide

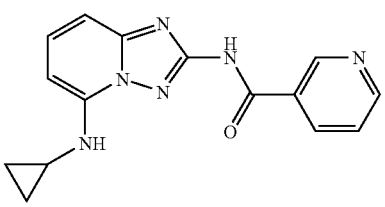

(30)

N-(5-bromo[1,2,4]triazolo[1,5-a]pyridin-2-yl)nicotinamide ((B2), 50 mg; 0.16 mmol; 1.0 eq.) in cyclopropylamine (1 mL) was heated at 80° C. overnight. The reaction mixture was diluted with H₂O and extracted with EtOAc. Combined organic phases were washed with brine, dried over magnesium sulfate, filtered and concentrated. The title compound was obtained by recrystallization in EtOAc/c-Hex as a white powder (16.60 mg; 35%). HPLC, Rt: 1.77 min. (purity 98.3%). LC/MS, M+(ESI): 295.4, M−(ESI): 293.4.

Example 31

N-(5-pyrrolidin-1-yl[1,2,4]triazolo[1,5-a]pyridin-2-yl)nicotinamide

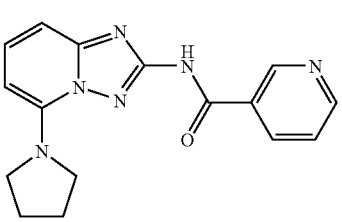

(31)

The title compound was prepared following procedure and work up described for example 30, but starting from N-(5-bromo[1,2,4]triazolo[1,5-a]pyridin-2-yl)nicotinamide ((B2), 50 mg; 0.16 mmol; 1.0 eq.) and pyrrolidine (1 mL) as a white solid (1 mg, 2%). HPLC, Rt: 1.81 min. (purity 97.3%). LC/MS, M+(ESI): 309.4, M−(ESI): 307.4.

Example 32

N-[5-(3-furyl)[1,2,4]triazolo[1,5-a]pyridin-2-yl]-3,5-dimethoxybenzamide

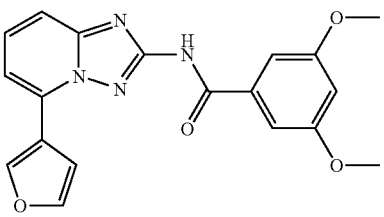

(32)

The title compound was prepared following procedure described for intermediate B1, but starting from 5-(3-furyl)[1,2,4]triazolo[1,5-a]pyridin-2-amine ((A2), 50 mg; 0.25 mmol; 1.0 eq.) and 3,5-dimethoxybenzoyl chloride (60 mg; 0.30 mmol; 1.2 eq.) as a white powder (42.9 mg; 47%). HPLC, Rt: 3.51 min. (purity 95.3%). LC/MS, M⁺(ESI): 365.3, M⁻(ESI): 363.3.

Example 33

N-[5-(3-furyl)[1,2,4]triazolo[1,5-a]pyridin-2-yl]biphenyl-4-carboxamide

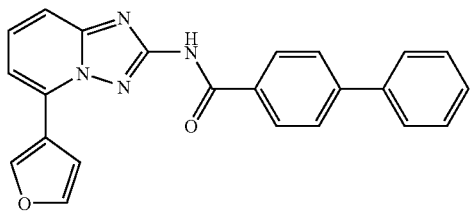

(33)

The title compound was prepared following procedure described for intermediate B1, but starting from 5-(3-furyl)[1,2,4]triazolo[1,5-a]pyridin-2-amine ((A2), 50 mg; 0.25 mmol; 1.0 eq.) and 4-biphenylcarbonyl chloride (87 mg; 0.37 mmol; 1.5 eq.) as a white powder (53.7 mg, 56%). HPLC, Rt: 4.25 min. (purity 95.2%). LC/MS, M⁺(ESI): 381.4, M⁻(ESI): 379.4.

Example 34

1-(4-chlorophenyl)-N-[5-(3-furyl)[1,2,4]triazolo[1,5-a]pyridin-2-yl]cyclopentanecarboxamide

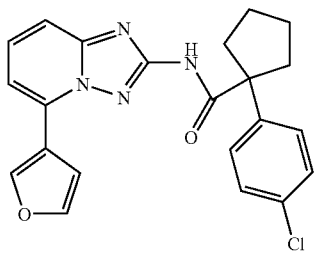

(34)

The title compound was prepared following procedure described for intermediate B1, but starting from 5-(3-furyl)[1,2,4]triazolo[1,5-a]pyridin-2-amine ((A2), 50 mg; 0.25 mmol; 1.0 eq.) and 1-(4-chlorophenyl)-1-cyclopentanecarbonyl chloride (Lancaster, 91 mg; 0.37 mmol; 1.5 eq.) as a white foam (61.1 mg, 60%). HPLC, Rt: 4.64 min. (purity 73.4%). LC/MS, M⁺(ESI): 407.4, M⁻(ESI): 405.4.

Example 35

N-[5-(3-furyl)[1,2,4]triazolo[1,5-a]pyridin-2-yl]-2,3-dihydro-1-benzofuran-5-carboxamide

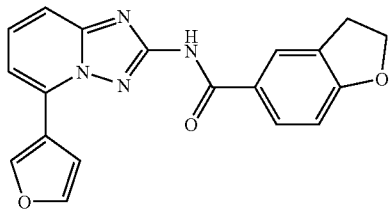

(35)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 2,3-dihydro-1-benzofuran-5-carbonyl chloride (68 mg; 0.37 mmol; 1.5 eq.) as a white solid (25.7 mg, 29%). HPLC, Rt: 3.14 min. (purity 78.8%). LC/MS, M⁺(ESI): 347.4, M⁻(ESI): 345.3.

Example 36

N-[5-(3-furyl)[1,2,4]triazolo[1,5-a]pyridin-2-yl]-3-furamide

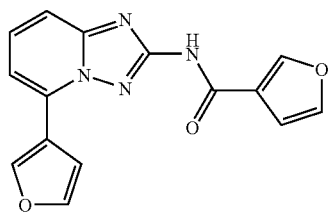

(36)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 3-furoyl chloride (39 mg; 0.3 mmol; 1.2 eq.) as a white powder (45.3 mg, 61%). HPLC, Rt: 2.65 min. (purity 97.5%). LC/MS, M⁺(ESI): 295.4, M⁻(ESI): 293.4.

Example 37

1-acetyl-N-[5-(3-furyl)[1,2,4]triazolo[1,5-a]pyridin-2-yl]piperidine-4-carboxamide

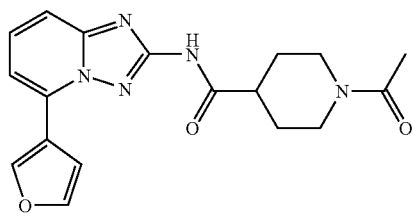

(37)

The title compound was prepared following procedure and work up described for example 19, but starting from 5-(3-furyl)[1,2,4]triazolo[1,5-a]pyridin-2-amine ((A2), 50 mg; 0.25 mmol; 1.0 eq.) and 1-acetylpiperidine-4-carbonyl chloride (57 mg; 0.3 mmol; 1.2 eq.) as a white powder (41.3 mg, 46%). HPLC, Rt: 2.15 min. (purity 93.3%). LC/MS, M⁺(ESI): 354.4, M⁻(ESI): 352.4.

Example 38

2,2-difluoro-N-[5-(3-furyl)[1,2,4]triazolo[1,5-a]pyridin-2-yl]-1,3-benzodioxole-4-carboxamide

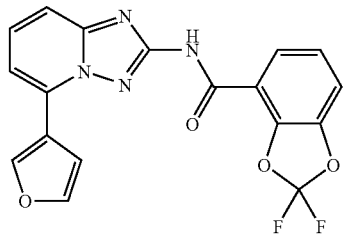

(38)

The title compound was prepared following procedure and work up described for example 19, but starting from 5-(3- furyl)[1,2,4]triazolo[1,5-a]pyridin-2-amine ((A2), 50 mg; 0.25 mmol; 1.0 eq.) and 2,2-difluoro-1,3-benzodioxole-4-carbonyl chloride (Alpha, 66 mg; 0.3 mmol; 1.2 eq.) as a white powder (75.2 mg, 78%). HPLC, Rt: 4.01 min. (purity 97.4%). LC/MS, M⁺(ESI): 385.3, M⁻(ESI): 383.3.

Example 39

N-[5-(3-thienyl)[1,2,4]triazolo[1,5-a]pyridin-2-yl]nicotinamide

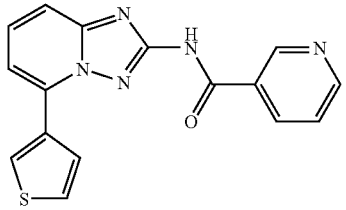

(39)

The title compound was prepared following procedure described for example 2, but starting from 5-(3-thienyl)[1,2,4]triazolo[1,5-a]pyridin-2-amine ((A1), 82 mg; 0.38 mmol; 1.5 eq.) and nicotinoyl chloride hydrochloride (55 mg; 0.3 mmol; 1.2 eq.) as a beige solid (21 mg, 26%). HPLC, Rt: 2.15 min. (purity 97.3%). LC/MS, M⁺(ESI): 322.0, M⁻(ESI): 320.0.

Example 40

N-[1,2,4]triazolo[1,5-a]quinolin-2-ylnicotinamide

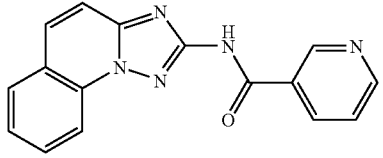

(40)

The title compound was prepared following procedure described for example 2, but starting from [1,2,4]triazolo[1,5-a]quinolin-2-amine ((A13), 67 mg; 0.37 mmol; 1.5 eq.) and nicotinoyl chloride hydrochloride (80 mg; 0.44 mmol; 1.2 eq.). Purification by flash chromatography on silica (DCM/MeOH, gradient from 98:2 to 95:5) gave the title compound as an orange oil (27 mg, 38%). HPLC, Rt: 1.83 min. (purity 97.9%). LC/MS, M⁺(ESI): 290.0, M⁻(ESI): 288.0.

Example 41

N-[5-(cyclopentylamino)[1,2,4]triazolo[1,5-a]pyridin-2-yl]benzamide

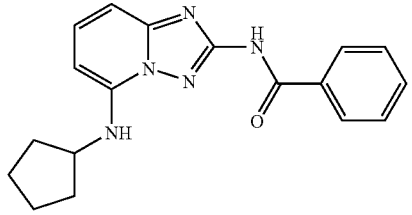

(41)

The title compound was prepared following procedure described for example 30, but starting from N-(5-chloro[1,2,4]triazolo[1,5-a]pyridin-2-yl)benzamide ((B3), 44 mg; 0.16 mmol; 1.0 eq.) and cyclopentylamine (1.0 mL) as a white powder (23 mg, 44%). HPLC, Rt: 3.06 min. (purity 99.5%). LC/MS, M⁺(ESI): 322.1, M⁻(ESI): 320.1.

Example 42

N-[5-(3-furyl)[1,2,4]triazolo[1,5-a]pyridin-2-yl]nicotinamide 1-oxide

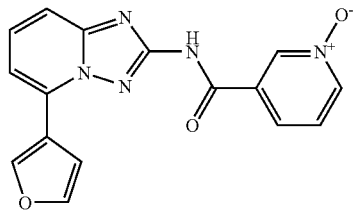

(42)

The title compound was prepared following procedure described for example 2, but starting from 5-(3-furyl)[1,2,4]triazolo[1,5-a]pyridin-2-amine ((A2), 100 mg; 0.50 mmol; 1.0 eq.) and nicotinic acid N-oxide (83 mg, 0.6 mmol, 1.2 eq.) as a light yellow solid (37.2 mg, 23%). HPLC, Rt: 1.98 min. (purity 98.8%). LC/MS, M⁺(ESI): 322.1, M⁻(ESI): 320.1.

Example 43

N-{5-[(3-methoxypropyl)amino][1,2,4]triazolo[1,5-a]pyridin-2-yl}benzamide

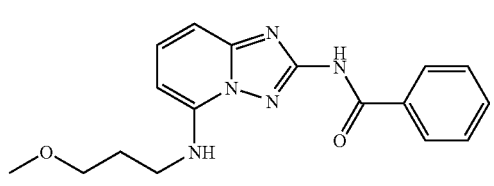

(43)

The title compound was prepared following procedure described for example 30 but starting from N-(5-chloro[1,2,4]triazolo[1,5-a]pyridin-2-yl)benzamide ((B3), 50 mg; 0.18 mmol; 1.0 eq.) and 3-methoxypropylamine (195 µl; 1.91 mmol; 10.0 eq.) in THF (3.0 mL), 90° C., 12 h, as white needles (35 mg; 56%). HPLC, Rt: 1.95 min. (purity 99.3%). LC/MS, M⁺(ESI): 326.2.

Example 44

N-{5-[(2-furylmethyl)amino][1,2,4]triazolo[1,5-a]pyridin-2-yl}benzamide

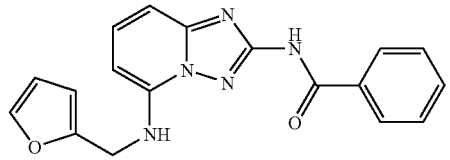

(44)

The title compound was prepared following procedure described for example 30 but starting from N-(5-chloro[1,2,4]triazolo[1,5-a]pyridin-2-yl)benzamide ((B3), 50 mg; 0.18 mmol; 1.0 eq.) and furfurylamine (1.0 mL) as a beige powder (31 mg, 51%). HPLC, Rt: 2.20 min. (purity 94.1%). LC/MS, M+(ESI): 334.1, M−(ESI): 332.1.

Example 45

N-{5-[(tetrahydrofuran-2-ylmethyl)amino][1,2,4]triazolo[1,5-a]pyridin-2-yl}benzamide

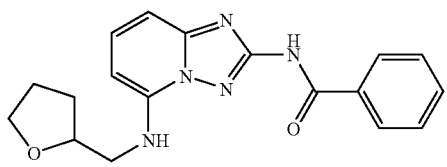

(45)

The title compound was prepared following procedure described for example 30 but starting from N-(5-chloro[1,2,4]triazolo[1,5-a]pyridin-2-yl)benzamide ((B3), 50 mg; 0.18 mmol; 1.0 eq.) and tetrahydrofurfurylamine (1.0 mL) as a white powder (32 mg, 52%). HPLC, Rt: 2.34 min. (purity 91.7%). LC/MS, M+(ESI): 339.0, M−(ESI): 338.1.

Example 46

3-(acetylamino)-N-[5-(3-furyl)[1,2,4]triazolo[1,5-a]pyridin-2-yl]benzamide

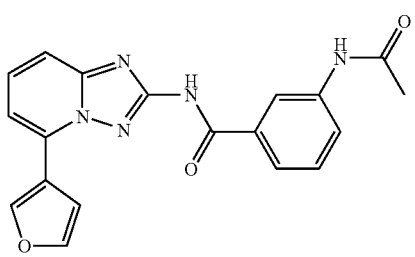

(46)

The title compound was prepared following procedure described for example 2, but starting from 5-(3-furyl)[1,2,4]triazolo[1,5-a]pyridin-2-amine ((A2), 100 mg; 0.50 mmol; 1.0 eq.) and isophthalamic acid (49 mg, 0.3 mmol, 1.2 eq.) as a beige powder (20 mg, 23%). HPLC, Rt: 2.64 min. (purity 90.7%). LC/MS, M+(ESI): 362.1, M−(ESI): 360.1.

Example 47

N-[5-(cyclohexylamino)[1,2,4]triazolo[1,5-a]pyridin-2-yl]benzamide

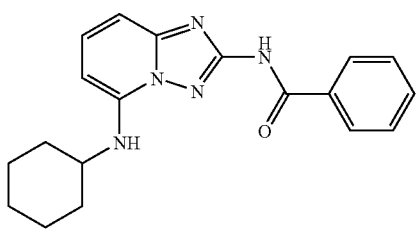

(47)

The title compound was prepared following procedure described for example 30 but starting from N-(5 chloro[1,2,4]triazolo[1,5-a]pyridin-2-yl)benzamide ((B3), 50 mg; 0.18 mmol; 1.0 eq.) and cyclohexylamine (1.0 mL) as an off-white powder (50 mg, 81%). HPLC, Rt: 3.33 min. (purity 94.3%). LC/MS, M+(ESI): 336.2, M−(ESI): 334.1.

Example 48

N-[5-(3-furyl)[1,2,4]triazolo[1,5-a]pyridin-2-yl]-3-(methylsulfonyl)benzamide

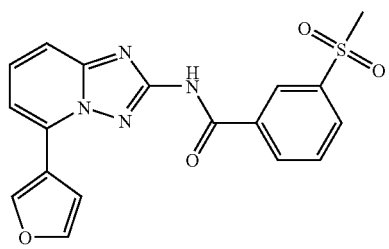

(48)

The title compound was prepared following procedure described for example 2, but starting from 5-(3-furyl)[1,2,4]triazolo[1,5-a]pyridin-2-amine ((A2), 50 mg; 0.25 mmol; 1.0 eq.) and 3-methylsulphonylbenzoic acid (60 mg, 0.3 mmol, 1.2 eq.) as an off-white solid (9 mg, 9%). HPLC, Rt: 2.79 min. (purity 96.5%). LC/MS, M+(ESI): 383.0, M−(ESI): 381.0.

Example 49

3-(aminomethyl)-N-[5-(3-furyl)[1,2,4]triazolo[1,5-a]pyridin-2-yl]benzamide

Step a) Formation of tert-butyl[3-({[5-(3-furyl)[1,2,4]triazolo[1,5-a]pyridin-2-yl]amino}carbonyl)benzyl]carbamate

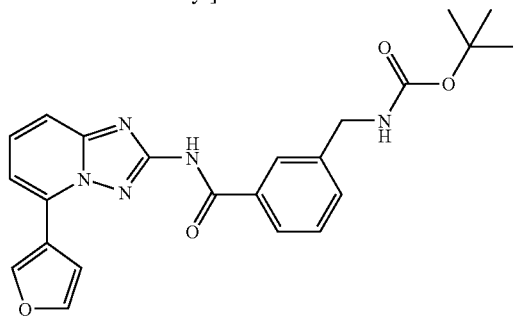

The title compound was prepared following procedure and work up described for example 2, but starting from 5-(3-furyl)[1,2,4]triazolo[1,5-a]pyridin-2-amine ((A2), 50 mg; 0.25 mmol; 1.0 eq.) and boc-(3-aminomethyl)-benzoic acid (75 mg; 0.3 mmol; 1.2 eq.) as a white solid 20.0 mg, 18%). HPLC, Rt: 3.86 min. (purity 75.6%). LC/MS, M+(ESI): 434.1, M−(ESI): 432.2.

Step b) Preparation of 3-(aminomethyl)-N-[5-(3-furyl)[1,2,4]triazolo[1,5-a]pyridin-2-yl]benzamide

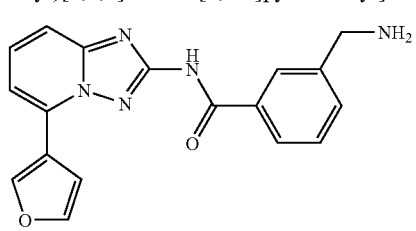

(49)

Tert-butyl[4-({[5-(3-furyl)[1,2,4]triazolo[1,5-a]pyridin-2-yl]amino}carbonyl)benzyl]carbamate (20 mg, 0.05 mmol, 1.0 eq.) was suspended in DCM/TFA (50:1, 1 mL) and reaction mixture was stirred at rt for 1 h. The reaction mixture was then concentrated under vacuum, the residue slurried with diethyl ether and filtered to give the title compound as a white solid (11 mg, 54%). HPLC, Rt: 3.57 min. (purity 96.3%). LC/MS, M+(ESI): 334.1.

Example 50

N-(5-{[1-(hydroxymethyl)propyl]amino}[1,2,4]triazolo[1,5-a]pyridin-2-yl)benzamide

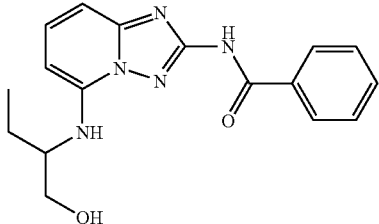
(50)

The title compound was prepared following procedure described for example 30, but starting from N-(5-chloro[1,2,4]triazolo[1,5-a]pyridin-2-yl)benzamide ((B3), 52 mg; 0.19 mmol; 1.0 eq.) and 2-amino-1-butanol (0.2 mL) as a white powder (13 mg, 22%). HPLC, Rt: 2.25 min. (purity 90.7%). LC/MS, M+(ESI): 326.2.

Example 51

N-[6-(3-hydroxyphenyl)[1,2,4]triazolo[1,5-a]pyridin-2-yl]benzamide

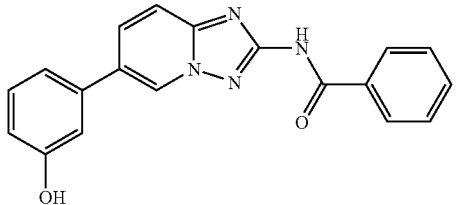
(51)

The title compound was prepared following procedure described for intermediate A1, step a), but starting from N-(6-bromo[1,2,4]triazolo[1,5-a]pyridin-2-yl)benzamide ((B5), 75 mg; 0.24 mmol; 1.0 eq.) and 3-hydroxyphenylboronic acid (65 mg; 0.47 mmol; 2.0 eq.). Purification by flash chromatography on silica (EtOAc/c-Hex, gradient from 50:50 to 100:0) gave the title compound as a brown solid (9.5 mg, 12%). HPLC, Rt: 2.59 min. (purity 91.6%). LC/MS, M+(ESI): 331.1, M−(ESI): 329.1.

Example 52 tert-butyl[4-({[5-(3-furyl)[1,2,4]triazolo[1,5-a]pyridin-2-yl]amino}carbonyl)benzyl]carbamate

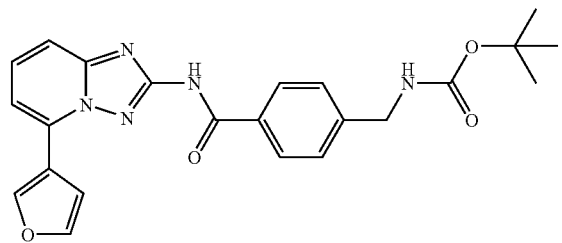
(52)

The title compound was prepared following procedure and work up described for example 2, but starting from 5-(3-furyl)[1,2,4]triazolo[1,5-a]pyridin-2-amine ((A2), 75 mg; 0.37 mmol; 1.0 eq.) and boc-(4-aminomethyl)-benzoic acid (113 mg; 0.45 mmol; 1.2 eq.) as a white foam (35.4 mg, 22%). HPLC, Rt: 3.69 min. (purity 88.9%). LC/MS, M+(ESI): 434.1, M−(ESI): 432.1.

Example 53

N-[5-(3-furyl)[1,2,4]triazolo[1,5-a]pyridin-2-yl]-4-isobutylbenzamide

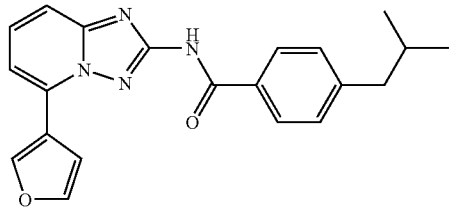
(53)

The title compound was prepared following procedure and work up described for example 2, but starting from 5-(3-furyl)[1,2,4]triazolo[1,5-a]pyridin-2-amine ((A2), 75 mg; 0.37 mmol; 1.0 eq.) and 4-isobutylbenzoic acid (80 mg; 0.45 mmol; 1.2 eq.) as a yellow foam (25.5 mg, 19%). HPLC, Rt: 4.39 min. (purity 93.6%). LC/MS, M+(ESI): 361.1, M−(ESI): 359.1.

Example 54 tert-butyl[4-({[5-(3-furyl)[1,2,4]triazolo[1,5-a]pyridin-2-yl]-amino}carbonyl)phenoxy]acetate

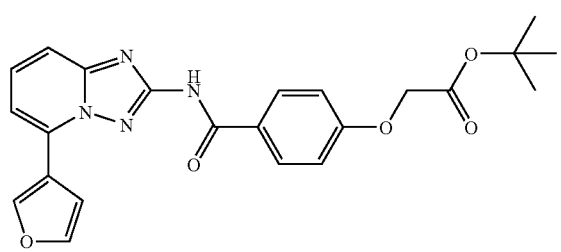
(54)

The title compound was prepared following procedure and work up described for example 2, but starting from 5-(3-furyl)[1,2,4]triazolo[1,5-a]pyridin-2-amine ((A2), 75 mg; 0.37 mmol; 1.0 eq.) and 4-(2-t-butoxy-2-oxoethoxy)benzoic acid (113 mg; 0.45 mmol; 1.2 eq.) as a white foam (21.6 mg, 13%). HPLC, Rt: 3.98 min. (purity 98.3%). LC/MS, M+(ESI): 435.1, M−(ESI): 433.1.

Example 55

4-butyl-N-[5-(3-furyl)[1,2,4]triazolo[1,5-a]pyridin-2-yl]benzamide

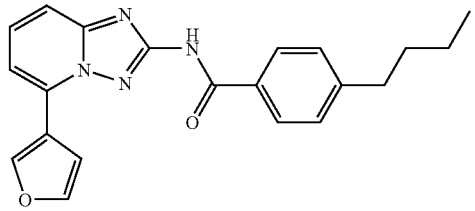
(55)

The title compound was prepared following procedure and work up described for example 2, but starting from 5-(3-furyl)

[1,2,4]triazolo[1,5-a]pyridin-2-amine ((A2), 75 mg; 0.37 mmol; 1.0 eq.) and 4-butylbenzoic acid (80 mg; 0.45 mmol; 1.2 eq.) as a yellow foam (20 mg, 15%). HPLC, Rt: 4.45 min. (purity 82.6%). LC/MS, M+(ESI): 361.1, M−(ESI): 359.1.

Example 56

N-[6-(4-hydroxy-3-methoxyphenyl)[1,2,4]triazolo[1,5-a]pyridin-2-yl]benzamide hydrochloride (56)

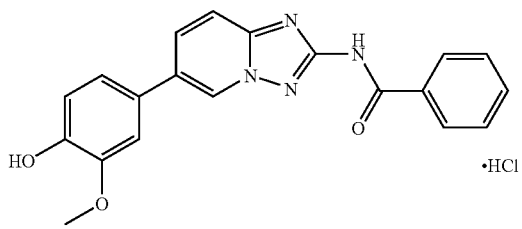

To N-(6-bromo[1,2,4]triazolo[1,5-a]pyridin-2-yl)benzamide ((B5), 400 mg; 1.26 mmol; 1.0 eq.), cesium fluoride (383 mg; 2.52 mmol; 2.0 eq.) dichlorobis(triphenylphosphine)palladium (89 mg; 0.13 mmol; 0.10 eq.) and 2-methoxy-4-(4,4,5,5-tetramethyl-1,3,2-dioxaborolan-2-yl)phenol (631 mg; 2.52 mmol; 2.0 eq.) in a sealed tube, under inert atmosphere, were added dioxane (3.2 mL) and water (1.6 mL). The mixture was heated at 120° C. for 12 hours. The reaction mixture was cooled down to rt and filtered over a celite pad. The celite was carefully rinsed with MeOH and a 0.1N solution of HCl was added to the filtrate. The desired product was precipitated by addition of EtOAc, filtered and dried under reduced pressure as a beige solid (373 mg, 74%). $^1$H NMR (DMSO-d$_6$) δ 11.27 (s, 1H), 9.24 (s, 1H), 8.03-8.01 (m, 3H), 7.76 (d, J=9 Hz, 1H), 7.65-7.51 (m, 3H), 7.37 (d, J=1.8 Hz, 1H), 7.22 (dd, J=1.8, 8.2 Hz, 1H), 6.89 (d, J=8.2 Hz, 1H), 4.7-3.9 (bs, 7H), 3.89 (s, 3H). HPLC, Rt: 2.59 min. (purity 96.4%). LC/MS, M+(ESI): 361.03, M−(ESI): 359.05. CHN analysis: [C$_{20}$H$_{16}$N$_4$O$_3$.1.0HCl.2.0H$_2$O] Corrected: C, 55.50%; H, 4.89%; N, 12.94%. Found: C, 55.83%; H 4.84%; N, 13.14%.

Example 57

N-{5-[(2-methoxyethyl)amino][1,2,4]triazolo[1,5-a]pyridin-2-yl}benzamide (57)

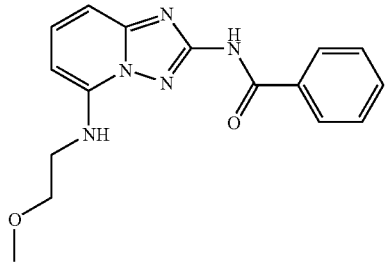

The title compound was prepared following procedure described for example 30 but starting from N-(5-chloro[1,2,4]triazolo[1,5-a]pyridin-2-yl)benzamide ((B3), 50 mg; 0.18 mmol; 1.0 eq.) and 2-methoxyethylamine (1.0 mL) as an off-white solid (52 mg, 91%). HPLC, Rt: 2.08 min. (purity 90.1%). LC/MS, M+(ESI): 312.1, M−(ESI): 310.1.

Example 58

N-{5-[(2,3-dihydroxypropyl)amino][1,2,4]triazolo[1,5-a]pyridin-2-yl}benzamide (58)

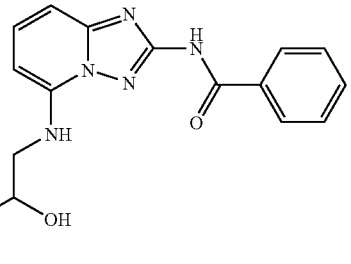

The title compound was prepared following procedure described for example 30 but starting from N-(5-chloro[1,2,4]triazolo[1,5-a]pyridin-2-yl)benzamide ((B3), 50 mg; 0.18 mmol; 1.0 eq.) and 3-amino-1,2-propanediol (1.0 mL) as a white powder (6 mg, 7%). HPLC, Rt: 1.65 min. (purity 99.5%). LC/MS, M+(ESI): 328.1, M−(ESI): 326.1.

Example 59

N-[6-(2,3-dihydro-1-benzofuran-5-yl)[1,2,4]triazolo[1,5-a]pyridin-2-yl]benzamide (59)

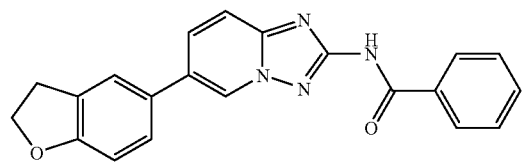

The title compound was prepared following procedure described for example 56 but starting from N-(6-bromo[1,2,4]triazolo[1,5-a]pyridin-2-yl)benzamide ((B5), 150 mg; 0.47 mmol; 1.0 eq.) and 2,3-dihydro-1-benzofuran-5-ylboronic acid (155 mg; 0.95 mmol; 2.0 eq.). Purification by flash chromatography on silica (EtOAc/c-Hex, gradient from 40:60 to 100:0) gave the title compound as a white solid (117.2 mg, 69%). HPLC, Rt: 3.18 min. (purity 84.6%). LC/MS, M+(ESI): 357.1, M−(ESI): 355.1.

Example 60

N-[5-(benzylamino)[1,2,4]triazolo[1,5-a]pyridin-2-yl]nicotinamide (60)

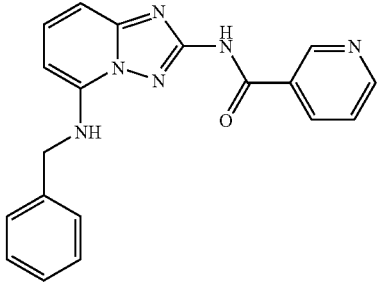

The title compound was prepared following procedure described for example 30 but starting from N-(5-bromo[1,2, 4]triazolo[1,5-a]pyridin-2-yl)nicotinamide ((B2), 100 mg; 0.31 mmol; 1.0 eq.) and benzylamine (1.0 mL) as an oily solid (10 mg, 9%). HPLC, Rt: 2.46 min. (purity 85.8%). LC/MS, M⁺(ESI): 345.1, M⁻(ESI): 343.1.

Example 61

N-[5-(cycloheptylamino)[1,2,4]triazolo[1,5-a]pyridin-2-yl]nicotinamide dihydrochloride (61)

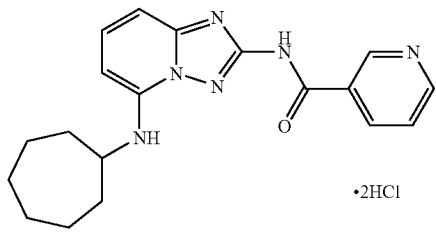

·2HCl

The title compound was prepared following procedure described for example 30 but starting from N-(5-chloro[1,2,4]triazolo[1,5-a]pyridin-2-yl)nicotinamide ((B4), 296 mg; 1.08 mmol; 1.0 eq.) and cycloheptylamine (1.0 mL). The parent compound was dissolved in MeOH and Et₂O/HCl was added. The precipitate obtained was filtered, washed with Et₂O and dried under reduced pressure at 40° C. to give the title compound as a white powder (178 mg, 42%). HPLC, Rt: 2.98 min. (purity 99.7%). LC/MS, M⁺(ESI): 351.4, M⁻(ESI): 349.4. CHN analysis: [$C_{19}H_{22}N_6O$.2.0 HCl.1.5H₂O] Corrected: C, 50.67%; H, 6.04%; N, 18.66%. Found: C, 50.69%; H, 5.97%; N, 18.61%.

Example 62

N-[5-(cyclohexylamino)[1,2,4]triazolo[1,5-a]pyridin-2-yl]nicotinamide (62)

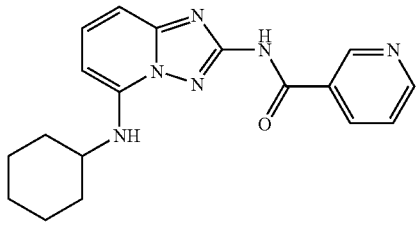

The title compound was prepared following procedure described for example 30 but starting from N-(5-bromo[1,2,4]triazolo[1,5-a]pyridin-2-yl)nicotinamide ((B2), 100 mg; 0.31 mmol; 1.0 eq.) and cyclohexylamine (1.0 mL) as a white powder (37 mg, 42%). HPLC, Rt: 2.60 min. (purity 99.6%). LC/MS, M⁺(ESI): 337.1, M⁻(ESI): 335.2.

Example 63

N-(5-{[(5-methyl-2-furyl)methyl]amino}[1,2,4]triazolo[1,5-a]pyridin-2-yl)nicotinamide (63)

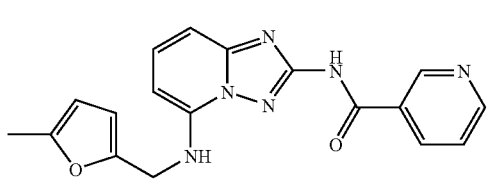

The title compound was prepared following procedure described for example 30 but starting from N-(5-bromo[1,2,4]triazolo[1,5-a]pyridin-2-yl)nicotinamide ((B2), 100 mg; 0.31 mmol; 1.0 eq.) and 5-methylfurfurylamine (1.0 mL) as an off-white solid (40 mg, 37%). HPLC, 2.38 min. Rt: (purity 98.6%). LC/MS, M⁻(ESI): 347.1.

Example 64

N-{5-[(tetrahydrofuran-2-ylmethyl)amino][1,2,4]triazolo[1,5-a]pyridin-2-yl}nicotinamide (64)

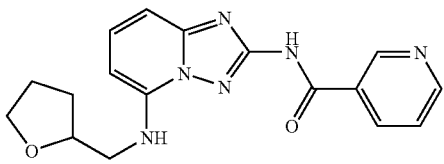

The title compound was prepared following procedure described for example 30 but starting from N-(5-bromo[1,2,4]triazolo[1,5-a]pyridin-2-yl)nicotinamide ((B2), 100 mg; 0.31 mmol; 1.0 eq.) and tetrahydrofurfurylamine (1.0 mL) as a white powder (17 mg, 16%). HPLC, Rt: 1.73 min. (purity 95.5%). LC/MS, M⁺(ESI): 339.1, M⁻(ESI): 337.1.

Example 65

N-[6-(4-hydroxyphenyl)[1,2,4]triazolo[1,5-a]pyridin-2-yl]benzamide (65)

The title compound was prepared following procedure described for example 56 but starting from N-(6-bromo[1,2,4]triazolo[1,5-a]pyridin-2-yl)benzamide ((B5), 150 mg; 0.47 mmol; 1.0 eq.) and 4-hydroxyphenylboronic acid (131 mg; 0.95 mmol; 2.0 eq.) as a white solid (15 mg, 9%). HPLC, Rt: 2.60 min. (purity 97.2%). LC/MS, M⁺(ESI): 331.1, M⁻(ESI): 329.1.

Example 66

N-[6-(4-hydroxy-3-methoxyphenyl)[1,2,4]triazolo[1,5-a]pyridin-2-yl]nicotinamide hydrochloride (66)

·HCl

The title compound was prepared following procedure described for example 56 but starting from N-(6-bromo[1,2,4]triazolo[1,5-a]pyridin-2-yl)nicotinamide ((B6), 400 mg; 1.26 mmol; 1.0 eq.) and 2-methoxy-4-(4,4,5,5-tetramethyl-1,3,2-dioxaborolan-2-yl)phenol (629 mg; 2.51 mmol; 2.0 eq.) as a light yellow solid (249 mg, 55%). HPLC, Rt: 1.71 min. (purity 60.7%). LC/MS, M⁺(ESI): 362.0, M⁻(ESI): 360.0. CHN analysis: [$C_{19}H_{15}N_5O_3$.1 HCl.0.4 $CH_3CN$.0.6$H_2O$] Corrected: C, 55.95%; H, 4.36%; N, 17.79%. Found: C, 55.95%; H, 4.76%; N, 17.53%.

Example 67

N-[5-(cyclooctylamino)[1,2,4]triazolo[1,5-a]pyridin-2-yl]nicotinamide

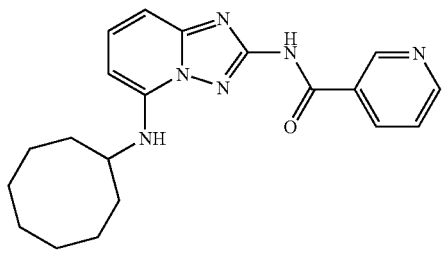

(67)

The title compound was prepared following procedure described for example 30 but starting from N-(5-chloro[1,2,4]triazolo[1,5-a]pyridin-2-yl)nicotinamide ((B4), 58 mg; 0.21 mmol; 1.0 eq.) and cyclooctylamine (440 µL) as a white powder (4 mg, 4%). HPLC, Rt: 3.25 min. (purity 97.9%). LC/MS, M⁺(ESI): 365.4, M⁻(ESI): 363.4.

Example 68

N-{5-[cyclohexyl(methyl)amino][1,2,4]triazolo[1,5-a]pyridin-2-yl}nicotinamide

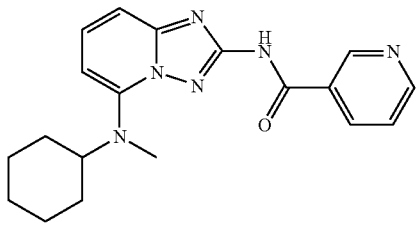

(68)

The title compound was prepared following procedure described for example 30 but starting from N-(5-chloro[1,2,4]triazolo[1,5-a]pyridin-2-yl)nicotinamide ((B4), 55 mg; 0.20 mmol; 1.0 eq.) and N-methylcyclohexylamine (1.0 mL) as an off white solid (30 mg, 43%). HPLC, Rt: 2.67 min. (purity 97.8%). LC/MS, M⁺(ESI): 351.4, M⁻(ESI): 349.4.

Example 69

N-[5-(tetrahydro-2H-pyran-4-ylamino)[1,2,4]triazolo[1,5-a]pyridin-2-yl]nicotinamide

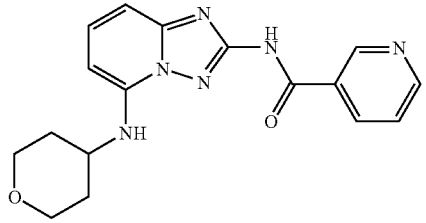

(69)

The title compound was prepared following procedure described for example 30 but starting from N-(5-bromo[1,2,4]triazolo[1,5-a]pyridin-2-yl)nicotinamide ((B2), 100 mg; 0.31 mmol; 1.0 eq.) and 4-aminotetrahydropyran (Apollo), 1.0 mL) as a white powder (15 mg, 14%). ¹H NMR (DMSO-d₆) δ 11.27 (s, 1H), 9.13 (d, J=1.9 Hz, 1H), 8.77 (d, J=4.9, 1.5 Hz, 1H), 8.33 (dd, J=8.0, 1.9 Hz, 1H), 7.58 (m, 1H), 7.51 (t, J=8.5 Hz, 1H), 6.90 (d, J=7.9 Hz, 1H), 6.62 (d, J=8.7 Hz, 1H), 6.38 (d, J=7.9 Hz, 1H), 3.88 (m, 2H), 3.80 (m, 1H), 3.45 (m, 2H), 1.89 (m, 2H), 1.72 (m, 2H). HPLC, Rt: 1.51 min. (purity 99.0%). LC/MS, M⁺(ESI): 339.4, M⁻(ESI): 337.4.

Example 70

N-{5-[(1-methylpiperidin-4-yl)amino][1,2,4]triazolo[1,5-a]pyridin-2-yl}nicotinamide

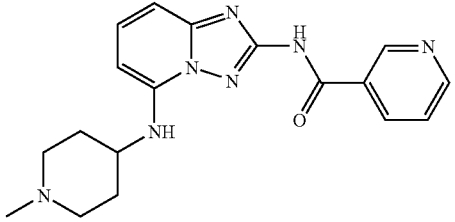

(70)

The title compound was prepared following procedure described for example 30 but starting from N-(5-bromo[1,2,4]triazolo[1,5-a]pyridin-2-yl)nicotinamide ((B2), 100 mg; 0.31 mmol; 1.0 eq.) and 4-amino-1-methyl-piperidine (1.0 mL) as a white powder (30 mg, 27%). ¹H NMR (DMSO-d₆) δ 11.25 (brs, 1H), 9.13 (d, J=1.9 Hz, 1H), 8.77 (dd, J=4.7, 1.7 Hz, 1H), 8.32 (dd, J=8.0, 2.0 Hz, 1H), 7.56 (dd, J=8.1, 4.7 Hz, 1H), 7.51 (t, J=8.3 Hz, 1H), 6.89 (d, J=7.9 Hz, 1H), 6.46 (d, J=8.3 Hz, 1H), 6.312 (d, J=7.5 Hz, 1H), 3.49 (m, 1H), 2.77 (m, 2H), 2.17 (s, 3H), 2.05 (m, 2H), 1.89 (m, 2H), 1.70 (m, 2H). HPLC, Rt: 1.07 min. (purity 100.0%). LC/MS, M⁺(ESI): 352.4, M⁻(ESI): 350.4.

Example 71

N-{5-[(3-aminocyclohexyl)amino][1,2,4]triazolo[1,5-a]pyridin-2-yl}benzamide

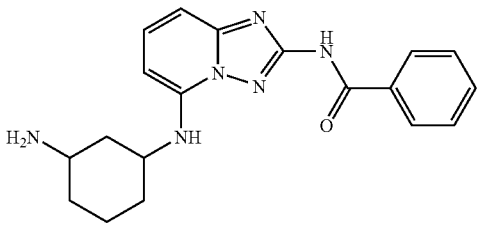

(71)

The title compound was prepared following procedure described for example 30 but starting from N-(5-chloro[1,2,4]triazolo[1,5-a]pyridin-2-yl)benzamide ((B3), 52 mg; 0.19 mmol; 1.0 eq) and 1,3-cyclohexanediamine (1.0 mL). The crude was directly purified by preparative HPLC (Starting with 45% ACN in water for 5 min, then up to 60% in 10 min.). The title compound was isolated after lyophilisation as a white powder (63 mg, 94%). HPLC, Rt: 1.84 min. (purity 98.2%). LC/MS, M⁺(ESI): 351.4, M⁻(ESI): 349.4.

Example 72

N-{5-[(1-methylpiperidin-4-yl)amino][1,2,4]triazolo[1,5-a]pyridin-2-yl}benzamide (72)

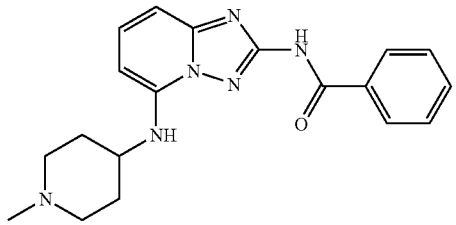

The title compound was prepared following procedure and work up described for example 71 but starting from N-(5-chloro[1,2,4]triazolo[1,5-a]pyridin-2-yl)benzamide ((B3), 100 mg; 0.37 mmol; 1.0 eq.) and 4-amino-1-methyl-piperidine (ABCR, 0.50 mL) as a white powder (59 mg, 46%). $^1$H NMR (DMSO-d$_6$) δ 10.91 (brs, 1H), 8.00 (d, J=7.2 Hz, 2H), 7.57 (m, 4H), 6.87 (d, J=8.3 Hz, 1H), 6.49 (d, J=8.3 Hz, 1H), 6.29 (d, J=7.9 Hz, 1H), 3.84 (m, 1H), 2.74 (m, 2H), 2.16 (s, 3H), 2.03 (m, 2H), 1.92 (m, 2H), 1.66 (m, 2H). HPLC, Rt: 1.70 min. (purity 99.4%). LC/MS, M$^+$(ESI): 351.4, M$^-$(ESI). 349.4.

Example 73

N-[5-(cyclopropylamino)-7-(trifluoromethyl)[1,2,4]triazolo[1,5-a]pyridin-2-yl]nicotinamide (73)

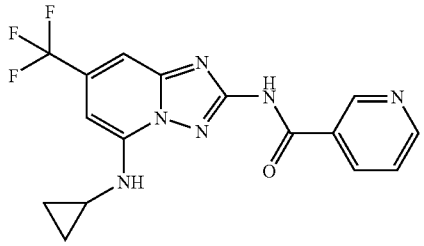

The title compound was prepared following procedure described for example 71 but starting from N-[5-chloro-7-(trifluoromethyl)[1,2,4]triazolo[1,5-a]pyridin-2-yl]nicotinamide ((B7), 50 mg; 0.14 mmol; 1.0 eq.) and cyclopropylamine (1.0 mL) as a white powder (30 mg, 59%). HPLC, Rt: 2.98 min. (purity 99.6%). LC/MS, M$^+$(ESI): 363.3, M$^-$(ESI): 361.3.

Example 74

N-[5-(cyclohexylamino)-7-(trifluoromethyl)[1,2,4]triazolo[1,5-a]pyridin-2-yl]nicotinamide (74)

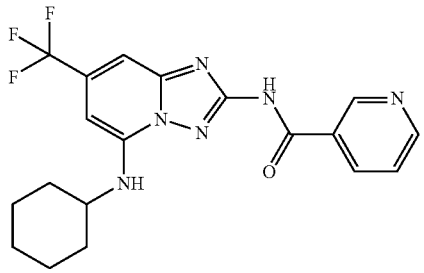

The title compound was prepared following procedure described for example 71 at rt but starting from N-[5-chloro-7-(trifluoromethyl)[1,2,4]triazolo[1,5-a]pyridin-2-yl]nicotinamide ((B7), 50 mg; 0.14 mmol; 1.0 eq.) and cyclohexylamine (1.0 mL) as a white powder (3 mg, 5%). HPLC, Rt: 3.78 min. (purity 100%). LC/MS, M$^+$(ESI): 405.3, M$^-$(ESI): 403.2.

Example 75

N-[5-(cycloheptylamino)-7-(trifluoromethyl)[1,2,4]triazolo[1,5-a]pyridin-2-yl]nicotinamide (75)

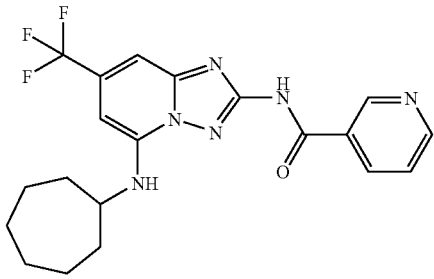

The title compound was prepared following procedure described for example 71 at rt but starting from N-[5-chloro-7-(trifluoromethyl)[1,2,4]triazolo[1,5-a]pyridin-2-yl]nicotinamide ((B7), 50 mg; 0.14 mmol; 1.0 eq.) and cycloheptylamine (1.0 mL) as a white powder (8 mg, 13%). HPLC, Rt: 3.85 min. (purity 95.9%). LC/MS, M$^+$(ESI): 419.3, M$^-$(ESI): 417.4.

Example 76

N-[5-(cyclopentylamino)-7-(trifluoromethyl)[1,2,4]triazolo[1,5-a]pyridin-2-yl]nicotinamide (76)

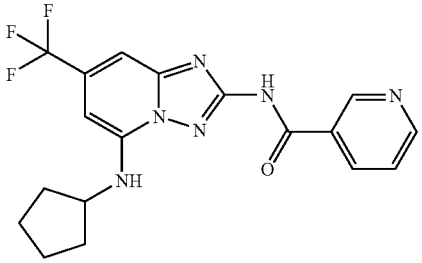

N-[5-chloro-7-(trifluoromethyl)[1,2,4]triazolo[1,5-a]pyridin-2-yl]nicotinamide ((B7), 50 mg; 0.14 mmol; 1.0 eq.) in cyclopentylamine (1.0 mL) was stirred at rt overnight. The reaction mixture was diluted with a saturated solution of NaHCO$_3$ (10 mL) and EtOAc (5 mL). The two phases were separated and the organic phase was washed four times with a saturated solution of NaHCO$_3$, after which the product precipitated in the organic phase. It was filtered, washed with a saturated solution of NaHCO$_3$ and EtOAc, dried under vacuum and isolated as a white solid (13 mg, 23%). HPLC, Rt: 3.54 min. (purity 100%). LC/MS, M$^+$(ESI): 391.3, M$^-$(ESI): 389.3.

Example 77

N-[5-[(cyclohexylmethyl)amino]-7-(trifluoromethyl)[1,2,4]triazolo[1,5-a]pyridin-2-yl]nicotinamide (77)

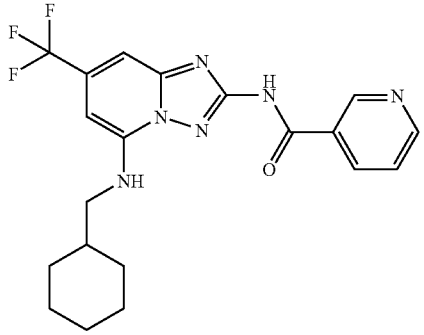

The title compound was prepared following procedure described for example 76 but starting from N-[5-chloro-7-(trifluoromethyl)[1,2,4]triazolo[1,5-a]pyridin-2-yl]nicotinamide ((B7), 50 mg; 0.14 mmol; 1.0 eq.) and cyclohexanemethylamine (500 µl) as a white powder (27 mg; 44%). HPLC, Rt: 4.11 min. (purity 99.8%). LC/MS, M+(ESI): 419.4, M−(ESI): 417.4.

Example 78

N-(6-bromo-5-methyl[1,2,4]triazolo[1,5-a]pyridin-2-yl)nicotinamide (78)

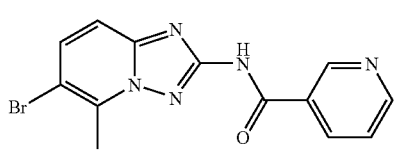

The title compound was prepared following procedure described for intermediate B1, but starting from 6-bromo-5-methyl[1,2,4]triazolo[1,5-a]pyridin-2-amine ((A8), 4.0 g; 17.62 mmol; 1.0 eq.) and nicotinoyl chloride hydrochloride (3.76 g; 21.1 mmol; 1.2 eq.) as a yellow solid (4.53 g; 77%). $^1$H NMR (DMSO-$d_6$) δ 11.54 (s, 1H), 9.13 (d, J=2.3 Hz, 1H), 9.78 (dd, J=4.9, 1.5 Hz, 1H), 8.34 (dt, J=7.9, 1.8 Hz, 1H), 7.85 (d, J=8 Hz, 1H), 7.63-7.54 (m, 2H), 2.8 (s, 3H). HPLC, Rt: 1.75 min. (purity 98.8%). LC/MS, M+(ESI): 334.2. CHN analysis: [$C_{13}H_{10}N_5OBr.1.0H_2O$] Corrected: C, 44.59%; H, 3.45%; N, 20.00%. Found: C, 44.68%; H, 3.41%; N, 19.97%.

Example 79

N-{5-[(3-hydroxycyclohexyl)amino][1,2,4]triazolo[1,5-a]pyridin-2-yl}nicotinamide (79)

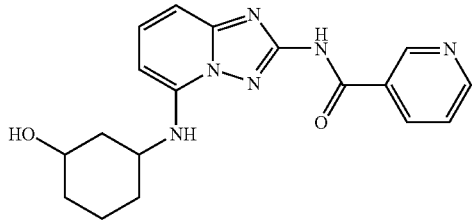

3-amino-cyclohexanol (Betapharma, 67.33 mg; 0.58 mmol; 2.0 eq.) was added to a mixture of N-(5-chloro[1,2,4]triazolo[1,5-a]pyridin-2-yl)nicotinamide ((B4), 80 mg; 0.29 mmol; 1.0 eq.), DIEA (76 mg; 0.58 mmol; 2.0 eq.) and activated Charcoal (8 mg) in tBuOH (0.8 mL). The reaction mixture was heated at 200° C. for 2×30 min under microwave irradiation. After this time, it was filtered on a celite pad and the cake was washed with ACN. The filtrate was directly purified by RP-HPLC (Starting with 15% ACN in water for 5 min, then up to 30% in 10 min.). The title compound was isolated after lyophilisation as a white powder (51 mg, 49%). HPLC, Rt: 2.14 min. (purity 98.0%). LC/MS, M+(ESI): 353.0, M−(ESI): 351.0.

Example 80

N-{5-[(4-tert-butylcyclohexyl)amino][1,2,4]triazolo[1,5-a]pyridin-2-yl}nicotinamide (80)

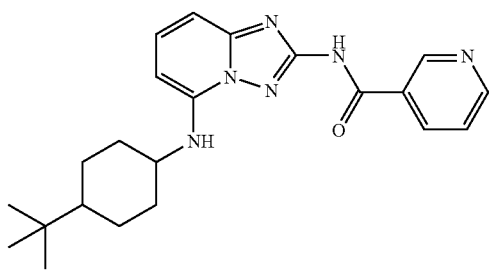

The title compound was prepared following procedure and work up described for example 79 but starting from N-(5-chloro[1,2,4]triazolo[1,5-a]pyridin-2-yl)nicotinamide ((B4), 80 mg; 0.29 mmol; 1.0 eq.) and 4-tert-butylcyclohexylamine (91 mg; 0.58 mmol; 2.0 eq.) as a white powder (32 mg, 27%). HPLC, Rt: 4.63 min. (purity 99.3%). LC/MS, M+(ESI): 393.1, M−(ESI): 391.1.

Example 81

N-[5-(tetrahydro-2H-pyran-3-ylamino)[1,2,4]triazolo[1,5-a]pyridin-2-yl]benzamide (81)

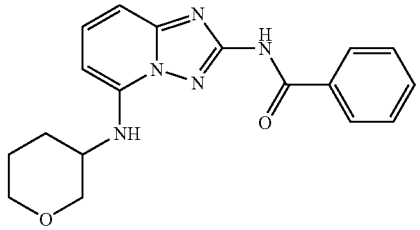

The title compound was prepared following procedure and work up described for example 30 but starting from N-(5-chloro[1,2,4]triazolo[1,5-a]pyridin-2-yl)benzamide ((B3), 100 mg; 0.37 mmol; 1.0 eq.) and tetrahydro-pyran-3-ylamine hydrochloride (CBI, 257 mg; 1.87 mmol; 5 eq.) in DMA (1 mL) as a white powder (32 mg, 26%). $^1$H NMR (DMSO-$d_6$) δ 11.05 (s, 1H), 8.00 (d, J=6.8 Hz, 2H), 7.48-7.63 (m, 4H), 6.91 (d, J=8.3 Hz, 1H), 6.46 (d, J=9.0 Hz, 1H), 6.36 (d, J=7.9 Hz, 1H), 3.86 (m, 1H), 3.71 (m, 2H), 3.50 (m, 2H), 2.06 (m, 1H), 1.22-1.97 (m, 3H). HPLC, Rt: 2.27 min. (purity 99.6%). LC/MS, M+(ESI): 338.1, M−(ESI): 336.0.

Example 82

N-[5-(cycloheptylamino)[1,2,4]triazolo[1,5-a]pyridin-2-yl]-4-(morpholin-4-ylmethyl)benzamide (82)

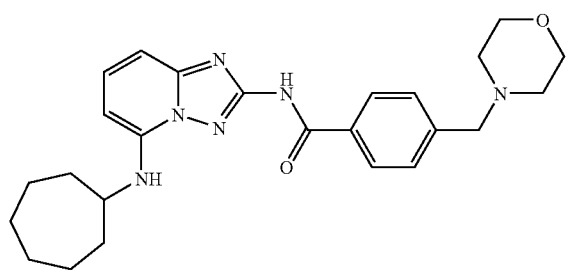

The title compound was prepared following procedure described for intermediate B1, but starting from $N^5$-cycloheptyl[1,2,4]triazolo[1,5-a]pyridine-2,5-diamine ((A10), 123 mg; 0.50 mmol; 1.0 eq.) and 4-(chloromethyl)benzoyl chloride (142 mg; 0.75 mmol; 1.5 eq.). Solvents were removed under reduced pressure to yield a gummy solid that was resuspended in morpholine (1.74 g; 20.0 mmol; 10.0 eq.) and the mixture was stirred at 60° C. for 2 h. After this time, reaction mixture was cooled down to rt, solvents were evaporated under reduced pressure and the residue washed with Et$_2$O (4×5 mL). A solid crystallized in the Et$_2$O phase which, after filtration, gave the title compound as a white solid (90 mg, 40%). HPLC, Rt: 3.99 min. (purity 98.9%). LC/MS, M$^+$(ESI): 423.1, M$^-$(ESI): 421.1.

Example 83

N-[5-(cyclohexylthio)[1,2,4]triazolo[1,5-a]pyridin-2-yl]nicotinamide (83)

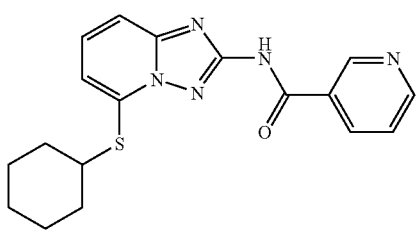

To a solution of N-(5-chloro[1,2,4]triazolo[1,5-a]pyridin-2-yl)nicotinamide ((B4), 136 mg; 0.5 mmol; 1.0 eq.) in dry THF (10 mL) was added in one pot cyclohexyl mercaptan (58 mg; 0.5 mmol; 1.0 eq.). The reaction mixture was stirred at rt for 14 h. The product precipitated upon addition of water after which filtration and washing with MeOH and Et$_2$O gave the title compound as a white solid (78 mg, 44%). HPLC, Rt: 2.94 min. (purity 94.6%). LC/MS, M$^+$(ESI): 354.1, M$^-$(ESI): 352.0.

Example 84

N-{5-[(trans-4-hydroxycyclohexyl)amino][1,2,4]triazolo[1,5-a]pyridin-2-yl}nicotinamide (84)

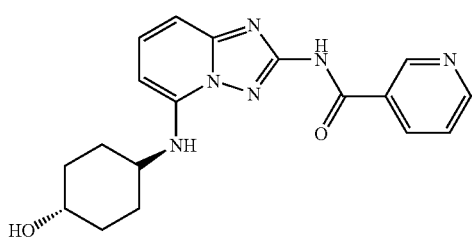

A solution of N-(5-chloro[1,2,4]triazolo[1,5-a]pyridin-2-yl)nicotinamide ((B4), 100 mg; 0.37 mmol; 1.0 eq.), trans-4-aminocyclohexanol hydrochloride (ABCR), 277 mg; 1.83 mmol; 5.0 eq.), DIEA (472 mg; 3.65 mmol; 10.0 eq.) in n-butanol (1.0 mL) was heated at 220° C. for 20 min under microwave irradiation. The reaction mixture was directly purified by reverse phase chromatography (Starting with water then up to 60% ACN in water in 40 min.). The title compound was isolated after lyophilisation as a white powder (31 mg, 24%). HPLC, Rt: 1.77 min. (purity 80.2%). LC/MS, M$^+$(ESI): 353.1, M$^-$(ESI): 351.1.

Example 85

N-[5-(cyclobutylamino)-7-(trifluoromethyl)[1,2,4]triazolo[1,5-a]pyridin-2-yl]nicotinamide (85)

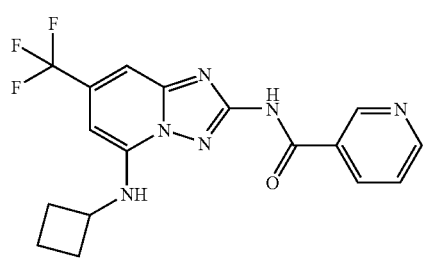

The title compound was prepared following procedure described for example 84, but starting from N-[5-chloro-7-(trifluoromethyl)[1,2,4]triazolo[1,5-a]pyridin-2-yl]nicotinamide ((B7), 100 mg; 0.3 mmol; 1.0 eq.) and cyclobutylamine (125 µl; 0.150 mmol; 5.0 eq.) at 120° C. for 30 min. under microwave irradiations. Solvents were removed under vacuum to dryness after which the residue was triturated with water, filtered and washed with EtOAc to give the title compound as a white powder (59 mg; 53%). $^1$H NMR (DMSO-d$_6$) δ 11.4 (s, 1H), 9.15 (d, J=2.2 Hz, 1H), 8.79 (dd, J=1.5, 4.5 Hz, 1H), 8.35 (dt, J=1.8, 7.9 Hz, 1H), 7.63-7.56 (m, 2H), 7.32 (bs, 1H), 6.36 (d, J=1.5 Hz, 1H), 4.32-4.24 (m, 1H), 2.43-2.34 (m, 2H), 2.25-2.18 (m, 2H), 1.79-1.70 (m, 2H). HPLC, Rt: 3.20 min. (purity 94.8%). LC/MS, M$^+$(ESI): 377.0, M$^-$(ESI): 375.0.

Example 86

N-[5-(cyclohexylamino)[1,2,4]triazolo[1,5-a]pyridin-2-yl]-6-morpholin-4-ylnicotinamide (86)

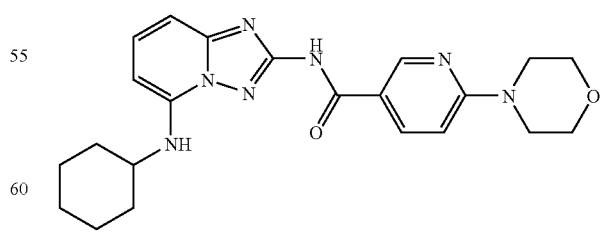

The title compound was prepared following procedure described for intermediate B1, but starting from $N^5$-cyclohexyl[1,2,4]triazolo[1,5-a]pyridine-2,5-diamine ((A9), 174 mg; 0.75 mmol; 1.0 eq.) and 6-morpholinonicotinoyl chloride (255 mg; 1.12 mmol; 1.5 eq.) as a white solid (15 mg, 5%). HPLC, Rt: 2.83 min. (purity 99.0%). LC/MS, M$^+$(ESI): 422.2, M$^-$(ESI): 420.1.

Example 87

N-[5-(cyclohexylamino)[1,2,4]triazolo[1,5-a]pyridin-2-yl]-4-[(dimethylamino)methyl]benzamide (87)

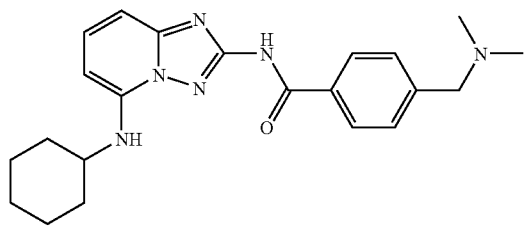

The title compound was prepared following procedure described for example 82, but starting from N$^5$-cyclohexyl[1,2,4]triazolo[1,5-a]pyridine-2,5-diamine ((B8), 288 mg; 0.75 mmol; 1.0 eq.) and dimethylamine (2 mL, 2M solution in THF) as a yellow powder (91 mg, 31%). HPLC, Rt: 2.65 min. (purity 97.4%). LC/MS, M$^+$(ESI): 393.1, M$^-$(ESI): 391.1.

Example 88

N-[5-(cyclohexylamino)[1,2,4]triazolo[1,5-a]pyridin-2-yl]-3-(morpholin-4-ylmethyl)benzamide (88)

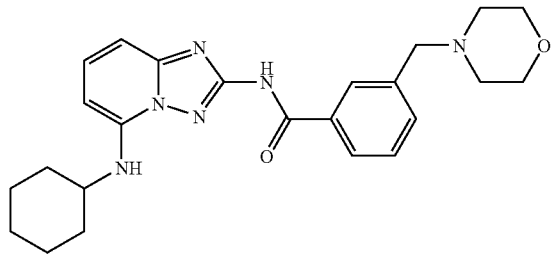

The title compound was prepared following procedure described for example 82, but starting from N$^5$-cyclohexyl[1,2,4]triazolo[1,5-a]pyridine-2,5-diamine ((B8), 173 mg; 0.75 mmol; 1.0 eq.) and morpholine (653 mg, 7.5 mmol, 10 eq.) as an off white powder (120 mg, 37%). HPLC, Rt: 2.69 min. (purity 99.3%). LC/MS, M$^+$(ESI): 435.2, M$^-$(ESI): 433.1.

Example 89

N-[5-[(cyclopropylmethyl)amino]-7-(trifluoromethyl)[1,2,4]triazolo[1,5-a]pyridin-2-yl]nicotinamide (89)

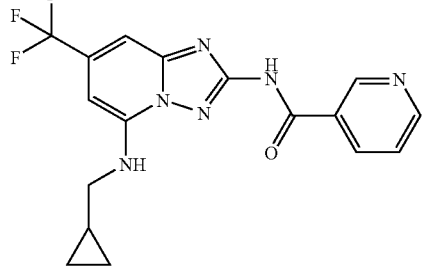

The title compound was prepared following procedure described for example 85, but starting from N-[5-chloro-7-(trifluoromethyl)[1,2,4]triazolo[1,5-a]pyridin-2-yl]nicotinamide ((B7), 50 mg; 0.15 mmol; 1.0 eq.) and (aminomethyl)cyclopropane (52 μl; 0.73 mmol; 5.0 eq.) as a white solid (43 mg, 78%). HPLC, Rt: 3.19 min. (purity 78.6%). LC/MS, M$^+$(ESI): 420.0, M$^-$(ESI): 418.0.

Example 90 methyl trans-4-{[2-[(pyridin-3-ylcarbonyl)amino]-7-(trifluoromethyl)[1,2,4]triazolo[1,5-a]pyridin-5-yl]amino}cyclohexanecarboxylate (90)

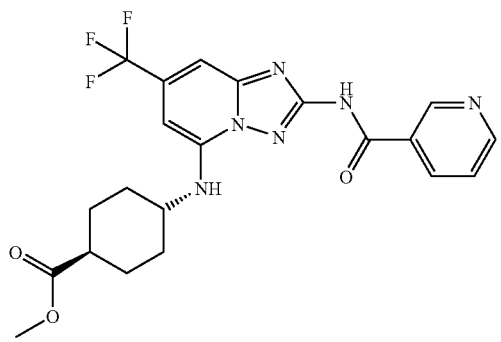

The title compound was prepared following procedure described for example 85, but starting from N-[5-chloro-7-(trifluoromethyl)[1,2,4]triazolo[1,5-a]pyridin-2-yl]nicotinamide ((B7), 50 mg; 0.15 mmol; 1.0 eq.) and trans-4-aminocyclohexylcarboxylic acid methyl ester hydrochloride (IRIS), 52 μl; 0.73 mmol; 5.0 eq.) as a white powder (23 mg, 34%). HPLC, Rt: 3.33 min. (purity 96.4%). LC/MS, M$^+$(ESI): 463.1, M$^-$(ESI): 461.1.

Example 91

N-[5-{[(1RS,2RS)-2-(hydroxymethyl)cyclohexyl]amino}-7-(trifluoromethyl)[1,2,4]triazolo[1,5-a]pyridin-2-yl]nicotinamide (91)

The title compound was prepared following procedure described for example 85, but starting from N-[5-chloro-7-(trifluoromethyl)[1,2,4]triazolo[1,5-a]pyridin-2-yl]nicotinamide ((B7), 50 mg; 0.15 mmol; 1.0 eq.) and trans-2-hydroxymethyl-1-cyclohexylamine hydrochloride (121 mg; 0.73 mmol; 5.0 eq.) as a white solid (32 mg, 50%). HPLC, Rt: 3.00 min. (purity 89.6%). LC/MS, M$^+$(ESI): 435.1, M$^-$(ESI): 433.0.

Example 92

N-[6-bromo-5-(cyclohexylamino)[1,2,4]triazolo[1,5-a]pyridin-2-yl]nicotinamide

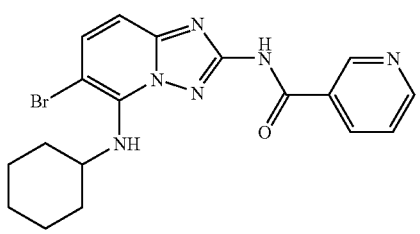
(92)

The title compound was prepared following procedure described for intermediate B1, but starting from 6-bromo-$N^5$-cyclohexyl[1,2,4]triazolo[1,5-a]pyridine-2,5-diamine ((A14), 616 mg; 1.99 mmol; 1.0 eq.) and nicotinoyl chloride hydrochloride (424 mg; 2.38 mmol; 1.2 eq.) as a beige powder (99 mg, 12%). HPLC, Rt: 3.41 min. (purity 94.6%). LC/MS, $M^+$(ESI): 416.9.

Example 93

N-[5-(cycloheptylamino)[1,2,4]triazolo[1,5-a]pyridin-2-yl]tetrahydro-2H-pyran-4-carboxamide

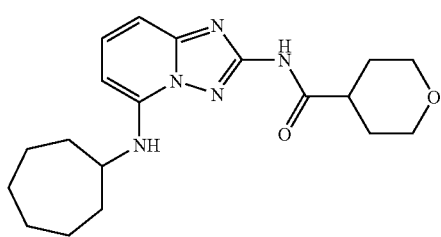
(93)

The title compound was prepared following procedure described for intermediate B1, but starting from $N^5$-cycloheptyl[1,2,4]triazolo[1,5-a]pyridine-2,5-diamine ((A10), 50 mg; 0.20 mmol; 1.0 eq.) and tetrahydro-2H-pyran-4-carbonyl chloride (45 mg; 0.30 mmol; 1.5 eq.) as a white solid (33 mg, 46%). HPLC, Rt: 3.02 min. (purity 96.9%). LC/MS, $M^+$(ESI): 358.0, $M^-$(ESI): 356.0.

Example 94

N-[5-(2-methylprop-1-en-1-yl)[1,2,4]triazolo[1,5-a]pyridin-2-yl]nicotinamide dihydrochloride

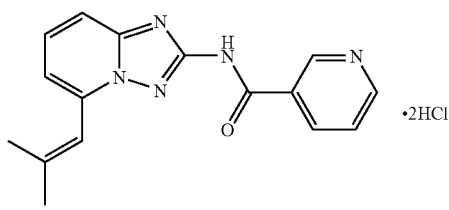
(94)

N-(5-chloro[1,2,4]triazolo[1,5-a]pyridin-2-yl)nicotinamide ((B4), 141.00 mg; 0.52 mmol; 1.00 eq.), 2,2-dimethylethenylboronic acid (Synthonix, 102.96 mg; 1.03 mmol; 2.00 eq.), cesium fluoride (156.53 mg; 1.03 mmol; 2.00 eq.) and bis(triphenylphosphine)palladium(II) chloride (36.16 mg; 0.05 mmol; 0.10 eq.) were flushed with nitrogen in a sealed vial. THF (degassed with nitrogen, 1.50 mL) and water (1 mL) were then added and the mixture was heated at 120° C., O/N in an oil bath. A solution of saturated $NH_4Cl$ was added and the reaction mixture was extracted with EtOAc (twice). Combined Organic phases were washed with brine, dried over magnesium sulfate, filtered and concentrated to give 186 mg of a yellow foam. Hydrochloride salt was then obtained by addition of $Et_2O$/HCl (1 M solution) to a solution of this crude in DCM. The precipitate obtained was filtered and dried under vacuum at 40° C. to give the title compound as a beige solid (181 mg, 96%). HPLC, Rt: 2.05 min. (purity 92.3%). LC/MS, $M^+$(ESI): 293.9, $M^-$(ESI): 291.9.

Example 95

N-(3-oxo-3-{[5-(1H-pyrazol-1-yl)[1,2,4]triazolo[1,5-a]pyridin-2-yl]amino}propyl)benzamide

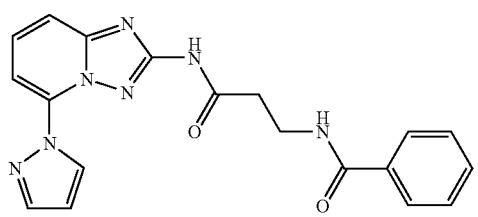
(95)

The title compound was prepared following procedure and work up described for example 94 but starting from 5-(1H-pyrazol-1-yl)[1,2,4]triazolo[1,5-a]pyridin-2-amine ((A12), 43 mg; 0.27 mmol; 1.0 eq.) as a white solid (13 mg, 13%). HPLC, Rt: 2.41 min. (purity 87.3%). LC/MS, $M^+$(ESI): 376.0, $M^-$(ESI): 374.0.

Example 96

N-(3-{[5-(3-furyl)[1,2,4]triazolo[1,5-a]pyridin-2-yl]amino}-3-oxopropyl)benzamide

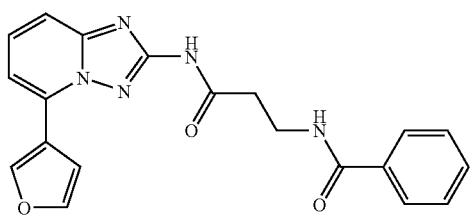
(96)

The title compound was prepared following procedure and work up described for example 94 but starting from 5-(3-furyl)[1,2,4]triazolo[1,5-a]pyridin-2-amine ((A2), 43 mg; 0.27 mmol; 1.0 eq.) as a white solid (52 mg, 51%). HPLC, Rt: 2.72 min. (purity 84.8%). LC/MS, $M^+$(ESI): 376.0, $M^-$(ESI): 374.0.

Example 97

N-(3-{[5-(2-furyl)[1,2,4]triazolo[1,5-a]pyridin-2-yl]amino}-3-oxopropyl)benzamide

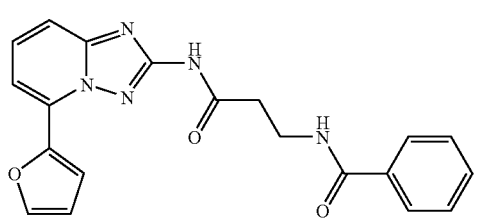
(97)

The title compound was prepared following procedure and work up described for example 94 but starting from 5-(2- furyl)[1,2,4]triazolo[1,5-a]pyridin-2-amine ((A16), 43 mg; 0.27 mmol; 1.0 eq.) as a white solid (51 mg, 42%). HPLC, Rt: 2.85 min. (purity 92.7%). LC/MS, M⁺(ESI): 447.0, M⁻(ESI): 445.0.

Example 98

N-(3-{[5-(cyclohexylamino)[1,2,4]triazolo[1,5-a]pyridin-2-yl]amino}-3-oxopropyl)benzamide (98)

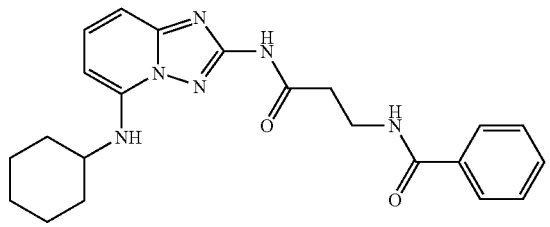

The title compound was prepared following procedure and work up described for example 94 but starting from $N^5$-cyclohexyl[1,2,4]triazolo[1,5-a]pyridine-2,5-diamine ((A9), 49 mg; 0.27 mmol; 1.0 eq.) as a white solid (28 mg, 25%). HPLC, Rt: 3.22 min. (purity 87.4%). LC/MS, M⁺(ESI): 407.1, M⁻(ESI): 405.0.

Example 99

N-[5-(isopropylamino)-7-(trifluoromethyl)[1,2,4]triazolo[1,5-a]pyridin-2-yl]nicotinamide (99)

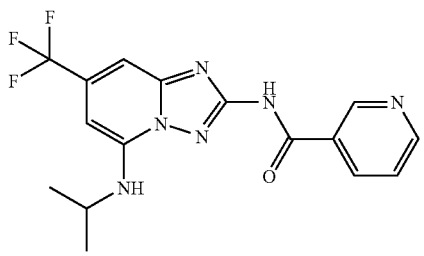

The title compound was prepared following procedure and work up described for example 85 but starting from N-[5-chloro-7-(trifluoromethyl)[1,2,4]triazolo[1,5-a]pyridin-2-yl]nicotinamide ((B7), 50 mg; 0.15 mmol; 1.0 eq.) and isopropylamine (43 mg, 0.73 mmol; 5.0 eq.) as a white solid (8 mg, 15%). HPLC, Rt: 3.09 min. (purity 87.7%). LC/MS, M⁺(ESI): 365.0, M⁻(ESI): 363.0.

Example 100

N-[5-(sec-butylamino)-7-(trifluoromethyl)[1,2,4]triazolo[1,5-a]pyridin-2-yl]nicotinamide (100)

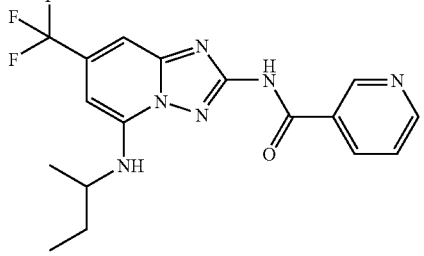

The title compound was prepared following procedure and work up described for example 85 but starting from N-[5-chloro-7-(trifluoromethyl)[1,2,4]triazolo[1,5-a]pyridin-2-yl]nicotinamide ((B7), 50 mg; 0.15 mmol; 1.0 eq.) and sec-butylamine (53.50 mg; 0.73 mmol; 5.0 eq.) as a white solid (4 mg, 7%). HPLC, Rt: 3.44 min. (purity 89.4%). LC/MS, M⁺(ESI): 379.1, M⁻(ESI): 377.0.

Example 101

N-[5-(methylamino)-7-(trifluoromethyl)[1,2,4]triazolo[1,5-a]pyridin-2-yl]nicotinamide (101)

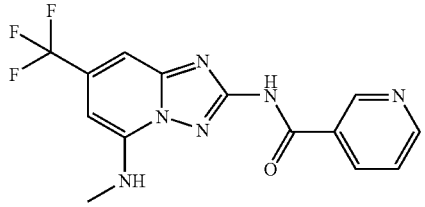

The title compound was prepared following procedure and work up described for example 85 but starting from N-[5-chloro-7-(trifluoromethyl)[1,2,4]triazolo[1,5-a]pyridin-2-yl]nicotinamide ((B7), 50 mg; 0.15 mmol; 1.0 eq.) and methylamine (1.46 mL of a 2M solution in MeOH; 0.73 mmol; 5.0 eq.) as a white solid (15 mg, 30%). HPLC, Rt: 2.47 min. (purity 96.6%). LC/MS, M⁺(ESI): 337.0, M⁻(ESI): 335.0.

Example 102

N-[8-(3-furyl)[1,2,4]triazolo[1,5-a]pyridin-2-yl]benzamide (102)

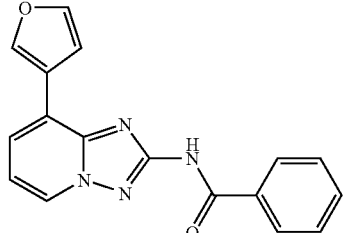

The title compound was prepared following procedure and work up described for example 56 but starting from N-(8-bromo[1,2,4]triazolo[1,5-a]pyridin-2-yl)benzamide ((B9), 159 mg; 0.50 mmol; 1.0 eq.) and furan-3-boronic acid (112 mg; 1.0 mmol; 2.0 eq.) as a white powder (80 mg, 52%). HPLC, Rt: 3.26 min. (purity 99.6%). LC/MS, M⁺(ESI): 305.0, M⁻(ESI): 303.1.

Example 103

N-[5-(cyclohexyloxy)[1,2,4]triazolo[1,5-a]pyridin-2-yl]-2-(3-methoxyphenyl)acetamide (103)

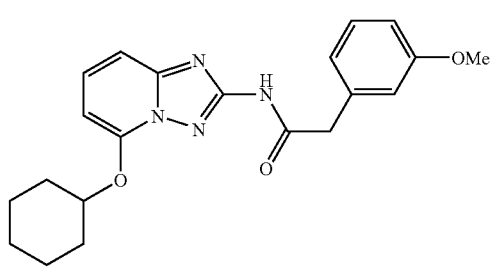

The title compound was prepared following procedure and work up described for intermediate B1 but starting from 5-(cyclohexyloxy)[1,2,4]triazolo[1,5-a]pyridin-2-amine ((A11), 80 mg; 0.34 mmol; 1.0 eq.) and 3-methoxyphenylacetyl chloride (64 µl; 0.41 mmol; 1.2 eq.) as a white powder (11 mg, 8%). HPLC, Rt: 3.60 min. (purity 88.2%). LC/MS, M+(ESI): 381.1, M−(ESI): 379.1.

Example 104

N-[5-(cyclohexyloxy)[1,2,4]triazolo[1,5-a]pyridin-2-yl]nicotinamide (104)

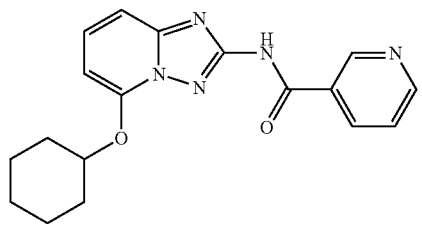

The title compound was prepared following procedure and work up described for intermediate B1 but starting from 5-(cyclohexyloxy)[1,2,4]triazolo[1,5-a]pyridin-2-amine ((A11), 268 mg; 1.15 mmol; 1.0 eq.) and nicotinoyl chloride hydrochloride (247 mg; 1.38 mmol; 1.2 eq.) as an off-white foam (230 mg, 59%). HPLC, Rt: 2.36 min. (purity 94.7%). LC/MS, M−(ESI): 336.1.

Example 105

N-[5-(cyclohexylamino)[1,2,4]triazolo[1,5-a]pyridin-2-yl]-6-(2-pyrrolidin-1-ylethyl)nicotinamide (105)

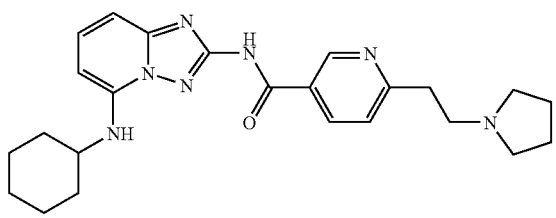

The title compound was prepared following procedure described for intermediate B1 but starting from N5-cyclohexyl[1,2,4]triazolo[1,5-a]pyridine-2,5-diamine ((A9), 116 mg; 0.5 mmol; 1.0 eq.) and 6-(2-pyrrolidin-1-ylethyl)nicotinoyl chloride (239 mg, 1.0 mmol; 2.0 eq.) as a white powder (130 mg, 60%). HPLC, Rt: 2.67 min. (purity 99.9%). LC/MS, M+(ESI): 434.1, M−(ESI): 432.1.

Example 106

N-[5-(cyclohexylamino)[1,2,4]triazolo[1,5-a]pyridin-2-yl]-6-(morpholin-4-ylmethyl)nicotinamide Step a) Formation of potassium 6-(hydroxymethyl)pyridine-3-carboxylate

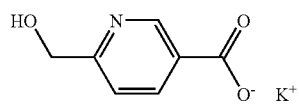

An aqueous solution of potassium hydroxide (40.4 mmol, 8 mL, 5 N, 2.0 eq.) was added to a solution of ethyl 6-(hydroxymethyl)pyridine-3-carboxylate (3.7 g; 20.4 mmol; 1.0 eq.) (J. Med. Chem. 2004, 47, 5230-5234) in THF (80 mL). The resulting reaction mixture was stirred at rt for 3 h. The precipitate was collected by filtration and dried on under vacuum to give the title compound as a white powder (3.6 g, 92%).

Step b) Formation of 6-(chloromethyl)pyridine-3-carbonyl chloride hydrochloride

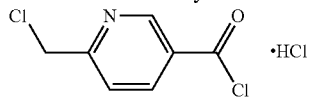

To a suspension of potassium 6-(hydroxymethyl)pyridine-3-carboxylate (96 mg; 0.50 mmol; 1.0 eq.) in DCM (1 mL) was added DMF (0.07 mg; 0.02 eq., 0.01 mmol). The mixture was chilled at 0° C. Then oxalyl chloride (317 mg; 2.5 mmol; 5.0 eq.) was added dropwise and the resulting mixture was stirred 4 h at rt. Evaporation of the solvent gave a black line powder without further purification in the next step.

Step c) Formation of N-[5-(cyclohexylamino)[1,2,4]triazolo[1,5-a]pyridin-2-yl]-6-(morpholin-4-ylmethyl)nicotinamide (106)

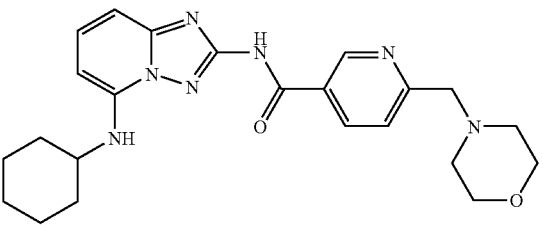

Pyridine (198 mg; 2.5 mmol; 5.0 eq.) was added to a solution of N5-cyclohexyl[1,2,4]triazolo[1,5-a]pyridine-2,5-diamine ((A9), 116 mg; 0.50 mmol; 1.0 eq.) in DCM (2.0 mL). 6-(chloromethyl)pyridine-3-carbonyl chloride hydrochloride (190 mg; 1.0 mmol; 2.0 eq.) was added and the resulting black solution was stirred under reflux for 14 h. The solvents were evaporated to yield a black oil. Morpholine (218 mg; 2.5 mmol; 5.0 eq.) and THF (0.5 mL) were added to this residue, and the mixture was then stirred and heated at 60° C. for 12 h. Purification by RP-HPLC (Waters Sunfire™ Prep C18 OBD™ 5 µM, 100×49 mm) following a gradient starting with 20/80 (0.1% formic acid in CH3CN/0.1% formic acid in H2O) up to 95/5 in 12 min. The fractions were collected and lyophilized to give the title compound as a white powder (20 mg, 9%). HPLC, Rt: 2.11 min. (purity 100%). LC/MS, M+(ESI): 436.3.

Example 107

The title compound was acquired from Biofocus DPI (UK) cat. number: 320__4252__0343.

(107)

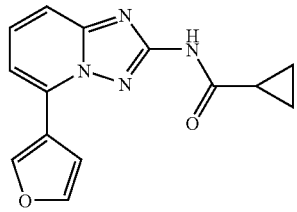

Example 108

N-[5-(3-thienyl)[1,2,4]triazolo[1,5-a]pyridin-2-yl]benzamide

The title compound was acquired from Biofocus DPI (UK) cat. Number: 320__4251__0074.

(108)

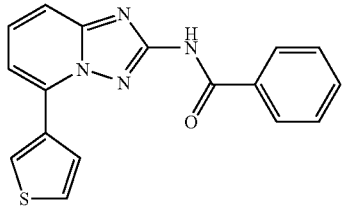

Example 109

N-[5-(3-furyl)[1,2,4]-triazolo[1,5-a]pyridin-2-yl]benzamide

The title compound was acquired from Biofocus DPI (UK) cat. number: 320__4251__0343.

(109)

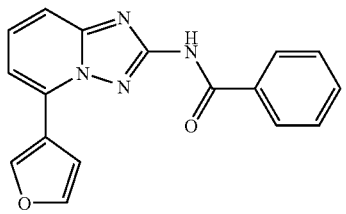

Example 110

N-[5-(3-furyl)[1,2,4]triazolo[1,5-a]pyridin-2-yl]benzamide

The title compound was acquired from Biofocus DPI (UK), cat. number: 320__4262__0343.

(110)

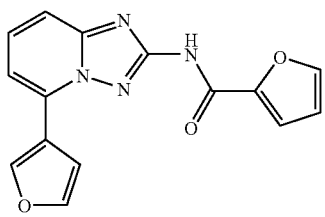

Example 111

N-[6-(4-hydroxy-3-methoxyphenyl)[1,2,4]triazolo[1,5-a]pyridin-2-yl]acetamide

The title compound was acquired from Biofocus DPI (UK), cat. number: 395__2182__0314.

(111)

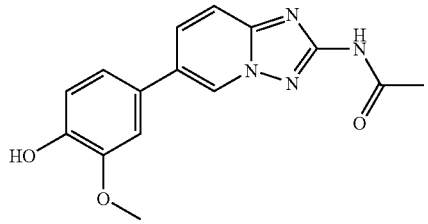

Example 112

N-[6-(4-hydroxy-3,5-dimethylphenyl)[1,2,4]triazolo[1,5-a]pyridin-2-yl]nicotinamide (112)

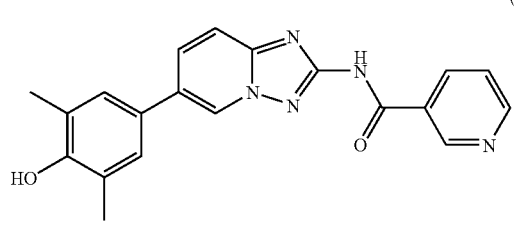

The title compound was prepared following procedure described for example 113 but using the N-(6-bromo-[1,2,4]triazolo[1,5-a]pyridin-2-yl)-benzamide ((B5), 95 mg, 0.3 mmol, 1 mol eq.) and the 2,6-dimethyl-4-(4,4,5,5-tetramethyl-1,3,2-dioxaborolan-2-yl)phenol (89 mg, 0.36 mmol, 1.2 mol eq.) as a white solid (8.1 mg, 8%). HPLC, Rt: 1.75 min (purity: 98%). LC/MS M+(ESI): 360.3.

Example 113

4-[2-(benzoylamino)[1,2,4]triazolo[1,5-a]pyridin-6-yl]-N-[2-(dimethylamino)ethyl]benzamide (113)

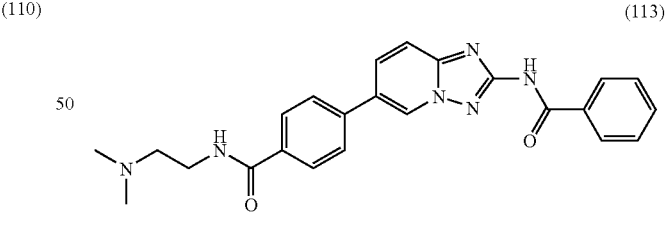

To a reaction vessel containing N-(6-bromo-[1,2,4]triazolo[1,5-a]pyridin-2-yl)-benzamide ((B5), 95 mg, 0.3 mmol, 1 mol eq.), N-(2-dimethylamino-ethyl)-4-boronic acid-benzamide (85 mg, 0.36 mmol, 1.2 mol eq.) and cesium fluoride (135 mg, 0.9 mmol, 3 mol eq.) in DMF (0.75 mL) and H$_2$O (0.5 mL) was added bis-triphenylphosphine palladium dichloride (0.009 mmol, 3 mol %) in DMF (0.25 mL). The vessel was purged with nitrogen, capped and heated at 95° C. for approximately 18 hours. The reaction mixture was cooled to room temperature, filtered and the residue dissolved in DMSO (1.5 mL) and purified by reverse phase preparatory HPLC to give the title compound as a white solid (30.4 mg, 24%). HPLC, Rt: 1.74 min (purity: 99%). LC/MS M⁺(ESI): 429.3, M⁻(ESI) 427.4.

Example 114

N-[6-(1H-pyrazol-4-yl)[1,2,4]triazolo[1,5-a]pyridin-2-yl]benzamide

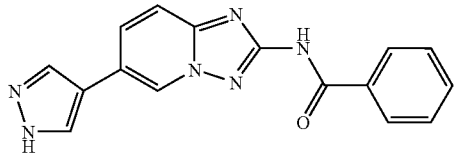
(114)

The title compound was prepared following procedure described for example 112 but starting from N-(6-bromo-[1,2,4]triazolo[1,5-a]pyridin-2-yl)-benzamide ((B5), 95 mg, 0.3 mmol, 1 eq.) and 4-(4,4,5,5-tetramethyl-1,3,2-dioxaborolan-2-yl)-1h-pyrazole (Boron-Mol, 85 mg, 0.36 mmol, 1.2 mol eq.) as a white solid (6.2 mg, 7%). HPLC, Rt: 2.26 min (purity: 99%). LC/MS M⁺(ESI): 305.2.

Example 115

N-{5-[(cyclohexylmethyl)amino][1,2,4]triazolo[1,5-a]pyridin-2-yl}nicotinamide

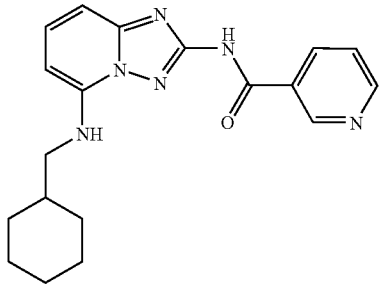
(115)

To a microwave vial (0.5-2 mL) was added N-(5-bromo[1,2,4]triazolo[1,5-a]pyridin-2-yl)nicotinamide (Intermediate B2, 60 mg, 0.19 mmol, 1 equivalent), diisopropylethylamine (0.05 mL, 0.30 mmol, 1.5 equivalent), cyclohexyl-methylamine (34 mg, 0.3 mmol, 1.5 equivalent) in butanol (0.6 mL). The mixture was heated in a Biotage initiator 60 microwave at 220° C. for 30 minutes. The reaction mixture was cooled and the solvent removed in vacuo. The residue dissolved in DMSO (1.5 mL) and purified by reverse phase preparatory HPLC to give the title compound as a white solid (4.0 mg, 6%). HPLC, Rt: 2.56 min (purity: 99%). LC/MS M⁺(ESI): 351.2, M⁻(ESI) 349.2.

Example 116

N-{5-[(4-hydroxycyclohexyl)amino][1,2,4]triazolo[1,5-a]pyridin-2-yl}-3-methoxybenzamide

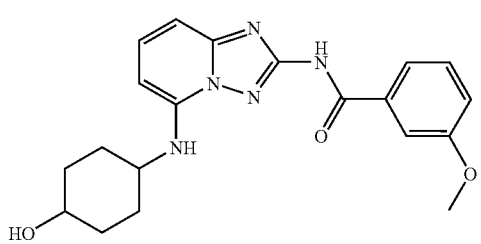
(116)

A sealed vessel containing N-(5-bromo-[1,2,4]triazolo[1,5-a]pyridin-2-yl)-3-methoxybenzamide (69 mg, 0.20 mmol, 1 mol eq.), trans-aminocyclohexanol (35 mg, 0.30 mmol, 1.5 mol eq.), di-iso-propylethylamine (60 µL, 0.32 mmol, 1.6 mol eq.) and n-butanol (0.75 mL) was irradiated at 220° C., with stirring, for 20 minutes. The solvent was removed in vacuo and the residue dissolved in DMSO (1.5 mL) and purified by reverse phase preparatory HPLC to give the title compound as a beige solid (27.5 mg, 36%). HPLC, Rt: 1.86 min (purity: 100%). LC/MS M⁺(ESI): 382.3, M⁻(ESI) 380.3.

Example 117

N-[5-(cyclopentylamino)[1,2,4]triazolo[1,5-a]pyridin-2-yl]-2-furamide

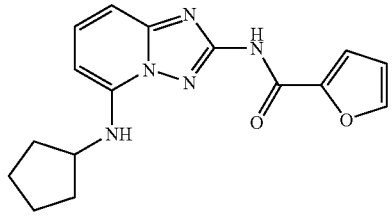
(117)

A sealed vessel containing furan-2-carboxylic acid (5-bromo-[1,2,4]triazolo[1,5-a]pyridin-2-yl)-amide (61 mg, 0.20 mmol, 1 mol eq.), cyclopentylamine (26 mg, 0.30 mmol, 1.5 mol eq.), di-iso-propylethylamine (60 pt, 0.32 mmol, 1.6 mol eq.) and n-butanol (0.75 ml) was irradiated at 220° C., with stirring, for 20 minutes. The solvent was removed in vacuo and the residue dissolved in DMSO (1.5 mL) and purified by reverse phase preparatory HPLC to give the title compound as a white solid (28.4 mg, 46%). HPLC, Rt: 2.32 min (purity: 97%). LC/MS M⁺(ESI): 312.3.

Example 118

N-[7-chloro-5-(cyclobutylamino)[1,2,4]triazolo[1,5-a]pyridin-2-yl]nicotinamide

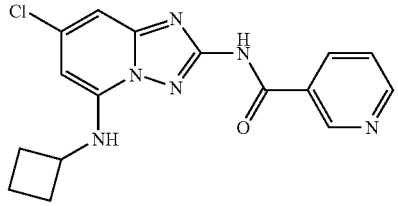
(118)

The title compound was prepared following procedure described for example 84, but starting from N-(5,7-dichloro[1,2,4]triazolo[1,5-a]pyridin-2-yl)nicotinamide ((B10), 100 mg; 0.32 mmol; 1.0 eq) and cyclobutylamine (139 µL; 1.62 mmol; 5.0 eq) heated at 180° C. for 1800 s after which solvents were evaporated under vacuum, then resuspended in water, filtered and washed with EtOAc to give the title compound as a white solid (23 mg, 21%). HPLC, Rt: 2.95 min. (purity 96.7%). LC/MS, M⁺(ESI): 342.8, M⁻(ESI): 340.9.

Example 119

N-[7-chloro-5-(cyclopentylamino)[1,2,4]triazolo[1,5-a]pyridin-2-yl]nicotinamide

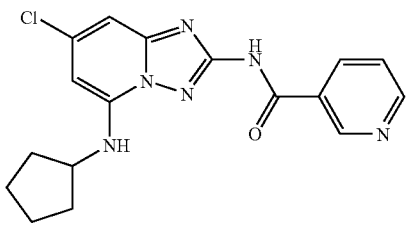
(119)

The title compound was prepared following procedure and work up described for example 118, but starting from N-(5,7-dichloro[1,2,4]triazolo[1,5-a]pyridin-2-yl)nicotinamide ((B10), 100 mg; 0.32 mmol; 1.0 eq) and cyclopentylamine (161 µL; 1.62 mmol; 5.0 eq) to give the title compound as a white solid (5 mg, 4%). HPLC, Rt: 3.20 min. (purity 92.3%). LC/MS, M$^+$(ESI): 356.9, M$^-$(ESI): 354.9.

Example 120

N-[7-chloro-5-(cyclohexylamino)[1,2,4]triazolo[1,5-a]pyridin-2-yl]nicotinamide

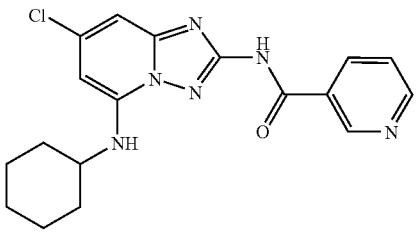
(120)

The title compound was prepared following procedure and work up described for example 118, but starting from N-(5,7-dichloro[1,2,4]triazolo[1,5-a]pyridin-2-yl)nicotinamide ((B10), 100 mg; 0.32 mmol; 1.0 eq) and cyclohexylamine (187 µL; 1.62 mmol; 5.0 eq) to give the title compound as a white solid (26 mg, 22%). HPLC, Rt: 3.48 min. (purity 98.5%). LC/MS, M$^+$(ESI): 370.9, M$^-$(ESI): 368.9.

Example 121

N-[5-(sec-butylamino)-7-chloro[1,2,4]triazolo[1,5-a]pyridin-2-yl]nicotinamide

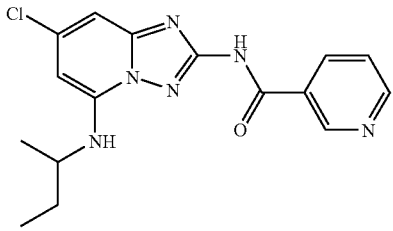
(121)

The title compound was prepared following procedure and work up described for example 118, but starting from N-(5,7-dichloro[1,2,4]triazolo[1,5-a]pyridin-2-yl)nicotinamide ((B10), 100 mg; 0.32 mmol; 1.0 eq) and sec-butylamine (118 mg; 1.62 mmol; 5.0 eq) to give the title compound as a white solid (15 mg, 13%). HPLC, Rt: 3.07 min. (purity 96.3%). LC/MS, M$^+$(ESI): 344.8, M$^-$(ESI): 342.9.

Example 122

N-[7-chloro-5-(cyclopropylamino)[1,2,4]triazolo[1,5-a]pyridin-2-yl]nicotinamide

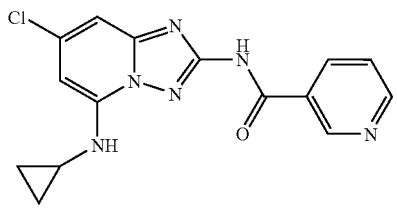
(122)

The title compound was prepared following procedure and work up described for example 118, but starting from N-(5,7-dichloro[1,2,4]triazolo[1,5-a]pyridin-2-yl)nicotinamide ((B10), 100 mg; 0.32 mmol; 1.0 eq) and cyclopropylamine (113 µL; 1.62 mmol; 5.00 eq) to give the title compound as a white solid (50 mg, 43%). HPLC, Rt: 2.59 min. (purity 92.6%). LC/MS, M$^+$(ESI): 328.8, M$^-$(ESI): 326.9.

Example 123

N-[5-[(2-methoxyethyl)amino]-7-(trifluoromethyl)[1,2,4]triazolo[1,5-a]pyridin-2-yl]nicotinamide

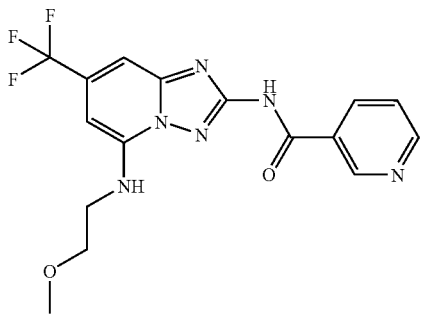
(123)

The title compound was prepared following procedure and work up described for example 118, but starting from N-[5-chloro-7-(trifluoromethyl)[1,2,4]triazolo[1,5-a]pyridin-2-yl]nicotinamide ((B7), 50 mg; 0.14 mmol; 1.0 eq) and 2-methoxyethylamine (55.0 mg; 0.73 mmol; 5.0 eq), heated at 120° C., to give the title compound as a white solid (23 mg, 40%). HPLC, Rt: 2.70 min. (purity 98.1%). LC/MS, M$^+$(ESI): 380.8, M$^-$(ESI): 378.9.

Example 124

N-[5-[(3-hydroxypropyl)amino]-7-(trifluoromethyl)[1,2,4]triazolo[1,5-a]pyridin-2-yl]nicotinamide

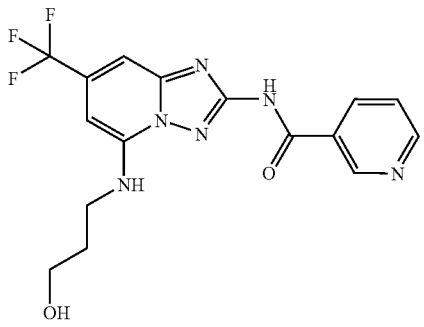
(124)

The title compound was prepared following procedure and work up described for example 118, but starting from N-[5- chloro-7-(trifluoromethyl)[1,2,4]triazolo[1,5-a]pyridin-2-yl]nicotinamide ((B7), 50 mg; 0.14 mmol; 1.0 eq) and 3-amino-1-propanol (56 μL; 0.73 mmol; 5.0 eq), heated at 120° C., to give the title compound as an off-white solid (22 mg, 40%). HPLC, Rt: 2.05 min. (purity 96.2%). LC/MS, M⁺(ESI): 380.8, M⁻(ESI): 378.9.

Example 125

N-[5-[(2-hydroxyethyl)amino]-7-(trifluoromethyl)[1,2,4]triazolo[1,5-a]pyridin-2-yl]nicotinamide (125)

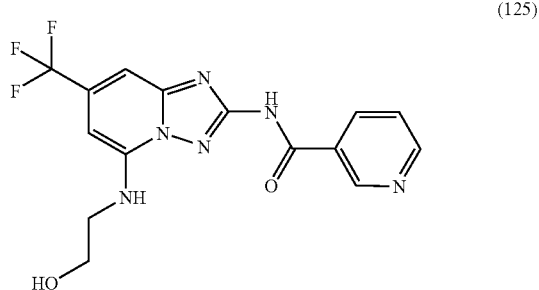

The title compound was prepared following procedure and work up described for example 118, but starting from N-[5-chloro-7-(trifluoromethyl)[1,2,4]triazolo[1,5-a]pyridin-2-yl]nicotinamide ((B7), 50 mg; 0.14 mmol; 1.0 eq) and ethanolamine (44 μL; 0.73 mmol; 5.0 eq), heated at 120° C., to give the title compound as a white solid (15 mg, 28%). HPLC, Rt: 1.91 min. (purity 97.9%). LC/MS, M⁺(ESI): 366.8, M⁻(ESI): 364.9.

Example 126

N-[5-(dimethylamino)-7-(trifluoromethyl)[1,2,4]triazolo[1,5-a]pyridin-2-yl]nicotinamide (126)

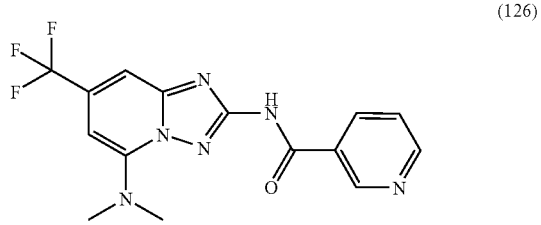

The title compound was prepared following procedure and work up described for example 118, but starting from N-[5-chloro-7-(trifluoromethyl)[1,2,4]triazolo[1,5-a]pyridin-2-yl]nicotinamide ((B7), 50 mg; 0.14 mmol; 1.0 eq) and dimethylamine (43.0 μL; 0.73 mmol; 5.0 eq), heated at 120° C., to give the title compound as a white solid (20 mg, 39%). HPLC, Rt: 2.52 min. (purity 99.7%). LC/MS, M⁺(ESI): 350.8, M⁻(ESI): 348.9.

Example 127

N-[5-(cyclohexylamino)[1,2,4]triazolo[1,5-a]pyridin-2-yl]-2-pyridin-3-ylacetamide Step a) Formation of pyridin-3-ylacetyl chloride

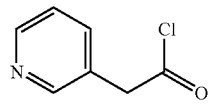

Oxalyl chloride (211 μl; 2.23 mmol; 1.2 eq.) was added to a suspension of 3-pyridineacetic acid (255 mg; 1.86 mmol; 1.0 eq.) in DCM/DMF (5 mL:3 μL) maintained at 0° C. under nitrogen atmosphere. The reaction mixture was then stirred at rt for 1 h. It was then concentrated under reduced pressure. The solid obtained was used as such in amidation reactions.

Step b) Formation of N-[5-(cyclohexylamino)[1,2,4]triazolo[1,5-a]pyridin-2-yl]-2-pyridin-3-ylacetamide (127)

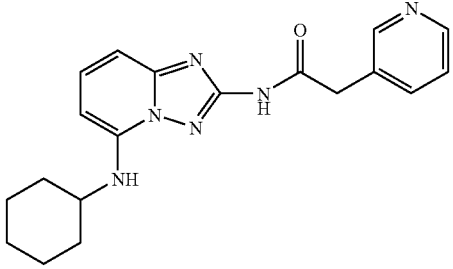

A mixture of pyridin-3-ylacetyl chloride (120.07 mg; 0.77 mmol; 1.50 eq.) and N⁵-cyclohexyl[1,2,4]triazolo[1,5-a]pyridine-2,5-diamine ((A9); 119 mg; 0.51 mmol; 1.0 eq.) in DCM (1 mL) in presence of pyridine (1244; 1.54 mmol; 3 eq.) was heated in a sealed tube at 55° C. for 3 h. Et₂O and Water were then added to the mixture, the precipitate obtained was filtered, washed with water, Et₂O, Acetonitrile and dried under vacuum at 40° C. to give the title compound as an off-white powder (74 mg, 41%). HPLC, Rt: 2.49 min. (purity 98.0%). LC/MS, M⁺(ESI): 350.9, M⁻(ESI): 348.9.

Example 128

N-[5-(cyclohexylamino)[1,2,4]triazolo[1,5-a]pyridin-2-yl]-4-(piperidin-1-ylmethyl)benzamide (128)

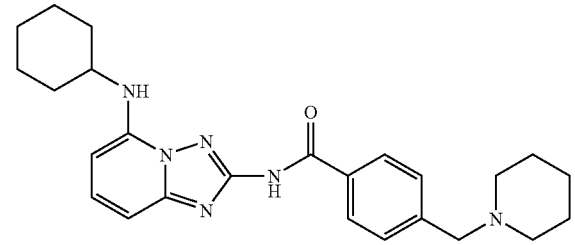

To a reaction vessel containing N-5-cyclohexyl-[1,2,4]triazolo[1,5-a]pyridine-2,5-diamine (69 mg, 0.3 mmol, 1 eq.) and triethylamine (104 μL, 0.75 mmol, 2.5 eq.) in acetonitrile (1 mL) was added 4-piperidin-1-ylmethyl-benzoyl chloride (178 mg, 0.75 mmol, 2.5 eq) as a solution in acetonitrile (2 mL), dropwise. The vessel was capped and stirred at room temperature for approximately 16 hours. The solvent was removed in vacuo and the resulting solid dissolved in methanolic ammonia (4 mL, 7 N) and stirred at room temperature for a further 16 hours. The solvent was removed in vacuo and the residue dissolved in DMSO (1.5 mL) and purified by reverse phase preparatory HPLC to give the title compound as a beige solid (15.3 mg, 12%). Rt: 3.86 min (purity: 97%). LC/MS M⁺(ESI): 433.2, M⁻(ESI) 431.2.

Example 129

N-[5-(cyclohexylamino)[1,2,4]triazolo[1,5-a]pyridin-2-yl]-4-(pyrrolidin-1-ylmethyl)benzamide

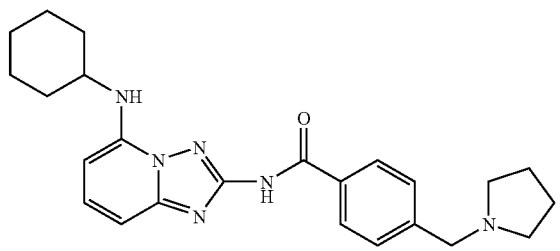

(129)

To a reaction vessel containing N-5-cyclohexyl-[1,2,4]triazolo[1,5-a]pyridine-2,5-diamine (69 mg, 0.3 mmol, 1 eq.) and pyridine (63 μL, 1.2 mmol, 4 eq.) in dichloromethane (1 mL) was added 4-(pyrrolidin-1-ylmethyl)benzoyl chloride hydrochloride (142 mg, 0.6 mmol, 2 eq., prepared from 4-pyrrolidin-1-ylmethyl-benzoic acid, catalytic DMF and oxalyl chloride in DCM) as a solution in dichloromethane (2 mL), dropwise. The vessel was capped and heated to reflux for approximately 16 hours. The reaction mixture was cooled and the solvent removed in vacuo. The residue dissolved in DMSO (1.5 mL) and purified by reverse phase preparatory HPLC to give the title compound as a beige solid (12.4 mg, 10%). HPLC, Rt: 3.50 min (purity: 100%). LC/MS M$^+$(ESI): 419.2, M$^-$(ESI) 417.2.

Example 130

N-[5-(cyclohexylamino)[1,2,4]triazolo[1,5-a]pyridin-2-yl]-4-{[(2-methoxyethyl)(methyl)amino]methyl}benzamide

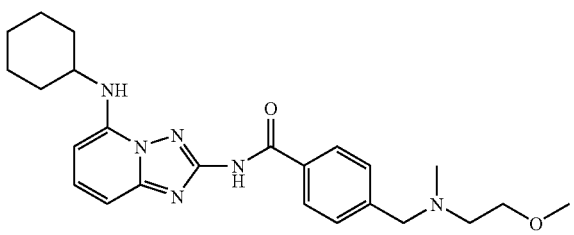

(130)

To a reaction vessel containing 4-chloromethyl-N-(5-cyclohexylamino-[1,2,4]triazolo[1,5-a]pyridin-2-yl)-benzamide ((B8), 90 mg, 0.23 mmol, 1 eq.) and N,N-diisopropylethylamine (0.35 mmol, 61 μL, 1.5 eq.) in dioxane (3 mL) was added N-(2-methoxyethyl)methylamine (0.28 mmol, 25 μL, 1.2 eq.) dropwise. The vessel was capped and the reaction stirred at room temperature for 1 hour and heated to 80° C. for a further 15 hours. The solvent was removed in vacuo and the residue dissolved in DMSO (1.5 mL) and purified by reverse phase preparatory HPLC to give the title compound as a light yellow solid (3.9 mg, 4%). HPLC, Rt: 3.46 min (purity: 93%). LC/MS M$^+$(ESI): 437.2, M$^-$(ESI) 435.2.

Example 131

N-[5-(cyclohexylamino)[1,2,4]triazolo[1,5-a]pyridin-2-yl]-6-methylnicotinamide

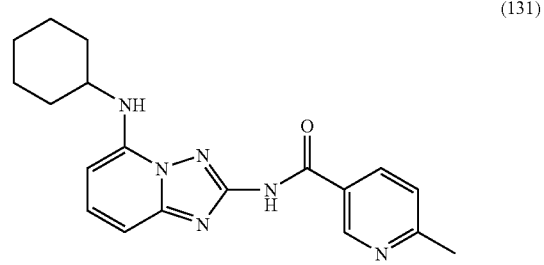

(131)

This was prepared using the same method as that described for N-(5-cyclohexylamino-[1,2,4]triazolo[1,5-a]pyridin-2-yl)-4-(2-oxo-pyrrolidin-1-ylmethyl)-benz amide to give N-(5-cyclohexylamino-[1,2,4]triazolo[1,5-a]pyridin-2-yl)-6-methyl-nicotinamide as a brown/yellow solid (36.5 mg, 35%). HPLC, Rt: 3.21 min (purity: 95%). LC/MS M$^+$(ESI): 351.1, M$^-$(ESI) 349.1.

Example 132

N-[5-(cyclohexylamino)[1,2,4]triazolo[1,5-a]pyridin-2-yl]-6-[(3-hydroxypropyl)amino]nicotinamide

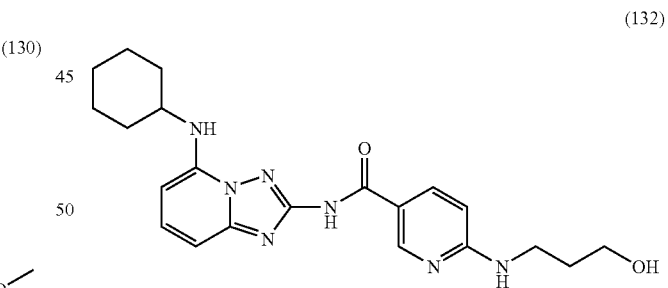

(132)

To a biotage initiator microwave vial (0.2-0.5 mL) containing 6-chloro-N-(5-cyclohexylamino-[1,2,4]triazolo[1,5-a]pyridin-2-yl)-nicotinamide ((B11), 0.27 mmol, 100 mg, 1 eq.), 3-aminopropan-1-ol (0.54 mmol, 0.028 mL, 2 eq.) and N,N-diisopropylethylamine (0.54 mmol, 0.094 mL, 2 eq.) in butanol (2 mL), was capped and heated in a biotage initiator 60 microwave for 30 minutes at 180° C., and a further 10 minutes at 210° C. The solvent was removed in vacuo and the residue dissolved in DMSO (1.5 mL) and purified by reverse phase preparatory HPLC to give the title compound as a white solid (33.4 mg, 30%). HPLC, Rt: 2.37 min (purity: 92%). LC/MS M$^+$(ESI): 410.2, M$^-$(ESI) 408.2.

Example 133

N-[5-(cyclohexylamino)[1,2,4]triazolo[1,5-a]pyridin-2-yl]-6-[(2-furylmethyl)amino]nicotinamide (133)

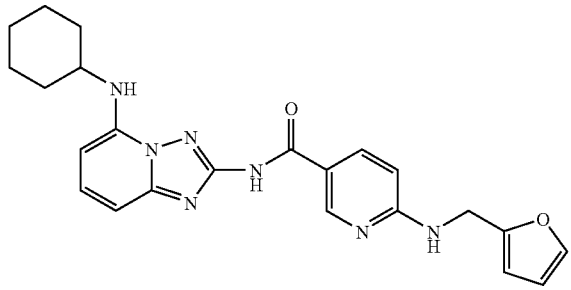

The title compound was prepared following the procedure described for the example 132 but starting from 2-aminomethylfuran as a brown solid (17.5 mg, 15%). HPLC, Rt: 3.50 min (purity: 91%). LC/MS M$^+$(ESI): 432.2, M$^-$(ESI) 430.2.

Example 134

N-[5-(cyclohexylamino)[1,2,4]triazolo[1,5-a]pyridin-2-yl]nicotinamide 1-oxide

Step a) Formation nicotinoyl chloride 1-oxide

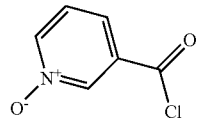

The title compound was prepared following procedure described for example 127, step a), but starting from nicotinic acid N-oxide (255 mg; 1.83 mmol; 1.0 eq.). The solid obtained was used as such in amidation reactions.

Step b) Formation of N-[5-(cyclohexylamino)[1,2,4]triazolo[1,5-a]pyridin-2-yl]nicotinamide 1-oxide (134)

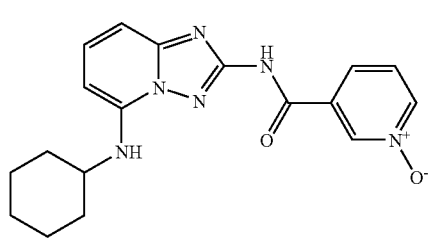

A mixture of N$^5$-cyclohexyl[1,2,4]triazolo[1,5-a]pyridine-2,5-diamine ((A9), 108.00 mg; 0.47 mmol; 1.00 eq.) and nicotinoyl chloride 1-oxide (125 mg; 0.79 mmol; 1.7 eq.) in DCM (1 mL) in the presence of pyridine (113 μL; 1.40 mmol; 3 eq.) was heated in a sealed tube at 55° C. for 3 h. Water was then added and the reaction mixture was extracted with DCM (three times). Combined organic phases were then washed with brine, dried over magnesium sulfate, filtrated and con concentrated. The crude was purified by Mass Directed Auto-Prep. The title compound was obtained after lyophilisation as a white powder (36 mg, 22%). HPLC, Rt: 2.64 min. (purity 99.4%). LC/MS, M$^+$(ESI): 353.0, M$^-$(ESI): 351.0.

Example 135

N-[5-(isopropylamino)-7-(trifluoromethyl)[1,2,4]triazolo[1,5-a]pyridin-2-yl]-2-pyridin-3-ylacetamide trihydrochloride (135)

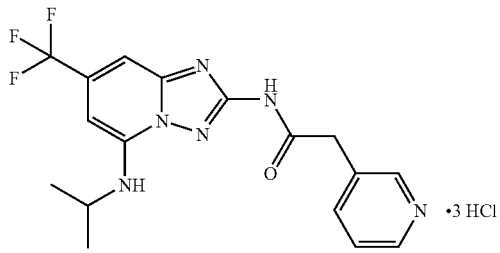

A mixture of N$^5$-isopropyl-7-(trifluoromethyl)[1,2,4]triazolo[1,5-a]pyridine-2,5-diamine ((A17), 73 mg; 0.28 mmol; 1.0 eq.), pyridin-3-ylacetyl chloride (90 mg; 0.58 mmol; 2.05 eq.) and Pyridine (67.98 μL) in DCM (1.00 mL) was heated at 55° C. for 3 h in a sealed tube. Water was added and the reaction mixture was extracted with DCM/MeOH (3:1, three times). Combined organic phases were then washed with brine, dried over magnesium sulfate, filtered and concentrated to give 105 mg of a yellowish powder. This crude was dissolved in MeOH (5 mL) and Et$_2$O/HCl (9 mL of a 1 M solution) was added. The solution was concentrated under reduced pressure. A precipitate was then obtained by addition of DCM/Et$_2$O (1:1). It was filtered and dried under reduced pressure at 40° C. to give the title compound as an off-white solid (73 mg, 2%).

HPLC, Rt: 2.94 min. (purity 95.6%). LC/MS, M$^+$(ESI): 379.0, M$^-$(ESI): 377.0. CHN analysis: [C$_{17}$H$_{17}$N$_6$OF$_3$-3.0 HCl—H$_2$0] Corrected: C, 40.37%; H, 4.38%; N, 16.62%. Found: C, 40.52%; H, 4.28%; N, 16.71%.

Example 136

N-[5-[(1-ethylpropyl)amino]-7-(trifluoromethyl)[1,2,4]triazolo[1,5-a]pyridin-2-yl]nicotinamide (136)

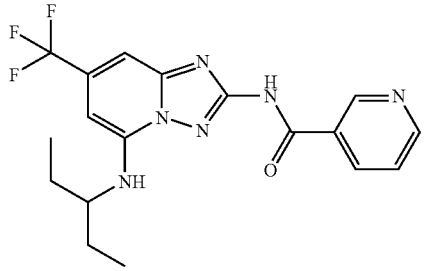

The title compound was prepared following procedure and work up described for example 118, but starting from N-[5-chloro-7-(trifluoromethyl)[1,2,4]triazolo[1,5-a]pyridin-2-yl]nicotinamide ((B7), 50 mg; 0.14 mmol; 1.0 eq) and 3-aminopentane (86 μL; 0.73 mmol; 5.0 eq), heated at 120° C., to give the title compound as a white solid (23 mg, 40%). HPLC, Rt: 3.66 min. (purity 96%). LC/MS, M+(ESI): 392.9, M−(ESI): 391.0.

Example 137

N-[5-(isopropylamino)-7-(trifluoromethyl)[1,2,4]triazolo[1,5-a]pyridin-2-yl]nicotinamide 1-oxide

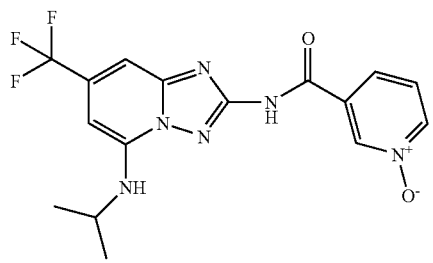

(137)

A mixture of nicotinoyl chloride 1-oxide (180.0 mg; 1.12 mmol; 3.4 eq.) and N⁵-isopropyl-7-(trifluoromethyl)[1,2,4]triazolo[1,5-a]pyridine-2,5-diamine ((A17), 86.0 mg; 0.33 mmol; 1.0 eq.) in DCM (1 mL) in presence of pyridine (80 μL; 1.0 mmol; 3 eq.) was heated in a sealed tube at 55° C. for 3 h. Water was then added to the mixture and the precipitate obtained was filtered, washed with water and DCM and purified by Mass Directed AutoPrep. The title compound was obtained after lyophilisation as a white powder (19 mg, 15%). HPLC, Rt: 3.13 min. (purity 99.4%). LC/MS, M+(ESI): 380.9, M−(ESI): 379.0.

Example 138

N-[5-[(3-hydroxycyclohexyl)amino]-7-(trifluoromethyl)[1,2,4]triazolo[1,5-a]pyridin-2-yl]nicotinamide formic acid

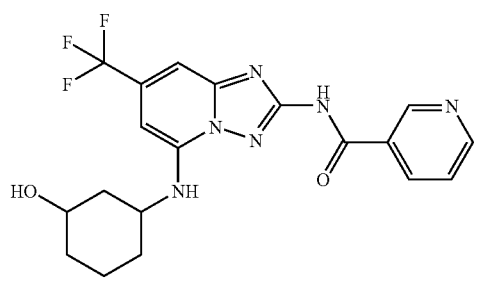

(138)

The title compound was prepared following procedure and work up described for example 118, but starting from N-[5-chloro-7-(trifluoromethyl)[1,2,4]triazolo[1,5-a]pyridin-2-yl]nicotinamide ((B7), 50.0 mg; 0.14 mmol; 1.00 eq) and 3-aminocyclohexanol (Betapharma, 84 mg; 0.73 mmol; 5.00 eq), heated at 120° C. HCl (1.5 M) in MeOH (2 mL) was added to the solid residue and the salt was precipitated by addition of Et₂O, filtered and dried under vacuum, purified by Mass Directed AutoPrep and lyophilized to give the title compound as a mixture of cis:trans isomers as a white solid (11 mg, 18%). HPLC, Rt: 1.72 min. (purity 48.9%, isomer A), 1.87 min. (purity 46.6%, isomer B). LC/MS, M+(ESI): 420.9, M−(ESI): 418.9.

Example 139

N-{7-chloro-5-[(3-hydroxycyclohexyl)amino][1,2,4]triazolo[1,5-a]pyridin-2-yl}nicotinamide formic acid

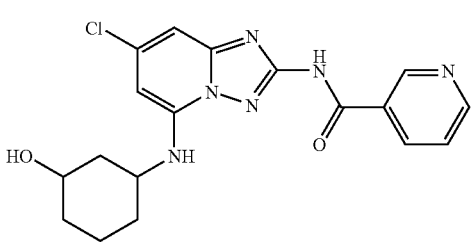

(139)

The title compound was prepared following procedure and work up described for example 118, but starting from N-(5,7-dichloro[1,2,4]triazolo[1,5-a]pyridin-2-yl)nicotinamide ((B10), 100 mg; 0.32 mmol; 1.0 eq) and 3-aminocyclohexanol (Betapharma, 187 mg; 1.62 mmol; 5.0 eq), heated at 120° C., filtered and dried under vacuum, purified by Mass Directed AutoPrep and lyophilized to give the title compound as a mixture of cis:trans isomers as a beige powder (9 mg, 7%). HPLC, Rt: 2.15 min. (purity 57.4%, isomer A), 2.28 min. (purity 34.7%, isomer B). LC/MS, M+(ESI): 386.9, M−(ESI): 384.9.

Example 140

N-[5-(cyclopropylamino)-7-(trifluoromethyl)[1,2,4]triazolo[1,5-a]pyridin-2-yl]-4-[(dimethylamino)methyl]benzamide

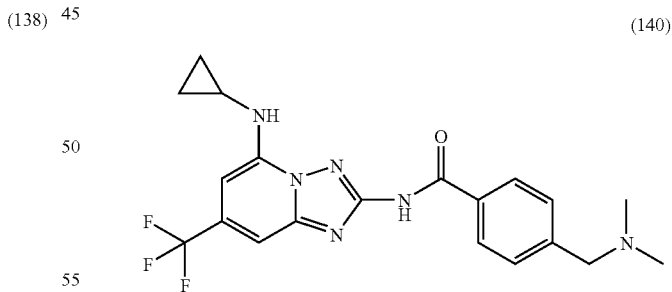

(140)

To a reaction vessel containing N⁵-cyclopropyl-7-(trifluoromethyl)[1,2,4]triazolo[1,5-a]pyridine-2,5-diamine ((A18), 77 mg, 0.3 mmol, 1 eq.) and pyridine (0.063 mL, 1.2 mmol, 4 eq.) in dichloromethane (1 mL) was added 4-dimethylaminomethyl-benzoyl chloride (118 mg, 0.6 mmol, 2 eq.) as a solution in dichloromethane (2 mL), dropwise. The vessel was capped and heated to reflux for approximately 16 hours. The reaction mixture was cooled and the solvent removed in vacuo. The residue dissolved in DMSO (1.5 mL) and purified by reverse phase preparatory HPLC to give the title compound as a white solid (65.1 mg, 52%). HPLC, Rt: 2.59 min (purity: 100%). LC/MS M+(ESI): 419.2, M−(ESI) 417.2.

Example 141

N-[5-(cyclopropylamino)-7-(trifluoromethyl)[1,2,4]triazolo[1,5-a]pyridin-2-yl]-4-[(2-oxopyrrolidin-1-yl)methyl]benzamide (141)

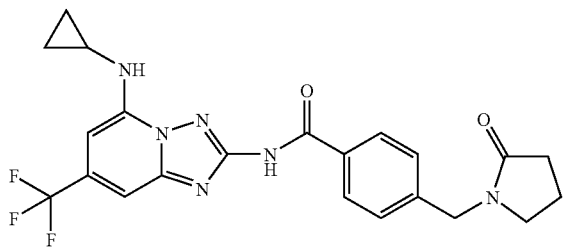

The title compound was prepared following procedure and work up described for example 140 but starting from 4-[(2-oxopyrrolidin-1-yl)methyl]benzoyl chloride (prepared in DCM from 4-[(2-oxopyrrolidin-1-yl)methyl]benzoic acid (Enamine), oxalyl chloride and catalytic amount of DMF following the procedure described for example 127, step a)). The title compound was obtained as an off-white solid (73.6 mg, 27%). HPLC, Rt: 2.43 min (purity: 94%). LC/MS M+(ESI): 459.2, M−(ESI) 457.2.

Example 142

N-[5-(cyclopropylamino)-7-(trifluoromethyl)[1,2,4]triazolo[1,5-a]pyridin-2-yl]-6-pyrrolidin-1-ylnicotinamide (142)

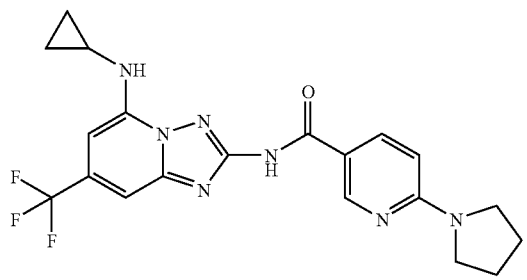

The title compound was prepared following procedure and work up described for example 140 but starting from 6-pyrrolidin-1-ylpyridine-3-carbonyl chloride (prepared in DCM from 6-(1-pyrrolidinyl)nicotinic acid (ABCR), oxalyl chloride and catalytic amount of DMF following the procedure described for example 127, step a)). The title compound was obtained as a beige solid (18.5 mg, 14%). HPLC, Rt: 2.70 min (purity: 97%). LC/MS M+(ESI): 432.2, M−(ESI) 430.2.

Example 143

N-[5-(cyclopropylamino)-7-(trifluoromethyl)[1,2,4]triazolo[1,5-a]pyridin-2-yl]-6-methylnicotinamide (143)

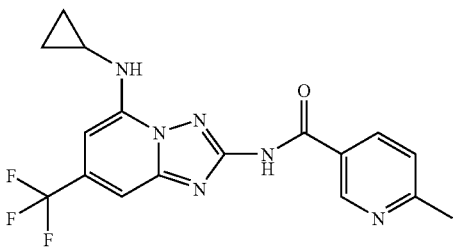

The title compound was prepared following procedure and work up described for example 140 but starting from 6-methylpyridine-3-carbonyl chloride (prepared in DCM from 6-methylnicotinic acid, oxalyl chloride and catalytic amount of DMF following the procedure described for example 127, step a)). The title compound was obtained as a cream solid (14.6 mg, 13%). HPLC, Rt: 2.35 min (purity: 97%). LC/MS M+(ESI): 377.2, M−(ESI) 375.2.

Example 144

N-[6-(4-hydroxy-3-methoxyphenyl)[1,2,4]triazolo[1,5-a]pyridin-2-yl]-4-(piperidin-1-ylmethyl)benzamide (144)

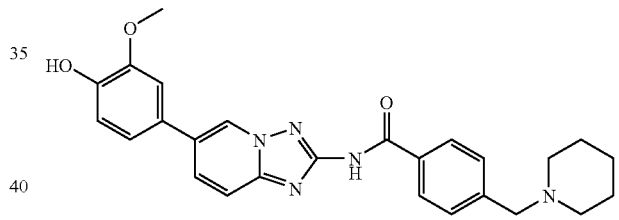

Step a) Formation of 6-{3-(methyloxy)-4-[(phenylmethyl)oxy]phenyl}[1,2,4]triazolo[1,5-a]pyridin-2-amine

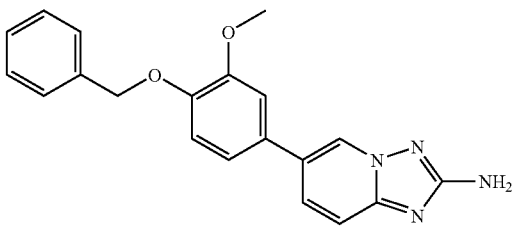

To a reaction vessel containing 6-bromo[1,2,4]triazolo[1,5-a]pyridin-2-amine ((A5), 3.44 g, 16.1 mmol, 1 eq.), 4-benzyloxy-3-methoxy boronic acid (5.0 g, 19.3 mmol, 1.2 eq., Synthonix) and cesium fluoride (7.34 g, 48.3 mmol, 3 eq.) in dimethylformamide (60 mL) and water (24 mL) was added bis-triphenylphosphine palladium dichloride (0.3 g, 0.4 mmol, 3%). The vessel was purged with nitrogen, capped and heated at 80° C. for approximately 18 hours. After this time, the crude mixture was filtered through celite washing the celite with ethyl acetate and water. The resulting filtrate was extracted with ethyl acetate (3×150 mL) and the combined organic layers dried (MgSO₄) and concentrated in vacuo. The resulting residue was purified by flash column chromatography (ethyl acetate:petroleum ether; 1:1) to give the title compound as a brown solid (4.82 g, 86%). HPLC, Rt: 2.55 min (purity 96%). LC/MS M⁺(ESI): 347, M⁻(ESI) 345.

Step b) Formation of N-(6-{3-(methyloxy)-4-[(phenylmethyl)oxy]phenyl}[1,2,4]triazolo[1,5-a]pyridin-2-yl)-4-(piperidin-1-ylmethyl)benzamide

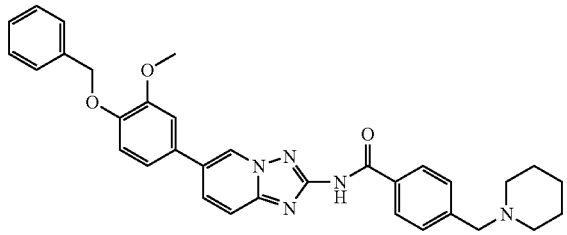

To a reaction vessel containing the 6-{3-(methyloxy)-4-[(phenylmethyl)oxy]phenyl}[1,2,4]triazolo[1,5-a]pyridin-2-amine (104 mg, 0.3 mmol, 1 equivalent) and pyridine (0.063 mL, 1.2 mmol, 4 eq.) in dichloromethane (1 mL) was added 4-piperidin-1-ylmethyl-benzoyl chloride (142 mg, 0.6 mmol, 2 eq.) as a solution in dichloromethane (2 mL), dropwise. The vessel was capped and heated to reflux for approximately 16 hours. The reaction mixture was cooled and the solvent removed in vacuo. The residue dissolved in DMSO (1.5 mL) and purified by reverse phase preparatory HPLC to give N-[6-(4-benzyloxy-3-methoxy-phenyl)-[1,2,4]triazolo[1,5-a]pyridin-2-yl]-4-piperidin-1-ylmethyl-benzamide as a white solid (14.9 mg, 9%).

Step c) Formation of N-[6-(4-hydroxy-3-methoxyphenyl)[1,2,4]triazolo[1,5-a]pyridin-2-yl]-4-(piperidin-1-ylmethyl)benzamide N-(6-{3-(methyloxy)-4-[(phenylmethyl)oxy]phenyl}[1,2,4]triazolo[1,5-a]pyridin-2-yl)-4-(piperidin-1-ylmethyl)benzamide (14.9 mg, 0.027 mmol) was treated with trifluoroacetic acid (2 mL) and the reaction mixture was stirred for 1 hour at 75° C. The reaction mixture was cooled and the solvent removed in vacuo. The residue dissolved in DMSO (1.5 mL) and purified by reverse phase preparatory HPLC to give the title compound as a white solid (1.4 mg, 11%). HPLC, Rt: 2.23 min (purity: 99%). LC/MS M⁺(ESI): 458.2, M⁻(ESI) 456.2.

Example 145

N-[6-(4-hydroxy-3-methoxyphenyl)[1,2,4]triazolo[1,5-a]pyridin-2-yl]-6-methylnicotinamide (145)

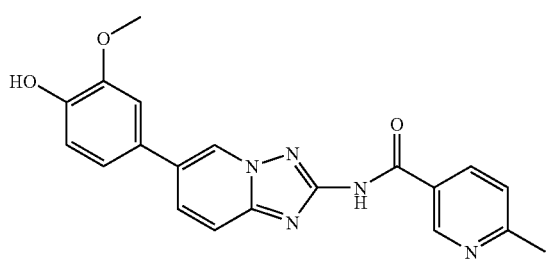

The title compound was prepared following procedure and work up described for example 145 but starting from 6-methylpyridine-3-carbonyl chloride (prepared in DCM from 6-methylnicotinic acid, oxalyl chloride and catalytic amount of DMF following the procedure described for example 127, step a)). The title compound was obtained as a cream solid (5.2 mg, 24%). HPLC, Rt: 1.52 min (purity: 98%). LC/MS M⁺(ESI): 376.1, M⁻(ESI) 374.1.

Example 146

N-[6-(4-hydroxy-3-methoxyphenyl)[1,2,4]triazolo[1,5-a]pyridin-2-yl]-4-[(2-oxopyrrolidin-1-yl)methyl]benzamide (146)

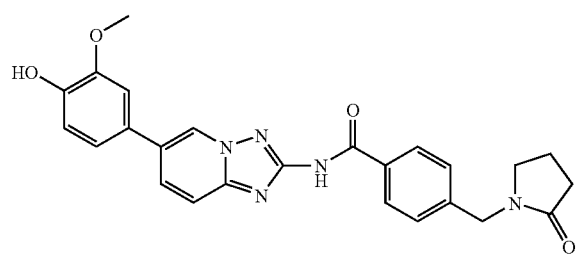

The title compound was prepared following procedure and work up described for example 144 but starting from 4-[(2-oxopyrrolidin-1-yl)methyl]benzoyl chloride (prepared in DCM from 4-[(2-oxopyrrolidin-1-yl)methyl]benzoic acid (Enamine), oxalyl chloride and catalytic amount of DMF following the procedure described for example 127, step a)). The title compound was obtained as a white solid (4.1 mg, 28%). HPLC, Rt: 1.68 min (purity: 98%). LC/MS M⁺(ESI): 458.2, M⁻(ESI) 456.2.

Example 147

4-[(dimethylamino)methyl]-N-[6-(4-hydroxy-3-methoxyphenyl)[1,2,4]triazolo[1,5-a]pyridin-2-yl]benzamide (147)

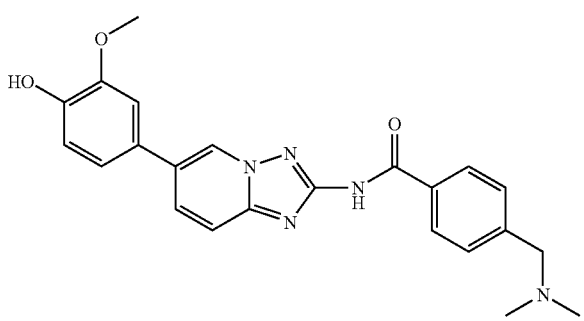

The title compound was prepared following procedure and work up described for example 144 but starting from 4-dimethylaminomethyl-benzoyl chloride (prepared in DCM from 4-[(dimethylamino)methyl]benzoic acid (Enamine), oxalyl chloride and catalytic amount of DMF following the procedure described for example 127, step a)). The title compound was obtained as a white solid (13.7 mg, 45%). HPLC, Rt: 1.81 min (purity: 97%). LC/MS M⁺(ESI): 418.2, M⁻(ESI) 416.2

The following additional compounds (Examples 148-182) of Table 1 have been prepared following the above protocols.

TABLE 1

Examples of additional Triazolopyridine compounds

| Example | Structure | Name | HPLC purity (%) | Rt (min) | M + H (ESI) | Appearance |
|---|---|---|---|---|---|---|
| 148 | 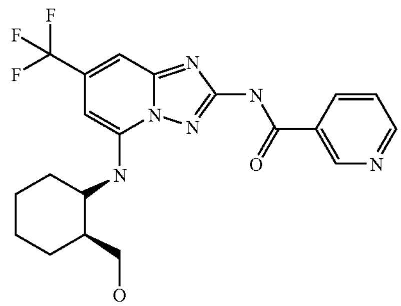 | N-[5-{[(1R,2S)-2-(hydroxymethyl)cyclohexyl]amino}-7-(trifluoromethyl)[1,2,4]triazolo[1,5-a]pyridin-2-yl]nicotinamide hydrochloride | 91.9 | 3.5 | 435 | white powder |
| 149 | 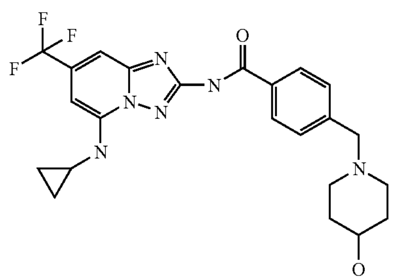 | N-[5-(cyclopropylamino)-7-(trifluoromethyl)[1,2,4]triazolo[1,5-a]pyridin-2-yl]-4-[(4-hydroxypiperidin-1-yl)methyl]benzamide | 93.6 | 2.4 | 475 | pale yellow solid |
| 150 | 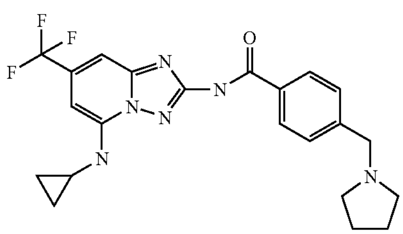 | N-[5-(cyclopropylamino)-7-(trifluoromethyl)[1,2,4]triazolo[1,5-a]pyridin-2-yl]-4-(pyrrolidin-1-ylmethyl)benzamide | 90.2 | 2.44 | 445 | yellow solid |
| 151 | 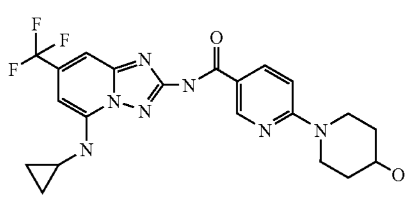 | N-[5-(cyclopropylamino)-7-(trifluoromethyl)[1,2,4]triazolo[1,5-a]pyridin-2-yl]-6-(4-hydroxypiperidin-1-yl)nicotinamide | 99 | 2.85 | 462 | off-white solid |
| 152 | 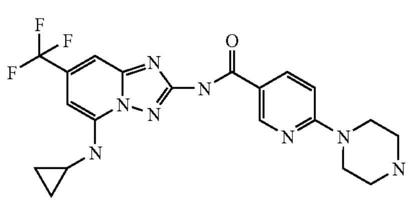 | N-[5-(cyclopropylamino)-7-(trifluoromethyl)[1,2,4]triazolo[1,5-a]pyridin-2-yl]-6-piperazin-1-ylnicotinamide | 90.1 | 2.4 | 447 | yellow solid |
| 153 | 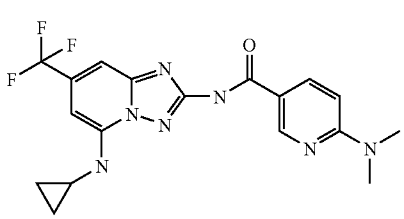 | N-[5-(cyclopropylamino)-7-(trifluoromethyl)[1,2,4]triazolo[1,5-a]pyridin-2-yl]-6-(dimethylamino)nicotinamide | 95.9 | 2.8 | 406 | pale yellow solid |

TABLE 1-continued

Examples of additional Triazolopyridine compounds

| Example | Structure | Name | HPLC purity (%) | Rt (min) | M + H (ESI) | Appearance |
|---|---|---|---|---|---|---|
| 154 | 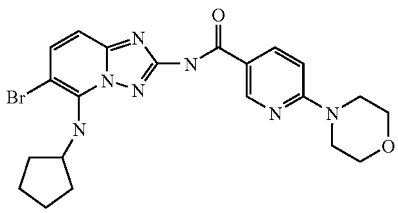 | N-[6-bromo-5-(cyclopentylamino)[1,2,4]triazol[1,5-a]pyridin-2-yl]-6-morpholin-4-ylnicotinamide | 93 | 3.6 | 486 | white solid |
| 155 | 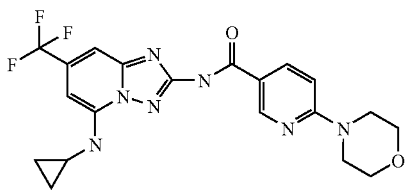 | N-[5-(cyclopropylamino)-7-(trifluoromethyl)[1,2,4]triazolo[1,5-a]pyridin-2-yl]-6-morpholin-4-ylnicotinamide | 98 | 3.41 | 448 | white solid |
| 156 | 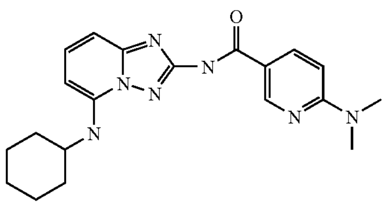 | N-[5-(cyclohexylamino)[1,2,4]triazolo[1,5-a]pyridin-2-yl]-6-(dimethylamino)nicotinamide | 96.4 | 2.65 | 380 | off-white solid |
| 157 | 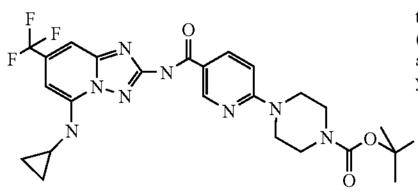 | tert-butyl 4-[5-({[5-(cyclopropylamino)-7-(trifluoromethyl)[1,2,4]triazolo[1,5-a]pyridin-2-yl]amino}carbonyl)pyridin-2-yl]piperazine-1-carboxylate | 98.8 | 4 | 547 | brown solid |
| 158 | 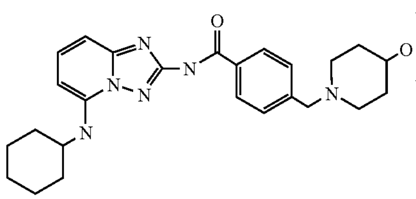 | N-[5-(cyclohexylamino)[1,2,4]triazolo[1,5-a]pyridin-2-yl]-4-[(4-hydroxypiperidin-1-yl)methyl]benzamide | 93.4 | 2.35 | 449 | yellow oil |
| 159 | 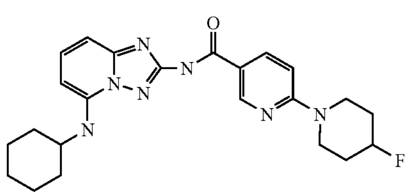 | N-[5-(cyclohexylamino)[1,2,4]triazolo[1,5-a]pyridin-2-yl]-6-(4-fluoropiperidin-1-yl)nicotinamide | 94.7 | 3.47 | 438 | white solid |
| 160 | 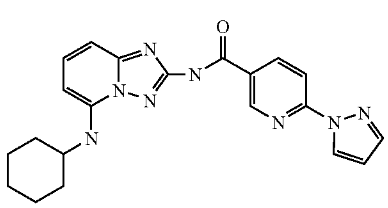 | N-[5-(cyclohexylamino)[1,2,4]triazolo[1,5-a]pyridin-2-yl]-6-(1H-pyrazolo-1-yl)nicotinamide | 95.7 | 3.68 | 403 | brown solid |

TABLE 1-continued

Examples of additional Triazolopyridine compounds

| Example | Structure | Name | HPLC purity (%) | Rt (min) | M + H (ESI) | Appearance |
|---|---|---|---|---|---|---|
| 161 | 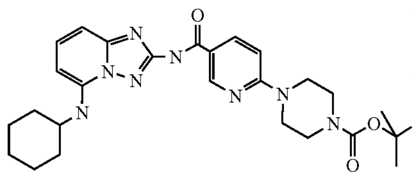 | tert-butyl 4-[5-({[5-(cyclohexylamino)[1,2,4]triazolo[1,5-a]pyridin-2-yl]amino}carbonyl)pyridin-2-yl]piperazine-1-carboxylate | 95.4 | 3.85 | 521 | off-white solid |
| 162 | 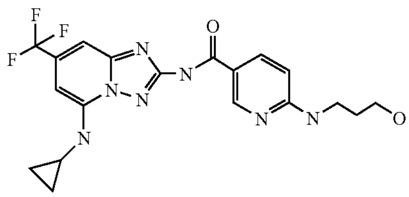 | N-[5-(cyclopropylamino)-7-(trifluoromethyl)[1,2,4]triazolo[1,5-a]pyridin-2-yl]-6-[(3-hydroxypropyl)amino]nicotinamide | 98.5 | 2.47 | 436 | white solid |
| 163 | 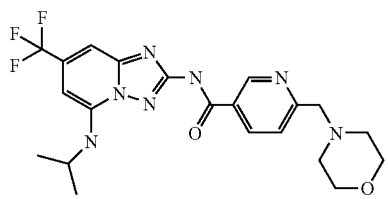 | N-[5-(isopropylamino)-7-(trifluoromethyl)[1,2,4]triazolo[1,5-a]pyridin-2-yl]-6-(morpholin-4-ylmethyl)nicotinamide | 97.7 | 3.00 | 463 | off-white solid |
| 164 | 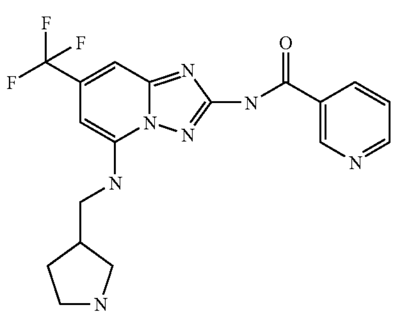 | N-[5-[(pyrrolidin-3-ylmethyl)amino]-7-(trifluoromethyl)[1,2,4]triazolo[1,5-a]pyridin-2-yl]nicotinamide | 80.8 | 2.26 | 406 | yellow solid |
| 165 | 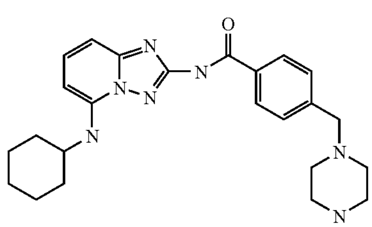 | N-[5-(cyclohexylamino)[1,2,4]triazolo[1,5-a]pyridin-2-yl]-4-(piperazin-1-ylmethyl)benzamide | 90.8 | 2.17 | 434 | yellow oil |
| 166 | 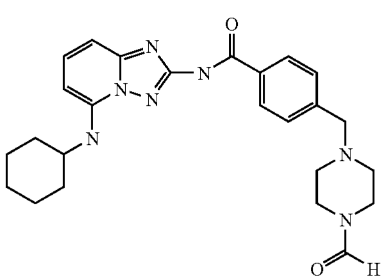 | N-[5-(cyclohexylamino)[1,2,4]triazolo[1,5-a]pyridin-2-yl]-4-[(4-formylpiperazin-1-yl)methyl]benzamide | 86.3 | 2.24 | 462 | yellow oil |

TABLE 1-continued

Examples of additional Triazolopyridine compounds

| Example | Structure | Name | HPLC purity (%) | Rt (min) | M + H (ESI) | Appearance |
|---|---|---|---|---|---|---|
| 167 | 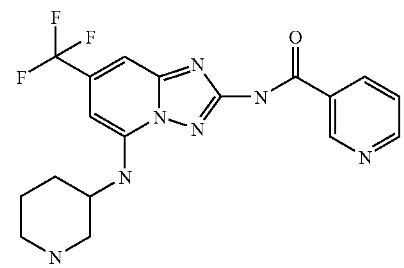 | N-[5-(piperidin-3-ylamino)-7-(trifluoromethyl)[1,2,4]triazolo[1,5-a]pyridin-2-yl]nicotinamide | 92.2 | 2.37 | 406 | yellow oil |
| 168 | 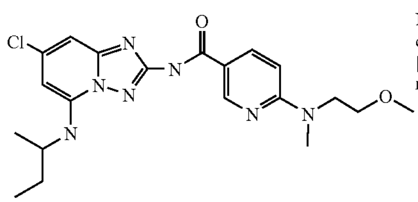 | N-[5-(sec-butylamino)-7-chloro[1,2,4]triazolo[1,5-a]pyridin-2-yl]-6-[(2-methoxyethyl)methyl)amino]nicotinamide | 96.6 | 3.16 | 432 | white solid |
| 169 | 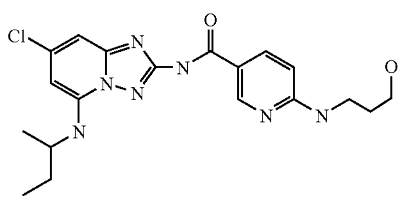 | N-[5-(sec-butylamino)-7-chloro[1,2,4]triazolo[1,5-a]pyridin-2-yl]-6-[(3-hydroxypropyl)amino]nicotinamide | 98.7 | 2.49 | 418 | white solid |
| 170 | 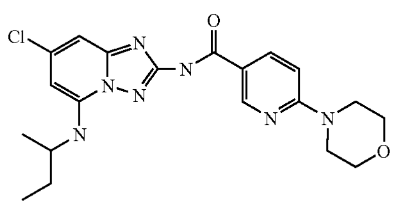 | N-[5-(sec-butylamino)-7-chloro[1,2,4]triazolo[1,5-a]pyridin-2-yl]-6-morpholin-4-ylnicotinamide | 98.2 | 3.5 | 430 | white solid |
| 171 | 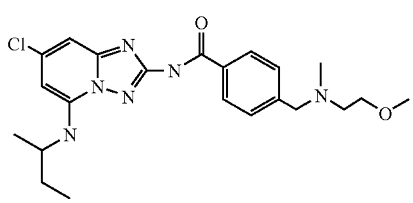 | N-[5-(sec-butylamino)-7-chloro[1,2,4]triazolo[1,5-a]pyridin-2-yl]-4-{[(2-methoxyethyl)(methyl)amino]methyl}benzamide | 96.1 | 2.27 | 446 | yellow solid |
| 172 | 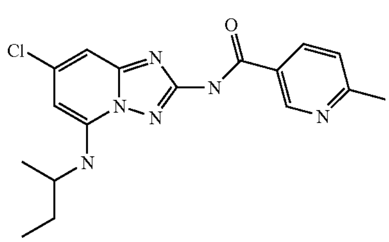 | N-[5-(sec-butylamino)-7-chloro[1,2,4]triazolo[1,5-a]pyridin-2-yl]-6-methylnicotinamide | 93 | 3.14 | 359 | pale brown solid |

TABLE 1-continued

Examples of additional Triazolopyridine compounds

| Example | Structure | Name | HPLC purity (%) | Rt (min) | M + H (ESI) | Appearance |
|---|---|---|---|---|---|---|
| 173 | 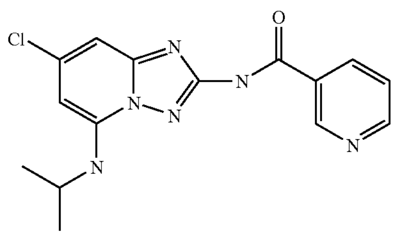 | N-[7-chloro-5-(isopropylamino)[1,2,4]triazolo[1,5-a]pyridin-2-yl]nicotinamide | 98.1 | 2.99 | 331 | white solid |
| 174 | 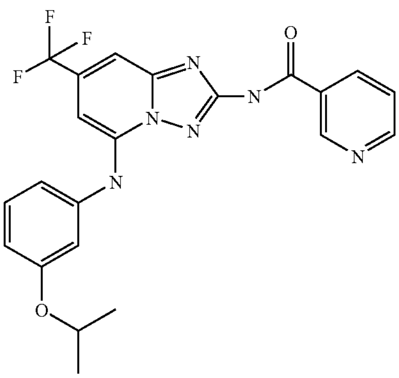 | N-[5-[(3-isopropoxyphenyl)amino]-7-(trifluoromethyl)[1,2,4]triazolo[1,5-a]pyridin-2-yl]nicotinamide | 96 | 3.86 | 457 | white solid |
| 175 | 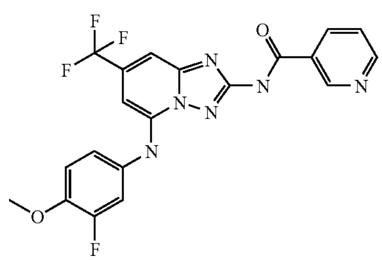 | N-[5-[(3-fluoro-4-methoxyphenyl)amino]-7-(trifluoromethyl)[1,2,4]triazolo[1,5-a]pyridin-2-yl]nicotinamide | 98.4 | 3.43 | 447 | yellow solid |
| 176 | 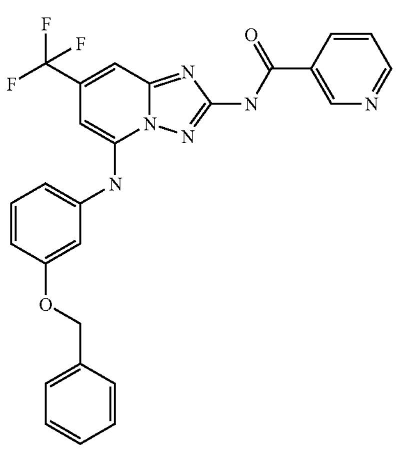 | N-[5-{[3-(benzyloxy)phenyl]amino}-7-(trifluoromethyl)[1,2,4]triazolo[1,5-a]pyridin-2-yl]nicotinamide | 98.3 | 4.02 | 505 | yellow solid |
| 177 | 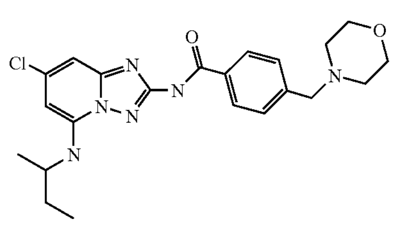 | N-[5-(sec-butylamino)-7-chloro[1,2,4]triazolo[1,5-a]pyridin-2-yl]-4-(morpholin-4-ylmethyl)benzamide | 93 | 2.46 | 443 | white solid |

TABLE 1-continued

Examples of additional Triazolopyridine compounds

| Example | Structure | Name | HPLC purity (%) | Rt (min) | M + H (ESI) | Appearance |
|---|---|---|---|---|---|---|
| 178 | 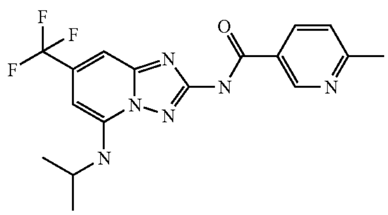 | N-[5-(isopropylamino)-7-(trifluoromethyl)[1,2,4]triazolo[1,5-a]pyridin-2-yl]-6-methylnicotinamide | 92 | 3.11 | 379 | pale brown solid |
| 179 | 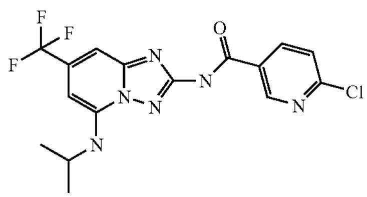 | 6-chloro-N-[5-(isopropylamino)-7-(trifluoromethyl)[1,2,4]triazolo[1,5-a]pyridin-2-yl]nicotinamide | 99.2 | 3.69 | 399 | white solid |
| 180 | 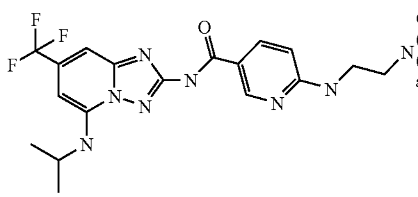 | 6-[(2-aminoethyl)amino]-N-[5-(isopropylamino)-7-(trifluoromethyl)[1,2,4]triazolo[1,5-a]pyridin-2-yl]nicotinamide | 96.3 | 2.37 | 423 | yellow solid |
| 181 | 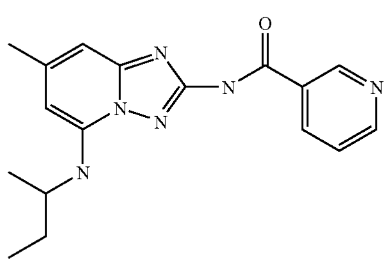 | N-[5-(sec-butylamino)-7-methyl[1,2,4]triazolo[1,5-a]pyridin-2-yl]nicotinamide | 84.5 | 2.47 | 325 | off-white powder |
| 182 | 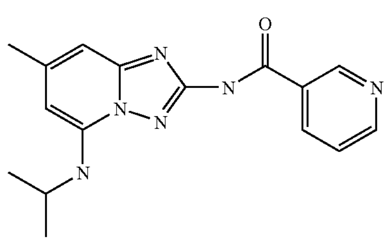 | N-[5-(isopropylamino)-7-methyl[1,2,4]triazolo[1,5-a]pyridin-2-yl]nicotinamide | 67 | 2.15 | 311 | off-white powder |

Assays

Example 183

Enzyme Inhibition Assays (In Vitro ASK1 Assays)

Assays were performed in a 384 well plate (Corning, #3654) format, using the human recombinant ASK1 as an enzyme and MBP (myelin basic protein, Upstate/Millipore, #13-104) with ATP as substrates. Assay read out was the measurement of the amount of ATP remaining after stopping the reaction, using a luciferase-based kit from Cambrex.

Materials and Methods

Compounds to be tested were dissolved in 100% DMSO at a concentration of 10 mM. Subsequent dilutions were performed in 100% DMSO using a Biomek FX Workstation. 5 µL of diluted compound or vehicle (6% DMSO) was distributed to a 384 well plate. 5 µL of substrates (ATP 7.5 µM, MBP 450 ng/µL) diluted in ASK1 buffer (20 mM Tris HCl pH 7.4, 0.001% Brij35, 0.01% BSA, 5 mM MgCl$_2$, 1 mM DL-Dithiothreitol) were added, followed by 5 µL at of human recombinant ASK1 enzyme (22.5 ng/mL) diluted in ASK1 buffer in order to start the reaction. The reaction ran for 180 minutes at 30° C. before the addition of 5 µL of stop solution (Cambrex,

LT23-231). 10 μL of Pklight ATP detection reagent (Cambrex #LT23-233) were added. After 120 min of incubation, luminescence was measured on a Perkin-Elmer Victor 2 spectrofluorimeter. The percentage of inhibition relative to the fluorescence observed in the presence of solvent (1% DMSO) alone was determined. The $IC_{50}$ values for inhibition were determined in triplicates on at least 2 separate occasions.

The results are expressed in terms of $IC_{50}$ (the concentration of compound required to give a 50% decrease in enzyme activity) and are presented in Table 2 below for compounds of Formula (I).

TABLE 2

$IC_{50}$ on ASK1 in nM

| Example No. | $IC_{50}$ (nM) |
| --- | --- |
| 2 | 700 ± 200 |
| 3 | 8000 ± 400 |
| 5 | 17000 ± 5000 |
| 7 | 7000 ± 1000 |
| 10 | 16000 ± 4000 |
| 12 | 14800 ± 200 |
| 30 | 1100 ± 500 |
| 44 | 6900 ± 50 |
| 45 | 3380 |
| 50 | 8000 ± 1000 |
| 52 | 1700 ± 200 |
| 56 | 990 ± 40 |
| 61 | 180 ± 20 |
| 63 | 9860 |
| 66 | 260 ± 10 |
| 72 | 4080 |
| 74 | 120 ± 10 |
| 81 | 1660 ± 50 |
| 83 | 1900 ± 200 |
| 86 | 110 ± 50 |
| 87 | 5960 |
| 89 | 460 ± 50 |
| 90 | 700 ± 100 |
| 94 | 5900 |
| 96 | 990 ± 110 |
| 99 | 42 ± 7 |
| 100 | 56 ± 8 |
| 115 | 519 ± 113 |
| 118 | 87 ± 6 |
| 120 | 67 ± 12 |
| 124 | 197 ± 6 |
| 130 | 531 ± 18 |
| 132 | 91 ± 26 |
| 140 | 1140 |
| 144 | 2000 |
| 146 | 138 ± 30 |
| 147 | 5500 |
| 169 | 119 ± 29 |

Example 184

Lipopolysaccharide (LPS)-Induced TNFα Release Assay in Mice

Rationale

The administration of LPS induces the release of TNFα from white blood cells (monocytes, macrophages, Kupffer cells, etc) and endothelial cells into the blood. This is a model for cytokine release that occurs during inflammation. Free radical scavengers (Edaravone, N-Acetylcystein, etc) were shown to reduce LPS-induced TNFα release in mice. ASK1 mediates free radical pathways. Based on this mechanism, the blockade of ASK1 by specific inhibitors should reduce LPS-induced TNFα release in mice.

Method

Female C3H mice (Elevage Janvier) (8 week old), received E. Coli's LPS (O111:B4, Sigma, 0.3 mg/kg, ip) after the administration of the test articles. Ninety min later, the animals were sacrificed and the blood was sampled. Plasma levels of TNFα were determined in serum using an ELISA kit (R&D). LPS was solubilized in sterile saline.

Protocol

The test articles were suspended in 0.5% CMC/0.25% Tween 20 and administered 15 min prior the challenge of LPS by oral route at the doses of 3 to 30 mg/kg. Control animals received the vehicle. In time course experiments, the test articles were administered 15 min to 4 hrs prior the challenge of LPS. Dexamethasone (0.1 mg/kg, po) was used as reference.

Summary of the Experimental Design

The animals were divided into 5 groups (6 mice each group):

Group 1: (control LPS) received 0.5% CMC/0.25% tween-20 and injection of LPS;

Group 2: Experimental group (Compound of the invention Dose 1 is 3 mg/kg) received a compound of the invention and injection of LPS;

Group 3: Experimental group (Compound of the invention Dose 2 is 10 mg/kg) received a compound of the invention and injection of LPS;

Group 4: Experimental group (Compound of the invention Dose 3 is 30 mg/kg) received a compound of the invention and injection of LPS;

Group 5: Reference group received the reference compound (dexamethasone) and injection of LPS.

Calculation

Inhibition of TNFα release was calculated as follows:

% inhibition=100*(1−(TNFαX/TNFα1))

Where TNFα 1=TNFα concentration in group 1 (pg/ml), TNFα X=TNFα concentration in group X (pg/ml).

TABLE 3

Percentage of inhibition of LPS-induced TNFα release in mice by compounds of the invention:

| Example | Dose (mg/kg) | Route | % inhibition |
| --- | --- | --- | --- |
| Example 2 | 30 | po | 49 ± 8 |
| Example 30 | 30 | po | 43 ± 3 |

Formulations

Preparation of a Pharmaceutical Formulation

Formulation 1—Tablets

A compound of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of Formula (I) is dissolved in a buffered sterile saline injectable aqueous medium to a concentration of approximately 5 mg/ml.

The invention claimed is:
1. A triazolopyridine compound of formula I-1:

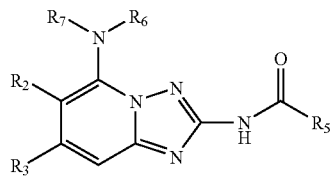

Formula I-1 wherein:
$R_2$ is selected from:
a) hydrogen; or
b) halogen;
$R_3$ is selected from:
a) hydrogen;
b) halogen; or
c) $C_1$-$C_6$-alkyl that is unsubstituted or is substituted with at least one fluoro;
$R_5$ is selected from:
a) $C_1$-$C_6$-alkyl that is unsubstituted or is substituted with at least one of the following groups:
  i) alkoxycarbonyl,
  ii) $C_1$-$C_6$-alkoxy,
  iii) —NC(O)R' wherein R' is an aryl that is unsubstituted or is substituted with $C_1$-$C_6$-alkyl, or
  iv) benzyloxy;
b) aryl-$C_1$-$C_6$-alkyl;
c) 5 or 6-membered heteroaryl-$C_1$-$C_6$-alkyl having a heteroatom selected from N, S or O that is unsubstituted or is substituted with $C_1$-$C_6$-alkyl, halogen or $C_1$-$C_6$-alkoxy;
d) $C_3$-$C_6$-cycloalkyl that is unsubstituted or is substituted with phenyl;
e) 3 to 8-membered heterocycloalkyl having a heteroatom selected from N, S or O that is substituted with an acyl group;
f) aryl that is unsubstituted or is substituted with at least one of the following groups:
  i) $C_1$-$C_6$-alkyl,
  ii) halogen,
  iii) $C_1$-$C_6$-alkoxy,
  iv) perfluoro-$C_1$-$C_6$-alkyl,
  v) at least one $C_1$-$C_6$-alkoxy that is unsubstituted or is substituted with $C_1$-$C_6$-alkoxy carbonyl,
  vi) phenyl,
  vii) $C_1$-$C_6$-alkyl sulfonyl,
  viii) —NHC(O)$C_1$-$C_6$-alkyl,
  ix) amino-$C_1$-$C_6$-alkyl wherein amino is selected from —NH$_2$, —NHC$_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached and wherein the heterocycloalkyl is unsubstituted or is substituted with $C_1$-$C_6$-alkyl or with hydroxy,
  x) —N($C_1$-$C_6$-alkyl) ($C_1$-$C_6$-alkoxy-$C_1$-$C_6$-alkyl),
  xi) 5 to 6-membered heterocycloalkyl-$C_1$-$C_6$-alkyl having a heteroatom selected from N and O, or
  xii) amido-$C_1$-$C_6$-alkyl;
g) 5 to 10-membered heteroaryl having at least one heteroatom selected from N, O or S optionally substituted with halogen; or
h) pyridinyl that is unsubstituted or is substituted with at least one of the following groups:
  i) halogen,
  ii) $C_1$-$C_6$-alkyl,
  iii) amino-$C_1$-$C_6$-alkyl wherein amino is selected from —NH$_2$, —NHC$_1$-$C_6$-alkyl or —N($C_1$-$C_6$-alkyl)$_2$, wherein the two substituents $C_1$-$C_6$-alkyl can be the same or different, and wherein the two substituents may form a 3 to 8-membered heterocycloalkyl with the N to which they are attached and wherein the heterocycloalkyl is unsubstituted or is substituted with $C_1$-$C_6$-alkyl or hydroxy,
  iv) —NH(hydroxy-$C_1$-$C_6$-alkyl),
  v) —NH-(5-membered heteroaryl-$C_1$-$C_6$-alkyl having as heteroatom O),
  vi) 5 or 6-membered heterocycloalkyl-$C_1$-$C_6$-alkyl having at least one heteroatom selected from O or N,
  vii) 5 or 6-membered heterocycloalkyl having at least one heteroatom selected from O or N and that is unsubstituted or is substituted with hydroxy, —C(O)OR' wherein R' is $C_1$-$C_6$-alkyl, halogen or $C_1$-$C_6$-alkyl,
  viii) amino,
  ix) —NH(amino-$C_1$-$C_6$-alkyl), or
  x) —N($C_1$-$C_6$-alkyl)$_2$;
$R_6$ is selected from:
a) $C_1$-$C_6$-alkyl that is unsubstituted or is substituted with one or two hydroxy groups;
b) phenyl substituted with at least one of the following groups:
  i) halogen,
  ii) $C_1$-$C_6$-alkyl, or
  iii) $C_1$-$C_6$-alkoxy;
c) 5 or 6-membered heterocycloalkyl having a heteroatom selected from O or N and substituted with $C_1$-$C_6$-alkyl;
d) $C_3$-$C_8$-cycloalkyl substituted with $R_8$; or
e) —(CH$_2$)$_n$R$_9$ wherein n equals 1, 2 or 3;
$R_7$ is:
a) hydrogen; or
b) $C_1$-$C_6$-alkyl;
$R_8$ is selected from:
a) hydrogen;
b) hydroxy;
c) $C_1$-$C_6$-alkyl that is unsubstituted or is substituted with hydroxy;
d) C(O)O—$C_1$-$C_6$-alkyl; or
e) —NH$_2$; and
$R_9$ is selected from:
a) $C_3$-$C_8$-cycloalkyl that is unsubstituted or is substituted with an unsubstituted $C_1$-$C_6$-alkyl;
b) 5 or 6-membered heterocycloalkyl having a heteroatom selected from N and O and that is unsubstituted or is substituted with $C_1$-$C_6$-alkyl;

c) 5 or 6-membered heteroaryl having a heteroatom selected from N and O that is unsubstituted or is and that is unsubstituted or is substituted with $C_1$-$C_6$-alkyl; or d) phenyl.

2. The triazolopyridine compound according to claim 1 wherein:

$R_1$ is selected from:
a) hydrogen; or
b) Br;

$R_3$ is selected from:
a) hydrogen;
b) halogen; or
c) $C_1$-$C_6$ alkyl optionally substituted with at least one fluoro;

$R_5$ is selected from:
a) $C_1$-$C_6$-alkyl that is unsubstituted or is substituted with at least one of the following groups:
  i) $C_1$-$C_6$ alkoxycarbonyl,
  ii) $C_1$-$C_6$-alkoxy,
  iii) -NHC(O)R' wherein R' is an aryl that is unsubstituted or is substituted with $C_1$-$C_6$-alkyl, or
  iv) benzyloxy;
b) aryl-$C_1$-$C_6$-alkyl;
c) 5 or 6-membered heteroaryl-$C_1$-$C_6$-alkyl having a heteroatom selected from N, S or O that is unsubstituted or is and that is unsubstituted or is substituted with $C_1$-$C_6$-alkyl, halogen or $C_1$-$C_6$-alkoxy;
d) $C_3$-$C_6$ cycloalkyl that is unsubstituted or is substituted with phenyl;
e) 3 to 8-membered heterocycloalkyl having a heteroatom selected from N, S or O and that is unsubstituted or is substituted with an acyl group;
f) aryl that is unsubstituted or is substituted with at least one of the following groups:
  i) $C_1$-$C_6$-alkyl optionally substituted with a γ-lactam or δ-lactam,
  ii) halogen,
  iii) $C_1$-$C_6$-alkoxy,
  iv) perfluoro-$C_1$-$C_6$-alkyl,
  v) at least one $C_1$-$C_6$-alkoxy that is unsubstituted or is substituted with $C_1$-$C_6$-alkoxy carbonyl,
  vi) phenyl,
  vii) $C_1$-$C_6$-alkyl sulfonyl,
  viii) —NC(O)$C_1$-$C_6$-alkyl,
  ix) amino-$C_1$-$C_6$-alkyl wherein amino is selected from —$NH_2$, —$NHC_1$-$C_6$-alkyl, —N($C_1$-$C_6$-alkyl)$_2$, N($C_1$-$C_6$-alkyl)($C_1$-$C_6$-alkoxy-$C_1$-$C_6$-alkyl), and the two substituents $C_1$-$C_6$-alkyl can be the same or different, and wherein the two substituents may form a 3 to 8-membered heterocycloalkyl with the N to which they are attached and wherein the heterocycloalkyl is unsubstituted or is substituted with $C_1$-$C_6$-alkyl or with hydroxy,
  x) —N($C_1$-$C_6$-alkyl) ($C_1$-$C_6$-alkoxy-$C_1$-$C_6$-alkyl),
  xi) 5 to 6-membered heterocycloalkyl-$C_1$-$C_6$-alkyl having a heteroatom selected from N and O, or
  xii) amido-$C_1$-$C_6$-alkyl;
g) 5 to 10-membered heteroaryl having at least one heteroatom selected from N that is unsubstituted or is substituted with halogen; or
h) pyridinyl that is unsubstituted or is substituted with at least one of the following groups:
  i) halogen,
  ii) $C_1$-$C_6$-alkyl that is unsubstituted or is substituted with a 5 or 6-membered heterocycloalkyl having at least one heteroatom selected from O or N,
  iii) 5 or 6-membered heterocycloalkyl having at least one heteroatom selected from O or N,
  iv) —NH(hydroxy-$C_1$-$C_6$-alkyl),
  v) —NH-(5-membered heteroaryl-$C_1$-$C_6$-alkyl having as heteroatom O),
  vi) 5 or 6-membered heterocycloalkyl-$C_1$-$C_6$-alkyl having at least one heteroatom selected from O or N,
  vii) 5 or 6-membered heterocycloalkyl having at least one heteroatom selected from O or N and that is unsubstituted or is substituted with hydroxy, —C(O) OR' wherein R' is $C_1$-$C_6$-alkyl, halogen or $C_1$-$C_6$-alkyl,
  viii) amino,
  ix) —NH(amino-$C_1$-$C_6$-alkyl), or
  x) —N($C_1$-$C_6$-alkyl)$_2$;

$R_6$ is selected from:
a) $C_1$-$C_6$-alkyl that is unsubstituted or is substituted with one or two hydroxy groups,
b) phenyl that is unsubstituted or is substituted with at least one of the following groups:
  i) halogen,
  ii) $C_1$-$C_6$-alkyl, or
  iii) $C_1$-$C_6$-alkoxy;
c) 5 or 6-membered heterocycloalkyl having a heteroatom selected from O or N and that is unsubstituted or is substituted with $C_1$-$C_6$-alkyl;
d) $C_3$-$C_8$-cycloalkyl that is unsubstituted or is substituted with $R_8$; or
e) —$(CH_2)_n R_9$ wherein n equals 1, 2 or 3;

$R_7$ is:
a) hydrogen; or
b) $C_1$-$C_6$-alkyl;

$R_8$ is selected from:
a) hydrogen;
b) hydroxy;
c) unsubstituted or substituted $C_1$-$C_6$-alkyl wherein the substituent is hydroxyl;
d) C(O)O—$C_1$-$C_6$-alkyl; or
e) —$NH_2$; and $R_9$ is selected from:
a) $C_3$-$C_8$-cycloalkyl that is unsubstituted or is substituted with an unsubstituted $C_1$-$C_6$-alkyl;
b) 5 or 6-membered heterocycloalkyl having a heteroatom selected from N and O that is unsubstituted or is substituted with $C_1$-$C_6$-alkyl;
c) 5 or 6-membered heteroaryl having a heteroatom selected from N and O that is unsubstituted or is substituted with $C_1$-$C_6$-alkyl; or
d) phenyl.

3. A triazolopyridine compound selected from:
N-[5-(cyclopropylamino)[1,2,4]triazolo[1,5-a]pyridin-2-yl]nicotinamide;
N-(5-pyrrolidin-1-yl[1,2,4]triazolo[1,5-a]pyridin-2-yl)nicotinamide;
N-[5-(cyclopentylamino)[1,2,4]triazolo[1,5-a]pyridin-2-yl]benzamide;
N-{5-[(3-methoxypropyl)amino][1,2,4]triazolo[1,5-a]pyridin-2-yl}benzamide;
N-{5-[(2-furylmethyl)amino][1,2,4]triazolo[1,5-a]pyridin-2-yl}benzamide;
N-{5-[(tetrahydrofuran-2-ylmethyl)amino][1,2,4]triazolo[1,5-a]pyridin-2-yl}benzamide;
N-[5-(cyclohexylamino)[1,2,4]triazolo[1,5-a]pyridin-2-yl]benzamide;
N-(5-{[1-(hydroxymethyl)propyl]amino}[1,2,4]triazolo[1,5-a]pyridin-2-yl)benzamide;

N-{5-[(2-methoxyethyl)amino][1,2,4]triazolo[1,5-a]pyridin-2-yl}benzamide;
N-{5-[(2,3-dihydroxypropyl)amino][1,2,4]-triazolo[1,5-a]pyridin-2-yl}benzamide;
N-[5-(benzylamino)[1,2,4]triazolo[1,5-a]pyridin-2-yl]nicotinamide;
N-[5-(cycloheptylamino)[1,2,4]triazolo[1,5-a]pyridin-2-yl]nicotinamide dihydrochloride;
N-[5-(cyclohexylamino)[1,2,4]triazolo[1,5-a]pyridin-2-y]nicotinamide;
N-(5-{[(5-methyl-2-furyl)methyl]amino}[1,2,4]triazolo[1,5-a]pyridin-2-yl)nicotinamide;
N-{5-[(tetrahydrofuran-2-ylmethyl)amino][1,2,4]triazolo[1,5-a]pyridin-2-yl}nicotinamide;
N-[5-(cyclooctylamino)[1,2,4]triazolo[1,5-a]pyridin-2-yl]nicotinamide;
N-[5-[cyclohexyl(methyl)amino][1,2,4]triazolo[1,5-a]pyridin-2-yl]nicotinamide;
N-[5-(tetrahydro-2H-pyran-4-ylamino)[1,2,4]triazolo[1,5-a]pyridin-2-yl]nicotinamide;
N-{5-(1-methylpiperidin-4-yl)amino][1,2,4]-triazolo[1,5-a]pyridin-2-yl}nicotinamide;
N-{5-[(3-aminocyclohexyl)amino][1,2,4]triazolo[1,5-a]pyridin-2-yl}benzamide;
N-{5-[(1-methylpiperidin-4-yl)amino][1,2,4]triazolo[1,5-a]pyridin-2-yl}benzamide;
N-[5-(cyclopropylamino)-7-(trifluoromethyl)[1,2,4]triazolo[1,5-a]pyridin-2-yl]nicotinamide;
N-[5-(cyclohexylamino)-7-(trifluoromethyl)[1,2,4]triazolo[1,5-a]pyridin-2-yl]nicotinamide;
N-[5-(cycloheptylamino)-7-(trifluoromethyl)[1,2,4]triazolo[1,5-a]pyridin-2-yl]nicotinamide;
N-[5-(cyclopentylamino)-7-(trifluoromethyl)[1,2,4]triazolo[1,5-a]pyridin-2-yl]nicotinamide;
N-{5-[(cyclohexylmethyl)amino]-7-(trifluoromethyl)[1,2,4]triazolo[1,5-a]pyridin-2-yl}nicotinamide;
N-{5-[(3-hydroxycyclohexyl)amino][1,2,4]triazolo[1,5-a]pyridin-2-yl}nicotinamide;
N-[5-[(4-tert-butylcyclohexyl)amino][1,2,4]triazolo[1,5-a]pyridin-2-yl]nicotinamide;
N-[5-(tetrahydro-2H-pyran-3-ylamino)[1,2,4]triazolo[1,5-a]pyridin-2-yl]benzamide;
N-[5-(cycloheptylamino)[1,2,4]triazolo[1,5-a]pyridin-2-yl]-4-(morpholin-4-ylmethyl)benzamide;
N-{5-[(trans-4-hydroxycyclohexyl)amino][1,2,4]triazolo[1,5-a]pyridin-2-yl}nicotinamide;
N-[5-(cyclobutylamino)-7-(trifluoromethyl)[1,2,4]-triazolo[1,5-a]pyridin-2-yl]nicotinamide;
N-[5-(cyclohexylamino)[1,2,4]triazolo[1,5-a]pyridin-2-yl]-6-morpholin-4-ylnicotinamide;
N-[5-(cyclohexylamino)[1,2,4]triazolo[1,5-a]pyridin-2-yl]-4-[(dimethylamino)methyl]benzamide;
N-[5-(cyclohexylamino)[1,2,4]triazolo[1,5-a]pyridin-2-yl]-3-(morpholin-4-ylmethyl)benzamide;
N-[5-[(cyclopropylmethyl)amino]-7-(trifluoromethyl)[1,2,4]triazolo[1,5-a]pyridin-2-yl]nicotinamide;
methyltrans-4-{[2-[(pyridin-3-ylcarbonyl)amino]-7-(trifluoromethyl)[1,2,4]triazolo[1,5-a]pyridin-5-yl]amino}cyclohexanecarboxylate;
N-[5-{[(1RS,2RS)-2-(hydroxymethyl)cyclohexyl]amino}-7-(trifluoromethyl)[1,2,4]triazolo[1,5-a]pyridin-2-yl}nicotinamide;
N-[6-bromo-5-(cyclohexylamino)[1,2,4]triazolo[1,5-a]pyridin-2-yl]nicotinamide;
N-[5-(cycloheptylamino)[1,2,4]triazolo[1,5-a]pyridin-2-yl]tetrahydro-2H-pyran-4-carboxamide;
N-(3-{[5-(cyclohexylamino)[1,2,4]triazolo[1,5-a]pyridin-2-yl]amino}-3-oxopropyl)benzamide;
N-[5-(isopropylamino)-7-(trifluoromethyl)[1,2,4]triazolo[1,5-a]pyridin-2-yl]nicotinamide;
N-[5-(sec-butylamino)-7-(trifluoromethyl)[1,2,4]triazolo[1,5-a]pyridin-2-yl]nicotinamide;
N-[5-(methylamino)-7-(trifluoromethyl)[1,2,4]triazolo[1,5-a]pyridin-2-yl]nicotinamide;
N-[5-(cyclohexylamino)[1,2,4]triazolo[1,5-a]pyridin-2-yl]-6-(2-pyrrolidin-1-ylethyl)nicotinamide;
N-5-(cyclohexylamino)[1,2,4]triazolo[1,5-a]pyridin-2-yl]-6-(morpholin-4-ylmethyl)nicotinamide;
N-{5-[(cyclohexylmethyl)amino][1,2,4]triazolo[1,5-a]pyridin-2-yl}nicotinamide;
N-{5-[(4-hydroxycyclohexyl)amino][1,2,4]triazolo[1,5-a]pyridin-2-yl}-3-methoxybenzamide;
N-[5-(cyclopentylamino)[1,2,4]triazolo[1,5-a]pyridin-2-yl]-2-furamide;
N-[7-chloro-5-(cyclobutylamino)[1,2,4]triazolo[1,5-a]pyridin-2-yl]nicotinamide;
N-[7-chloro-5-(cyclopentylamino)[1,2,4]triazolo[1,5-a]pyridin-2-yl]nicotinamide;
N-[7-chloro-5-(cyclohexylamino)[1,2,4]triazolo[1,5-a]pyridin-2-yl]nicotinamide;
N-[5-(sec-butylamino)-7-chloro[1,2,4]triazolo[1,5-a]pyridin-2-yl]nicotinamide;
N-[7-chloro-5-(cyclopropylamino)[1,2,4]triazolo[1,5-a]pyridin-2-yl]nicotinamide;
N-[5-[(2-methoxyethyl)amino]-7-(trifluoromethyl)[1,2,4]triazolo[1,5-a]pyridin-2-yl]nicotinamide;
N-[5-[(3-hydroxypropyl)amino]-7-(trifluoromethyl)[1,2,4]triazolo[1,5-a]pyridin-2-yl]nicotinamide;
N-[5-[(2-hydroxyethyl)amino]-7-(trifluoromethyl)[1,2,4]triazolo[1,5-a]pyridin-2-yl]nicotinamide; N-[5-(dimethylamino)-7-(trifluoromethyl)[1,2,4]triazolo[1,5-a]pyridin-2-yl]nicotinamide;
N-[(cyclohexylamino)[1,2,4]triazolo[1,5-a]pyridin-2-yl]-2-pyridin-3-ylacetamide;
N-[5-(cyclohexylamino)[1,2,4]triazolo[1,5-a]pyridin-2-yl]-4-(piperidin-1-ylmethyl)benzamide;
N-[5-(cyclohexylamino)[1,2,4]triazolo[1,5-a]pyridin-2-yl]-4-(pyrrolidin-1-ylmethyl)benzamide;
N-[5-(cyclohexylamino)[1,2,4]triazolo[1,5-a]pyridin-2-yl]-4-{[(2-methoxyethyl)(methyl)amino]methyl}benzamide;
N-[5-(cyclohexylamino)[1,2,4]triazolo[1,5-a]pyridin-2-yl]-6-methylnicotinamide;
N-[5-(cyclohexylamino)[1,2,4]triazolo[1,5-a]pyridin-2-yl]-6-[(3-hydroxypropyl)amino]nicotinamide;
N-[5-(cyclohexylamino)[1,2,4]triazolo[1,5-a]pyridin-2-yl]-6-[(2-furylmethyl)amino]nicotinamide;
N-[5-(cyclohexylamino)[1,2,4]triazolo[1,5-a]pyridin-2-yl]nicotinamide 1-oxide;
N-[5-(isopropylamino)-7-(trifluoromethyl)[1,2,4]triazolo[1,5-a]pyridin-2-yl]-2-pyridin-3-ylacetamide trihydrochloride;
N-[5-[(1-ethylpropyl)amino]-7-(trifluoromethyl)[1,2,4]triazolo[1,5-a]pyridin-2-yl]nicotinamide;
N-[5-(isopropylamino)-7-(trifluoromethyl)[1,2,4]triazolo[1,5-a]pyridin-2-yl]nicotinamide 1-oxide;
N-[5-[(3-hydroxycyclohexyl)amino]-7-(trifluoromethyl)[1,2,4]triazolo[1,5-a]pyridin-2-yl]nicotinamide formic acid;
N-{7-chloro-5-[(3-hydroxycyclohexyl)amino][1,2,4]triazolo[1,5-a]pyridin-2-yl}nicotinamide formic acid;

N-[5-(cyclopropylamino)-7-(trifluoromethyl)[1,2,4]-triazolo[1,5-a]pyridin-2-yl]-4-[(dimethylamino)methyl]benzamide;
N-[5-(cyclopropylamino)-7-(trifluoromethyl)[1,2,4]triazolo[1,5-a]pyridin-2-yl]-4-[(2-oxopyrrolidin-1-yl)methyl]benzamide;
N-[5-(cyclopropylamino)-7-(trifluoromethyl)[1,2,4]triazolo[1,5-a]pyridin-2-yl]-6-pyrrolidin-1-ylnicotinamide;
N-[5-(cyclopropylamino)-7-(trifluoromethyl)[1,2,4]triazolo[1,5-a]pyridin-2-yl]-6-methylnicotinamide;
N-[5-{1R,2S)-2-(hydroxymethyl)cyclohexyl]amino}-7-(trifluoromethyl)[1,2,4]triazolo[1,5-a]pyridin-2-yl]nicotinamide hydrochloride;
N-[5-(cyclopropylamino)-7-(trifluoromethyl)[1,2,4]triazolo[1,5-a]pyridin-2-yl]-4-[(4-hydroxypiperidin-1-yl)methyl]benzamide;
N-[5-(cyclopropylamino)-7-(trifluoromethyl)[1,2,4]triazolo[1,5-a]pyridin-2-yl]-4-(pyrrolidin-1-ylmethyl)benzamide;
N-[5-(cyclopropylamino)-7-(trifluoromethyl)[1,2,4]triazolo[1,5-a]pyridin-2-yl]-6-(4-hydroxypiperidin-1-yl)nicotinamide;
N-[5-(cyclopropylamino)-7-(trifluoromethyl)[1,2,4]-triazolo[1,5-a]pyridin-2-yl]-6-piperazin-1-ylnicotinamide;
N-[5-(cyclopropylamino)-7-(trifluoromethyl)[1,2,4]-triazolo[1,5-a]pyridin-2-yl]-6-(dimethylamino)nicotinamide;
N-[6-bromo-5-(cyclopentylamino)[1,2,4]triazolo[1,5-a]pyridin-2-yl]-6-morpholin-4-ylnicotinamide;
N-[5-(cyclopropylamino)-7-(trifluoromethyl)[1,2,4]triazolo[1,5-a]pyridin-2-yl]-6-morpholin-4-ylnicotinamide;
N-[5-(cyclohexylamino)[1,2,4]triazolo[1,5-a]pyridin-2-yl]-6-(dimethylamino)nicotinamide;
tert-butyl 4-[5-({[5-(cyclopropylamino)-7-(trifluoromethyl)[1,2,4]-triazolo[1,5-a]pyridin-2-yl]amino}carbonyl)pyridin-2-yl]piperazine-1-carboxylate;
N-[5-(cyclohexylamino)[1,2,4]-triazolo[1,5-a]pyridin-2-yl]-4-[(4-hydroxypiperidin-1-yl)methyl]benzamide;
N-[5-(cyclohexylamino)[1,2,4]-triazolo[1,5-a]pyridin-2-yl]-6-(4-fluoropiperidin-1-yl)nicotinamide;
N-[5-(cyclohexylamino)[1,2,4]triazolo[1,5-a]pyridin-2-yl]-6-(1H-pyrazol-1-yl)nicotinamide;
tert-butyl 4-[5-({[5-(cyclohexylamino)[1,2,4]triazolo[1,5-a]pyridin-2-yl]amino}carbonyl)pyridin-2-yl]piperazine-1-carboxylate;
N-[5-(cyclopropylamino)-7-(trifluoromethyl)[1,2,4]triazolo[1,5-a]pyridin-2-yl]-6-[(3-hydroxypropyl)amino]nicotinamide;
N-[5-(isopropylamino)-7-(trifluoromethyl)[1,2,4]triazolo[1,5-a]pyridin-2-yl]-6-(morpholin-4-ylmethyl)nicotinamide;
N-[5-[(pyrrolidin-3-ylmethyl)amino]-7-(trifluoromethyl)[1,2,4]triazolo[1,5-a]pyridin-2-yl]nicotinamide;
N-[5-(cyclohexylamino)[1,2,4]triazolo[1,5-a]pyridin-2-yl]-4-(piperazin-1-ylmethyl)benzamide;
N-[5-(cyclohexylamino)[1,2,4]triazolo[1,5-a]pyridin-2-yl]-4-[(4-formylpiperazin-1-yl)methyl]benzamide;
N-[5-(piperidin-3-ylamino)-7-(trifluoromethyl)[1,2,4]triazolo[1,5-a]pyridin-2-yl]nicotinamide;
N-[5-(sec-butylamino)-7-chloro[1,2,4]triazolo[1,5-a]pyridin-2-yl]-6-[(2-methoxyethyl)(methyl)amino]nicotinamide;
N-[5-(sec-butylamino)-7-chloro[1,2,4]-triazolo[1,5-a]pyridin-2-yl]-6-[(3-hydroxypropyl)amino]nicotinamide;
N-[5-(sec-butylamino)-7-chloro[1,2,4]triazolo[1,5-a]pyridin-2-yl]-6-morpholin-4-ylnicotinamide;
N-[5-(sec-butylamino)-7-chloro[1,2,4]triazolo[1,5-a]pyridin-2-yl]-4-[(2-methoxyethyl)(methyl)amino]methyl]benzamide;
N-[5-(sec-butylamino)-7-chloro[1,2,4]triazolo[1,5-a]pyridin-2-yl]-6-methylnicotinamide;
N-[7-chloro-5-(isopropylamino)[1,2,4]triazolo[1,5-a]pyridin-2-yl]nicotinamide;
N-[5-[(3-isopropoxyphenyl)amino]-7-(trifluoromethyl)[1,2,4]triazolo[1,5-a]pyridin-2-yl]nicotinamide;
N-[5-[(3-fluoro-4-methoxyphenyl)amino]-7-(trifluoromethyl)[1,2,4]triazolo[1,5-a]pyridin-2-yl]nicotinamide;
N-[5-{[3-(benzyloxy)phenyl]amino}-7-(trifluoromethyl)[1,2,4]triazolo[1,5-a]pyridin-2-yl]nicotinamide;
N-[5-(sec-butylamino)-7-chloro[1,2,4-triazolo[1,5-a]pyridin-2-yl]-4-(morpholin-4-ylmethyl)benzamide;
N-[5-(isopropylamino)-7-(trifluoromethyl)[1,2,4]triazolo[1,5-a]pyridin-2-yl]-6-methylnicotinamide;
6-chloro-N-[5-(isopropylamino)-7-(trifluoromethyl)[1,2,4]triazolo[1,5-a]pyridin-2-yl]nicotinamide;
6-[(2-aminoethyl)amino]-N-[5-(isopropylamino)-7-(trifluoromethyl)[1,2,4]triazolo[1,5-a]pyridin-2-yl]nicotinamide;
N-[5-(sec-butylamino)-7-methyl[1,2,4]triazolo[1,5-a]pyridin-2-yl]nicotinamide; or
N-[5-(isopropylamino)-7-methyl[1,2,4]triazolo[1,5-a]pyridin-2-yl]nicotinamide.

4. A pharmaceutical composition containing at least one triazolopyridine amide compound according to claim 1 and a pharmaceutically acceptable carrier, diluent or excipient.

5. A pharmaceutical composition containing at least one triazolopyridine amide compound according to claim 3 and a pharmaceutically acceptable carrier, diluent or excipient.

* * * * *